US010982208B2

(12) United States Patent
Jacobson et al.

(10) Patent No.: US 10,982,208 B2
(45) Date of Patent: *Apr. 20, 2021

(54) PROTEIN ARRAYS AND METHODS OF USING AND MAKING THE SAME

(71) Applicant: Gen9, Inc., Boston, MA (US)

(72) Inventors: Joseph Jacobson, Newton, MA (US); Michael E. Hudson, Framingham, MA (US); Larry Li-Yang Chu, Cambridge, MA (US)

(73) Assignee: Gen9, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/578,488

(22) Filed: Sep. 23, 2019

(65) Prior Publication Data

US 2020/0181604 A1 Jun. 11, 2020

Related U.S. Application Data

(62) Division of application No. 13/884,446, filed as application No. PCT/US2011/060217 on Nov. 10, 2011, now Pat. No. 10,457,935.

(60) Provisional application No. 61/412,941, filed on Nov. 12, 2010.

(51) Int. Cl.
C12N 15/10 (2006.01)
B01J 19/00 (2006.01)
C40B 50/14 (2006.01)

(52) U.S. Cl.
CPC ...... *C12N 15/1086* (2013.01); *B01J 19/0046* (2013.01); *C40B 50/14* (2013.01); *B01J 2219/00378* (2013.01); *B01J 2219/00509* (2013.01); *B01J 2219/00531* (2013.01); *B01J 2219/00596* (2013.01); *B01J 2219/00621* (2013.01); *B01J 2219/00644* (2013.01); *B01J 2219/00659* (2013.01); *B01J 2219/00722* (2013.01); *B01J 2219/00725* (2013.01)

(58) Field of Classification Search
None
See application file for complete search history.

(56) References Cited

U.S. PATENT DOCUMENTS

| 4,500,707 | A | 2/1985 | Caruthers et al. |
| 4,610,544 | A | 9/1986 | Riley |
| 4,683,195 | A | 7/1987 | Mullis |
| 4,683,202 | A | 7/1987 | Mullis |
| 4,689,405 | A | 8/1987 | Frank |
| 4,725,677 | A | 2/1988 | Koester et al. |
| 4,800,159 | A | 1/1989 | Mullis |
| 4,888,286 | A | 12/1989 | Crea |
| 4,959,317 | A | 9/1990 | Sauer |
| 4,965,188 | A | 10/1990 | Mullis |
| 4,999,294 | A | 3/1991 | Looney |
| 5,047,524 | A | 9/1991 | Andrus et al. |
| 5,093,251 | A | 3/1992 | Richards et al. |
| 5,096,825 | A | 3/1992 | Barr et al. |
| 5,104,789 | A | 4/1992 | Permar |
| 5,104,792 | A | 4/1992 | Silver |
| 5,132,215 | A | 8/1992 | Jayarama |
| 5,143,854 | A | 9/1992 | Pirrung |
| 5,288,514 | A | 2/1994 | Pirrung |
| 5,356,802 | A | 10/1994 | Chandrasegaran |
| 5,384,261 | A | 1/1995 | Winker |
| 5,395,750 | A | 3/1995 | Dillon et al. |
| 5,405,783 | A | 4/1995 | Pirrung |
| 5,424,186 | A | 6/1995 | Fodor |
| 5,436,150 | A | 7/1995 | Chandrasegaran |
| 5,436,327 | A | 7/1995 | Southern |
| 5,445,934 | A | 8/1995 | Fodor |
| 5,459,039 | A | 10/1995 | Modrich |
| 5,474,796 | A | 12/1995 | Brennan |
| 5,498,531 | A | 3/1996 | Jarrell |
| 5,508,169 | A | 4/1996 | Deugau et al. |
| 5,510,270 | A | 4/1996 | Fodor |
| 5,512,463 | A | 4/1996 | Stemmer |
| 5,514,789 | A | 5/1996 | Kempe |
| 5,527,681 | A | 6/1996 | Holmes |
| 5,541,061 | A | 7/1996 | Fodor |
| 5,556,750 | A | 9/1996 | Modrich et al. |

(Continued)

FOREIGN PATENT DOCUMENTS

| CN | 1145641 A | 3/1997 |
| CN | 1468313 A | 1/2004 |

(Continued)

OTHER PUBLICATIONS

[No Author Listed], TnT.RTM. coupled reticulocyte lysate system, Technical Bulletin (Promega, Madison, Wis), 2013.
Abremski et al. Studies on the properties of P 1 site-specific recombination: evidence for topologically unlinked products following recombination. Cell 32:1301-1311 (1983).
Abremski K. et al. Bacteriophage P1 site-specific recombination. Purification and properties of the Cre recombinase protein (1984) J. Mol. Biol. 259: 1509-1514.
Adessi et al., "Solid phase DNA amplification: characterisation of primer attachment and amplification mechanisms," Nucleic Acids Research, 28(20):E87, (Oct. 15, 2000).
Afshari et al. "Application of Complementary DNA Microarray Technology to Carcinogen Identification, Toxicology, and Drug Safety". Cancer Research, 59, 4759-4760, Oct. 1, 1999.

(Continued)

*Primary Examiner* — Kaijiang Zhang
(74) *Attorney, Agent, or Firm* — Wolf, Greenfield & Sacks, P.C.

(57) ABSTRACT

Methods and devices are provided for preparing a protein array having a plurality of proteins. In one embodiment, the method includes providing a plurality of nucleic acids each having a predefined sequence and expressing in vitro a plurality of proteins from the plurality of nucleic acids. In another embodiment, protein arrays having a solid surface and a microvolume are also provided. The solid surface can have a plurality of anchor oligonucleotides capable of hybridizing with a plurality of nucleic acids. The microvolume can cover each of the plurality of anchor oligonucleotides and can be configured to produce a polypeptide from each of the plurality of nucleic acids.

10 Claims, 6 Drawing Sheets

Specification includes a Sequence Listing.

(56) References Cited

U.S. PATENT DOCUMENTS

| | | | |
|---|---|---|---|
| 5,604,097 | A | 2/1997 | Brenner |
| 5,605,793 | A | 2/1997 | Stemmer |
| 5,624,711 | A | 4/1997 | Sundberg |
| 5,639,603 | A | 6/1997 | Dower |
| 5,641,658 | A | 6/1997 | Adams |
| 5,653,939 | A | 8/1997 | Hollis |
| 5,674,742 | A | 10/1997 | Northrup |
| 5,679,522 | A | 10/1997 | Modrich |
| 5,695,940 | A | 12/1997 | Drmanac |
| 5,700,637 | A | 12/1997 | Southern |
| 5,700,642 | A | 12/1997 | Monforte |
| 5,702,894 | A | 12/1997 | Modrich |
| 5,738,829 | A | 4/1998 | Kempe |
| 5,739,386 | A | 4/1998 | Holmes |
| 5,750,335 | A | 5/1998 | Gifford |
| 5,766,550 | A | 6/1998 | Kaplan et al. |
| 5,770,358 | A | 6/1998 | Dower |
| 5,780,272 | A | 7/1998 | Jarrell |
| 5,795,714 | A | 8/1998 | Cantor |
| 5,830,655 | A | 11/1998 | Montforte |
| 5,830,721 | A | 11/1998 | Stemmer et al. |
| 5,834,252 | A | 11/1998 | Stemmer |
| 5,858,754 | A | 1/1999 | Modrich |
| 5,861,482 | A | 1/1999 | Modrich |
| 5,871,902 | A | 2/1999 | Weininger |
| 5,876,604 | A | 3/1999 | Nemser et al. |
| 5,877,280 | A | 3/1999 | Wetmur |
| 5,912,129 | A | 6/1999 | Vinayagamoorthy et al. |
| 5,916,794 | A | 6/1999 | Chandrasegaran |
| 5,922,539 | A | 7/1999 | Modrich |
| 5,928,905 | A | 7/1999 | Stemmer |
| 5,929,208 | A | 7/1999 | Heller |
| 5,942,609 | A | 8/1999 | Hunkapiller |
| 5,953,469 | A | 9/1999 | Zhou |
| 6,008,031 | A | 12/1999 | Modrich et al. |
| 6,013,440 | A | 1/2000 | Lipshutz |
| 6,017,696 | A | 1/2000 | Heller |
| 6,027,877 | A | 2/2000 | Wagner, Jr. |
| 6,042,211 | A | 3/2000 | Hudson et al. |
| 6,093,302 | A | 7/2000 | Montgomery |
| 6,103,463 | A | 8/2000 | Chetverin |
| 6,110,668 | A | 8/2000 | Strizhov et al. |
| 6,136,568 | A | 10/2000 | Hiatt |
| 6,143,527 | A | 11/2000 | Pachuk et al. |
| 6,150,102 | A | 11/2000 | Mills |
| 6,150,141 | A | 11/2000 | Jarrell |
| 6,165,793 | A | 12/2000 | Stemmer |
| 6,177,558 | B1 | 1/2001 | Brennan et al. |
| 6,242,211 | B1 | 6/2001 | Peterson |
| 6,248,521 | B1 | 6/2001 | VanNess |
| 6,261,797 | B1 | 7/2001 | Sorge |
| 6,271,957 | B1 | 8/2001 | Quate |
| 6,277,632 | B1 | 8/2001 | Harney |
| 6,280,595 | B1 | 8/2001 | Montgomery |
| 6,284,463 | B1 | 9/2001 | Hasebe |
| 6,287,825 | B1 | 9/2001 | Weissman |
| 6,287,861 | B1 | 9/2001 | Stemmer |
| 6,291,242 | B1 | 9/2001 | Stemmer |
| 6,315,958 | B1 | 11/2001 | Singh-Gasson |
| 6,322,971 | B1 | 11/2001 | Chetverin |
| 6,326,489 | B1 | 12/2001 | Church et al. |
| 6,333,153 | B1 | 12/2001 | Fishel |
| 6,346,399 | B1 | 2/2002 | Weissman |
| 6,355,412 | B1 | 3/2002 | Stewart et al. |
| 6,355,423 | B1 | 3/2002 | Rothberg et al. |
| 6,358,712 | B1 | 3/2002 | Jarrell |
| 6,365,355 | B1 | 4/2002 | McCutchen-Maloney |
| 6,372,429 | B1 | 4/2002 | Sharon |
| 6,372,434 | B1 | 4/2002 | Weissman |
| 6,372,484 | B1 | 4/2002 | Ronchi |
| 6,375,903 | B1 | 4/2002 | Cerrina |
| 6,376,246 | B1 | 4/2002 | Crameri et al. |
| 6,406,847 | B1 | 6/2002 | Cox |
| 6,410,220 | B1 | 6/2002 | Hodgson et al. |
| 6,416,164 | B1 | 7/2002 | Stearns et al. |
| 6,426,184 | B1 | 7/2002 | Gao |
| 6,432,360 | B1 | 8/2002 | Church |
| 6,444,111 | B1 | 9/2002 | Montgomery |
| 6,444,175 | B1 | 9/2002 | Singh-Gasson |
| 6,444,650 | B1 | 9/2002 | Cech et al. |
| 6,444,661 | B1 | 9/2002 | Barton et al. |
| 6,472,184 | B1 | 10/2002 | Hegemann et al. |
| 6,479,652 | B1 | 11/2002 | Crameri et al. |
| 6,480,324 | B2 | 11/2002 | Quate |
| 6,489,146 | B2 | 12/2002 | Stemmer |
| 6,495,318 | B2 | 12/2002 | Harney |
| 6,506,603 | B1 | 1/2003 | Stemmer |
| 6,509,156 | B1 | 1/2003 | Stewart |
| 6,511,849 | B1 | 1/2003 | Wang |
| 6,514,704 | B2 | 2/2003 | Bruce et al. |
| 6,521,427 | B1 | 2/2003 | Evans |
| 6,534,271 | B2 | 3/2003 | Furste |
| 6,537,776 | B1 | 3/2003 | Short |
| 6,565,727 | B1 | 5/2003 | Shenderov |
| 6,586,211 | B1 | 7/2003 | Stahler |
| 6,593,111 | B2 | 7/2003 | Baric et al. |
| 6,596,239 | B2 | 7/2003 | Williams et al. |
| 6,605,451 | B1 | 8/2003 | Marmaro |
| 6,610,499 | B1 | 8/2003 | Fulwyler et al. |
| 6,613,581 | B1 | 9/2003 | Wada |
| 6,632,641 | B1 | 10/2003 | Brennan |
| 6,650,822 | B1 | 11/2003 | Zhou |
| 6,658,802 | B2 | 12/2003 | Lucas, Jr. et al. |
| 6,660,475 | B2 | 12/2003 | Jack et al. |
| 6,664,112 | B2 | 12/2003 | Mulligan |
| 6,664,388 | B2 | 12/2003 | Nelson |
| 6,670,127 | B2 | 12/2003 | Evans |
| 6,670,605 | B1 | 12/2003 | Short |
| 6,800,439 | B1 | 10/2004 | McGall |
| 6,802,593 | B2 | 10/2004 | Ellson et al. |
| 6,824,866 | B1 | 11/2004 | Glazer |
| 6,830,890 | B2 | 12/2004 | Lockhart |
| 6,833,450 | B1 | 12/2004 | Mcgall |
| 6,846,655 | B1 | 1/2005 | Wagner et al. |
| 6,897,025 | B2 | 5/2005 | Cox |
| 6,911,132 | B2 | 6/2005 | Pamula et al. |
| 6,921,818 | B2 | 7/2005 | Sproat |
| 6,932,097 | B2 | 8/2005 | Ellson et al. |
| 6,946,296 | B2 | 9/2005 | Patten et al. |
| 6,955,901 | B2 | 10/2005 | Schouten |
| 6,969,587 | B2 | 11/2005 | Taylor |
| 6,969,847 | B2 | 11/2005 | Davis |
| 7,090,333 | B2 | 8/2006 | Mutz et al. |
| 7,133,782 | B2 | 11/2006 | Odedra |
| 7,144,734 | B2 | 12/2006 | Court et al. |
| 7,169,560 | B2 | 1/2007 | Lapidus et al. |
| 7,179,423 | B2 | 2/2007 | Bohm |
| 7,183,406 | B2 | 2/2007 | Belshaw |
| 7,199,233 | B1 | 4/2007 | Jensen et al. |
| 7,262,031 | B2 | 8/2007 | Lathrop |
| 7,273,730 | B2 | 9/2007 | DuBreuil |
| 7,285,835 | B2 | 10/2007 | Rizzo et al. |
| 7,303,320 | B1 | 12/2007 | Ashley |
| 7,303,872 | B2 | 12/2007 | Sussman |
| 7,323,320 | B2 | 1/2008 | Oleinikov |
| 7,399,590 | B2 | 7/2008 | Piepenburg |
| 7,432,055 | B2 | 10/2008 | Pemov |
| 7,498,176 | B2 | 3/2009 | McCormick et al. |
| 7,537,897 | B2 | 5/2009 | Brenner et al. |
| 7,563,600 | B2 | 7/2009 | Oleinikov |
| 7,699,979 | B2 | 4/2010 | Li et al. |
| 7,723,077 | B2 | 5/2010 | Young et al. |
| 7,820,412 | B2 | 10/2010 | Belshaw et al. |
| 7,879,580 | B2 | 2/2011 | Can et al. |
| 7,932,025 | B2 | 4/2011 | Can |
| 8,053,191 | B2 | 11/2011 | Blake |
| 8,058,004 | B2 | 11/2011 | Oleinikov |
| 8,137,906 | B2 | 3/2012 | Schatz |
| 8,173,368 | B2 | 5/2012 | Staehler et al. |
| 8,338,091 | B2 | 12/2012 | Chesnut et al. |
| 8,476,018 | B2 | 7/2013 | Brenner |
| 8,716,467 | B2 | 5/2014 | Jacobson |
| 8,808,986 | B2 | 8/2014 | Jacobson |
| 9,023,601 | B2 | 5/2015 | Oleinikov |

(56) References Cited

U.S. PATENT DOCUMENTS

| | | |
|---|---|---|
| 9,023,649 B2 | 5/2015 | Mali et al. |
| 9,051,666 B2 | 6/2015 | Oleinikov |
| 9,150,853 B2 | 10/2015 | Hudson |
| 9,295,965 B2 | 3/2016 | Jacobson et al. |
| 9,322,037 B2 | 4/2016 | Liu et al. |
| 9,752,176 B2 | 9/2017 | Kung et al. |
| 2001/0012537 A1 | 8/2001 | Anderson et al. |
| 2001/0031483 A1 | 10/2001 | Sorge |
| 2001/0049125 A1 | 12/2001 | Stemmer |
| 2001/0053519 A1 | 12/2001 | Fodor et al. |
| 2002/0012616 A1 | 1/2002 | Zhou |
| 2002/0025561 A1 | 2/2002 | Hodgson |
| 2002/0037579 A1 | 3/2002 | Ellson et al. |
| 2002/0058275 A1 | 5/2002 | Fishel |
| 2002/0081582 A1 | 6/2002 | Gao |
| 2002/0127552 A1 | 9/2002 | Church |
| 2002/0132259 A1 | 9/2002 | Wagner |
| 2002/0132308 A1 | 9/2002 | Liu |
| 2002/0133359 A1 | 9/2002 | Brown |
| 2003/0017552 A1 | 1/2003 | Jarrell |
| 2003/0044980 A1 | 3/2003 | Mancebo |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri |
| 2003/0068633 A1 | 4/2003 | Belshaw |
| 2003/0068643 A1 | 4/2003 | Brennan |
| 2003/0082630 A1 | 5/2003 | Kolkman |
| 2003/0087298 A1 | 5/2003 | Green |
| 2003/0091476 A1 | 5/2003 | Zhou |
| 2003/0099952 A1 | 5/2003 | Green |
| 2003/0118485 A1 | 6/2003 | Singh-Gasson |
| 2003/0118486 A1 | 6/2003 | Zhou |
| 2003/0120035 A1 | 6/2003 | Gao |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer |
| 2003/0186226 A1 | 10/2003 | Brennan |
| 2003/0198948 A1 | 10/2003 | Stahler |
| 2003/0215837 A1 | 11/2003 | Frey |
| 2003/0215855 A1 | 11/2003 | Dubrow |
| 2003/0215856 A1 | 11/2003 | Church |
| 2003/0219781 A1 | 11/2003 | Frey |
| 2003/0224521 A1 | 12/2003 | Court et al. |
| 2004/0002103 A1 | 1/2004 | Short |
| 2004/0005673 A1 | 1/2004 | Jarrell |
| 2004/0009479 A1 | 1/2004 | Wohlgemuth et al. |
| 2004/0009520 A1 | 1/2004 | Albert |
| 2004/0014083 A1 | 1/2004 | Yuan |
| 2004/0053362 A1 | 3/2004 | De Luca et al. |
| 2004/0096891 A1 | 5/2004 | Bennett |
| 2004/0101444 A1 | 5/2004 | Sommers |
| 2004/0101894 A1 | 5/2004 | Albert |
| 2004/0101949 A1 | 5/2004 | Green |
| 2004/0106728 A1 | 6/2004 | McGall et al. |
| 2004/0110211 A1 | 6/2004 | McCormick |
| 2004/0110212 A1 | 6/2004 | McCormick |
| 2004/0126757 A1 | 7/2004 | Cerrina |
| 2004/0132029 A1 | 7/2004 | Sussman |
| 2004/0166567 A1 | 8/2004 | Santi |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang |
| 2004/0259146 A1 | 12/2004 | Friend |
| 2005/0053997 A1 | 3/2005 | Evans |
| 2005/0069928 A1 | 3/2005 | Nelson |
| 2005/0079510 A1 | 4/2005 | Berka et al. |
| 2005/0089889 A1 | 4/2005 | Ramsing et al. |
| 2005/0106606 A1 | 5/2005 | Parker |
| 2005/0112574 A1 | 5/2005 | Gamble et al. |
| 2005/0118628 A1 | 6/2005 | Evans |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Carr |
| 2005/0227316 A1 | 10/2005 | Santi et al. |
| 2005/0255477 A1 | 11/2005 | Carr |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0127920 A1 | 6/2006 | Church |
| 2006/0127926 A1 | 6/2006 | Belshaw |
| 2006/0134638 A1 | 6/2006 | Mulligan et al. |
| 2006/0160138 A1 | 7/2006 | Church |
| 2006/0194214 A1 | 8/2006 | Church |
| 2006/0281113 A1 | 12/2006 | Church et al. |
| 2006/0286678 A1 | 12/2006 | Dual et al. |
| 2007/0004041 A1 | 1/2007 | Church et al. |
| 2007/0122817 A1 | 5/2007 | Church et al. |
| 2007/0169227 A1 | 7/2007 | Cigan et al. |
| 2007/0231805 A1 | 10/2007 | Baynes |
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | van Eijk et al. |
| 2009/0087840 A1 | 4/2009 | Baynes et al. |
| 2009/0093378 A1 | 4/2009 | Bignell et al. |
| 2009/0137408 A1 | 5/2009 | Jacobson |
| 2009/0155858 A1 | 6/2009 | Blake |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0124767 A1 | 5/2010 | Oleinikov |
| 2010/0261158 A1 | 10/2010 | Nordman et al. |
| 2010/0273219 A1 | 10/2010 | May et al. |
| 2010/0311058 A1 | 12/2010 | Kim et al. |
| 2011/0052446 A1 | 3/2011 | Hirano et al. |
| 2011/0117625 A1 | 5/2011 | Lippow et al. |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0283110 A1 | 11/2011 | Dapkus et al. |
| 2011/0287490 A1 | 11/2011 | Coope et al. |
| 2012/0028843 A1 | 2/2012 | Ramu |
| 2012/0115756 A1 | 5/2012 | Williams et al. |
| 2012/0185965 A1 | 7/2012 | Senger et al. |
| 2012/0220497 A1 | 8/2012 | Jacobson |
| 2012/0270750 A1 | 10/2012 | Oleinikov |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson |
| 2012/0322681 A1 | 12/2012 | King |
| 2013/0005582 A1 | 1/2013 | Lower |
| 2013/0017977 A1 | 1/2013 | Oleinikov |
| 2013/0059296 A1 | 3/2013 | Jacobson |
| 2013/0059344 A1 | 3/2013 | Striedner et al. |
| 2013/0059761 A1 | 3/2013 | Jacobson |
| 2013/0085083 A1 | 4/2013 | Kamberov et al. |

(56) References Cited

U.S. PATENT DOCUMENTS

| | | | |
|---|---|---|---|
| 2013/0130347 A1 | 5/2013 | Delisa et al. |
| 2013/0163263 A1 | 6/2013 | Kouchi et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson |
| 2013/0252849 A1 | 9/2013 | Hudson et al. |
| 2013/0274135 A1 | 10/2013 | Zhang et al. |
| 2013/0281308 A1 | 10/2013 | Kung |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson |
| 2014/0295556 A1 | 10/2014 | Joung et al. |
| 2014/0309119 A1 | 10/2014 | Jacobson |
| 2015/0031089 A1 | 1/2015 | Lindstrom |
| 2015/0045234 A1 | 2/2015 | Stone et al. |
| 2015/0065393 A1 | 3/2015 | Jacobson |
| 2015/0191719 A1 | 7/2015 | Hudson |
| 2015/0203839 A1 | 7/2015 | Jacobson |
| 2015/0315547 A1 | 11/2015 | Oberg |
| 2015/0361420 A1 | 12/2015 | Hudson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0097051 A1 | 4/2016 | Jacobson et al. |
| 2016/0122755 A1 | 5/2016 | Hall et al. |
| 2016/0144332 A1 | 5/2016 | Chu |
| 2016/0144333 A1 | 5/2016 | Jacobson et al. |
| 2016/0168564 A1 | 6/2016 | Jacobson et al. |
| 2016/0215381 A1 | 7/2016 | Levine et al. |
| 2016/0250613 A1 | 9/2016 | Jacobson et al. |
| 2016/0326520 A1 | 11/2016 | Ramu et al. |
| 2017/0067805 A1 | 3/2017 | Horiba et al. |
| 2017/0137858 A1 | 5/2017 | Carr et al. |
| 2017/0144155 A1 | 5/2017 | Bohm et al. |
| 2017/0175110 A1 | 6/2017 | Jacobson et al. |
| 2017/0198268 A1 | 7/2017 | Jacobson et al. |
| 2017/0349925 A1 | 12/2017 | Jacobson et al. |
| 2018/0023120 A1 | 1/2018 | Kung et al. |

FOREIGN PATENT DOCUMENTS

| | | |
|---|---|---|
| CN | 101921840 | 12/2010 |
| DE | 4343591 | 6/1995 |
| EP | 259160 | 3/1988 |
| EP | 1015576 | 3/1999 |
| EP | 1159285 | 9/2000 |
| EP | 1180548 | 2/2002 |
| EP | 1314783 | 5/2003 |
| EP | 1411122 | 4/2004 |
| EP | 2017356 | 1/2009 |
| EP | 2175021 | 4/2010 |
| JP | 2005-538725 A | 12/2005 |
| JP | 2007-533308 A | 11/2007 |
| KR | 100491810 B1 | 10/2005 |
| WO | WO 199000626 | 1/1990 |
| WO | WO 1992/015694 A1 | 9/1992 |
| WO | WO 93/017126 | 9/1993 |
| WO | WO 1993/020092 | 10/1993 |
| WO | WO 94/018226 | 8/1994 |
| WO | WO 1995/017413 | 6/1995 |
| WO | WO 1996/033207 | 10/1996 |
| WO | WO 1996/034112 | 10/1996 |
| WO | WO 97/35957 | 10/1997 |
| WO | WO 1998/005765 | 2/1998 |
| WO | WO 98/020020 | 5/1998 |
| WO | WO 98/038326 | 9/1998 |
| WO | WO 1998/038299 | 9/1998 |
| WO | WO 1999/014318 | 3/1999 |
| WO | WO 99/019341 | 4/1999 |
| WO | WO 99/025724 | 5/1999 |
| WO | WO 1999/042813 | 8/1999 |
| WO | WO 1999/047536 | 9/1999 |
| WO | WO 00/049142 | 4/2000 |
| WO | WO 00/029616 | 5/2000 |
| WO | WO 2000/040715 | 7/2000 |
| WO | WO 00/046386 | 8/2000 |
| WO | WO 2000/053617 A1 | 9/2000 |
| WO | WO 2000/075368 | 12/2000 |
| WO | WO 01/088173 | 11/2001 |
| WO | WO 2001/081568 | 11/2001 |
| WO | WO 2001/085075 | 11/2001 |
| WO | WO 02/004597 | 1/2002 |
| WO | WO 02/081490 | 10/2002 |
| WO | WO 02/095073 | 11/2002 |
| WO | WO 02/101004 | 12/2002 |
| WO | WO 2003/010311 A2 | 2/2003 |
| WO | WO 03/033718 | 4/2003 |
| WO | WO 03/040410 | 5/2003 |
| WO | WO 2003/044193 | 5/2003 |
| WO | WO 03/046223 | 6/2003 |
| WO | WO 03/060084 | 7/2003 |
| WO | WO 03/064611 | 7/2003 |
| WO | WO 2003/054232 | 7/2003 |
| WO | WO 03/064026 | 8/2003 |
| WO | WO 03/064027 | 8/2003 |
| WO | WO 2003/064699 | 8/2003 |
| WO | WO 2003/065038 | 8/2003 |
| WO | WO 2003/066212 | 8/2003 |
| WO | WO 2003/083604 A2 | 10/2003 |
| WO | WO 2003/085094 | 10/2003 |
| WO | WO 2003/089605 A2 | 10/2003 |
| WO | WO 2003/100012 | 12/2003 |
| WO | WO 2004/002627 A2 | 1/2004 |
| WO | WO 2004024886 A2 | 3/2004 |
| WO | WO 04/034028 | 4/2004 |
| WO | WO 2004/029586 | 4/2004 |
| WO | WO 2004/031351 | 4/2004 |
| WO | WO 2004/031399 | 4/2004 |
| WO | WO 2004/090170 | 10/2004 |
| WO | WO 2005/059096 | 6/2005 |
| WO | WO 2005/071077 | 8/2005 |
| WO | WO 2005/089110 | 9/2005 |
| WO | WO 2005/103279 | 11/2005 |
| WO | WO 2005/107939 | 11/2005 |
| WO | WO 05/123956 | 12/2005 |
| WO | WO 2006076679 | 1/2006 |
| WO | WO 2006/031745 | 3/2006 |
| WO | WO 2006/044956 | 4/2006 |
| WO | WO 2006/049843 | 5/2006 |
| WO | WO 2006/086209 | 8/2006 |
| WO | WO 06/127423 | 11/2006 |
| WO | WO 07/008951 | 1/2007 |
| WO | WO 07/009082 | 1/2007 |
| WO | WO 2007/010252 | 1/2007 |
| WO | WO 07/075438 | 7/2007 |
| WO | WO 07/087347 | 8/2007 |
| WO | WO 07/117396 | 10/2007 |
| WO | WO 2007/113688 A2 | 10/2007 |
| WO | WO 2007/120624 | 10/2007 |
| WO | WO 07/123742 | 11/2007 |
| WO | WO 07/136833 | 11/2007 |
| WO | WO 07/136835 | 11/2007 |
| WO | WO 07/136840 | 11/2007 |
| WO | WO 2007/136736 | 11/2007 |
| WO | WO 2007/136834 | 11/2007 |
| WO | WO 08/024319 | 2/2008 |
| WO | WO 2008/027558 | 3/2008 |
| WO | WO 2008/041002 | 4/2008 |
| WO | WO 2008/045380 | 4/2008 |
| WO | WO 08/054543 | 5/2008 |
| WO | WO 08/076368 | 6/2008 |
| WO | WO 2008/109176 | 9/2008 |
| WO | WO 08/130629 | 10/2008 |
| WO | WO 2010/025310 A2 | 3/2010 |
| WO | WO 2010/070295 | 6/2010 |
| WO | WO 2010/115100 | 10/2010 |
| WO | WO 2010/115154 A1 | 10/2010 |
| WO | WO 11/053957 | 5/2011 |
| WO | WO 11/056872 | 5/2011 |
| WO | WO 11/066185 | 6/2011 |
| WO | WO 11/066186 | 6/2011 |
| WO | WO 11/085075 | 7/2011 |

(56) References Cited

FOREIGN PATENT DOCUMENTS

| WO | WO 11/143556 | 11/2011 |
| --- | --- | --- |
| WO | WO 11/150168 | 12/2011 |
| WO | WO 2011/161413 | 12/2011 |
| WO | WO 12/064975 | 5/2012 |
| WO | WO 12/078312 | 6/2012 |
| WO | WO 2012/084923 | 6/2012 |
| WO | WO 12/174337 | 12/2012 |
| WO | WO 2013/017950 A1 | 2/2013 |
| WO | WO 13/032850 | 3/2013 |
| WO | WO 13/163263 | 10/2013 |
| WO | WO 14/004393 | 1/2014 |
| WO | WO 2014/089290 A1 | 6/2014 |
| WO | WO 2014/093694 | 6/2014 |
| WO | WO 14/151696 | 9/2014 |
| WO | WO 2014/144288 A1 | 9/2014 |
| WO | WO 14/160004 | 10/2014 |
| WO | WO 14/160059 | 10/2014 |
| WO | WO 2014/191518 A1 | 12/2014 |
| WO | WO 15/017527 | 2/2015 |
| WO | WO 2015/035162 A2 | 3/2015 |
| WO | WO 15/081114 | 6/2015 |

OTHER PUBLICATIONS

Aihara, H., et al. "A Conformational Switch Controls the DNA Cleavage Activity of a Integrase," Molecular Cell, 12: 187-198, (Jul. 2003).

Akhundova A.A. et al. "RNA synthesis on immobilized DNA templates in vitro." Biochemistry—Moscow, 43(5):626-628 (1978).

Altschul, S. & Koonin, E. "Iterated profile searches with PSI-BLAST—a tool for discovery in protein databases," Trends Biochem. Sci., 23:444-447, (1998).

Altschul, S., et al. "Basic local alignment search tool," J Mol Biol., 215(3):403-10, (1990).

Andersen, J., et al. "New Unstable Variants of Green Fluorescent Protein for Studies of Transient Gene Expression in Bacteria," Applied and Environmental Microbiology, 64(6):2240-2246 (Jun. 1998).

Ashkin, A., Applications of laser radiation pressure Science, 210(4474): 1081-1088, (Dec. 5, 1980).

Aslanzadeh, Brief Review: Preventing PCR Amplification Carry-over Contamination in a Clinical Laboratory. Annals of Clinical & Laboratory Science 34(4) :389 (2004).

Au, L., et al. Gene Synthesis by a LCR-Based Approach: High-Level Production of Leptin-L54 Using Synthetic Gene in *Escherichia coli*, Biochemical and Biophysical Research Communications, 248:200-203 (1998).

Babineau et al. The FLP Protein of the 2 micron Plasmid of Yeast (1985) J. Biol. Chem. 260: 12313-12319.

Bar G., et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).

Bartsevich, V., et al. "Engineered Zinc Finger Proteins for Controlling Stem Cell Fate," Stem Cells, 21:632-637 (2003).

Beer, et al., On-chip, real time single-copy polymerase chain reaction in picoliter droplets, Analytical Chemistry, 79(22):8471-8475, (Nov. 15, 2007).

Beier M. and Hohseil J.D. "Analysis of DNA-microarray produced by inverse in situ oligonucleotide synthesis." J. Biotechnology, 94:15-22 (2002).

Bennett, Solexa Ltd., Pharmacogenomics, 5(4):433-8, (Jun. 2004).

Berlin Y. A. DNA splicing by directed ligation (SDL), Current Issues Molec. Biol. 1:21-30, 1999.

Bethell, D., et al. From monolayers to nanostructured materials: an organic chemist's view of self-assembly, J. Electroanal. Chem., 409:137-143, (1996).

Binkowski et al. Correcting errors in synthetic DNA through consensus shuffling Nucl. Acids Res., vol. 33, No. 6, e55, 2005.

Blanchard, A., "Synthetic DNA Arrays," Genetic Engineering, vol. 20, pp. 111-123, Plenum Press, (1998).

Boal et al. Cleavage of oligodeoxyribonucleotides from controlled-pore glass supports and their rapid deprotection by gaseous amines, NAR, 24(15):3115-3117, (1996).

Boltner, D., et al. "R391: A Conjugative Integrating Mosaic Comprised of Phage, Plasmid, and Transposon Elements," J. of Bacteriology, 184(18):5158-5169 (Sep. 2002).

Booth, P.M., et al. "Assembly and cloning of coding sequences for neurotrophic factors directly from genomic DNA using polymerase chain reaction and uracil DNA glycosylase," Gene 146:303-308 (1994).

Braatsch et al., *Escherichia coli* strains with promoter libraries constructed by Red/ET recombination pave the way for transcriptional fine-tuning, Biotechniques. 2008;45(3):335-337.

Brown, Chappell "BioBricks to help reverse-engineer life," URL: http://eetimes.com/news/latest/showArticle.ihtml?articleiD=21700333 (Jun. 11, 2004).

Burge et al., Prediction of complete gene structures in human genomic DNA, J Mol Biol., 268(1):78-94, (1997).

Cai, Q., et al. Immunogenicity of Polyepitope Libraries Assembled by Epitope Shuffling: An Approach to the Development of Chimeric Gene Vaccination Against Malaria, Vaccine, 23:267-277, (2004).

Carr, P., et al. "Protein-mediated error-correction for de novo DNA synthesis," Nucleic Acids Research, 32(20), e162 (9 pages), (2004).

Caruthers et al. CXV. Total synthesis of the structural gene for an alanine transfer RNA from yeast. Enzymic joining to form the total DNA duplex J Mol Biol. Dec. 28, 1972;72(2):475-92.

Cassell et al., Mechanism of Inhibition of Site-specific Recombination by the Holliday Junction-trapping Peptide WKHYNY: Insights into Phage I integrase-mediated Strand Exchange, J. Mol. Biol., 327:413-429, (2003).

Chakrabarti et al., Novel Sulfoxides facilitate GC-rich template amplification., 2002, BioTechniques 32(4):866-873.

Chalmers, F.P., et al. "Scaling Up the Ligase Chain Reaction-Based Approach to Gene Synthesis" BioTechniques 30:249-252 (2001).

Chan, L. et al. "Refactoring bacteriophage T7," Molecular Systems Biol., doi: 10.1038/msb4100025, (Published online Sep. 13, 2005).

Chandrasegaran, S., et al. "Chimeric Restriction Enzymes: What is Next?," Biol. Chem., 380:841-848 (1999).

Chang, C., et al. "Evolution of a cytokine using DNA family shuffling," Nature Biotechnology, 17: 793-797(1999).

Che, A. "BioBricks++: Simplifying Assembly of Standard DNA Components," [Online] XP002412778, URL:http://austinche.name/docs/bbpp.pdf (Jun. 9, 2004).

Chen, H.B., et al. "A new method for the synthesis of a structural gene," Nucleic Acids Research 18(4):871-878 (1990).

Cherepanov A "Joining of short DNA oligonucleotides with base pair mismatches by T4 DNA ligase" J Biochem. Jan. 2001;129(1):61-8.

Chetverin et al., Sequencing pool of Nucleic Acids on Oligonucleotide arrays, Biosystems, 30:215-231, (1993).

Chevalier et al., Homing endonucleases: structural and functional insight into the catalysts of intron/intein mobility, Nucl. Acids Res., 29(18):3757-3774 (2001).

Chevalier, B., et al. Design, Activity, and Structure of a Highly Specific Artificial Endonuclease, Molecular Cell, 10:895-905 (Oct. 2002).

Cho et al. Creating, transporting, cutting and merging liquid droplets by electrowetting-based actuation for digital microfluidic circuits, J. of Microelectromechanical Systems, 12(1):70-80, (Feb. 2003).

Christians, F., et al. "Directed evolution of thymidine kinase for AZT phosphorylation using DNA family shuffling," Nature Biotechnology, 17:259-264(1999).

Coco, W., et al. "Growth Factor Engineering by Degenerate Homoduplex Gene Family Recombination," Nature Biotechnology, 20: 1246-1250, (Dec. 2002).

Colvin, V., et al. Semiconductor nanocrystals covalently bound to metal surfaces with self-assembled monolayers, J. Am. Chem. Soc., 114(13):5221-5230, 1992.

Crameri, A, et al. "DNA shuffling of a family of genes from diverse species accelerates directed evolution," Nature, 391:288-291(1998).

(56) References Cited

OTHER PUBLICATIONS

Crameri, A, et al. "Improved Green Fluorescent Protein by Molecular Evolution Using DNA Shuffling," Nature Biotechnology, vol. 14, Mar. 1996, pp. 315-319.
Crameri, A, et al. "Molecular evolution of an arsenate detoxification pathway by DNA shuffling," Nature Biotechnology, 15:436-438 (1997).
Cui T. et al. Sepharose-supported DNA as template for RNA synthesis J. Biotechnology, 66: 225-228 (1998).
Dafhnis-Calas, F., et al. "Iterative in vivo assembly of large and complex transgenes by combining the activities of <DC31 integrase and Cre recombinase," Nucleic Acids Research, 33(22): 1-14 (2005).
Datsenko K.A. et al. One-step inactivation of chromosomal genes in Escherichia coli K-12 using PCR products PNAS (2000) 97: 6640-6645.
Dedkova, L. et al. Enhanced D-Amino Acid Incorporation into Protein by modified Ribosomes, J. Am. Chem. Soc., 125:6616-6617, (2003).
Demeler et al. Neural network optimization for E. coli promoter prediction, Nucl. Acids. Res. 19:1593-1599 (1991).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. Jan. 2011;8(1):74-9. doi:10.1038/nmeth.1539. Epub Dec. 5, 2010.
Duggan, D., et al., "Expression profiling using cDNA microarrays," Nat. genet., vol. 21, pp. 10-14, (Jan. 1999).
Ellson, Picoliter: Enabling Precise Transfer of Nanoliter and Picoliter Volumes. Drug Discovery Today 7(5 Suppl.) :s32 (2002).
Elowitz et al., A synthetic oscillatory network of transcriptional regulators. Nature. 2000;403;335-338.
Engler C. et al. A one pot, one step, precision cloning method with high throughput capability PLoS One, 3: e36471.
Engler C. et al. Golden Gate Shuffling: a one-pot DNA shuffling method based on type IIS restriction enzymes PLoS One, 4:e5553, 2009.
Evans, E. & Alani, E. "Roles for Mismatch Repair Factors in Regulating Genetic Recombination," Molecular & Cellular Biology, 20(21):7839-7844 (Nov. 2000).
Ferretti, L. et al. "Total synthesis of a gene for bovine rhodopsin," PNAS, 83:599-603 (Feb. 1986).
Ferrin, L.J., et al. "Sequence-specific ligation of DNA using RecA protein," Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling for Making Large Peptide Repertoires Displayed on Filamentous Bacteriophage, Proceedings of the National Academy of Sciences of USA, 93:7761-7766, (Jul. 1996).
Flanagan et al. Analysis of inhibitors of the site-specific recombination reaction mediated by Tn3 resolvase (1989) J. Mol. Biol. 206: 295-304.
Fleck, O. & Nielsen O. "DNA Repair," J. Cell Science, 117:515-517 (2004).
Fodor et al., Light-directed, spatially addressable parallel chemical synthesis, Science, 251(4995):767-773, (Feb. 15, 1991).
Fujita et al., Surprising liability of biotin-streptavidin bond during transcription of biotinylated DNA bound to paramagnetic streptavidin beads. Bio Techniques, 14:608-617 (1993).
Fullwood et al., Next-generation DNA sequencing of paired-end tags (PET) for transcriptome and genome analyses. Genome Res. Apr. 2009;19(4):521-32. doi: 10.1101/gr.074906.107.
Gabsalilow et al., Site- and strand-specific nicking of DNA by fusion proteins derived from MutH and I-SceI or TALE repeats. Nucleic Acids Res. Apr. 2013;41(7):e83. doi: 10.1093/nar/gkt080. Epub Feb. 13, 2013.
Gao, X. et al. "Thermodynamically balanced inside-out (TBIO) PCR-based gene synthesis: a novel method of primer design for high fidelity assembly of longer gene sequences," Nucleic Acids Research, 31(22):e143 (11 pages) (2003).
Gardner, T., et al. "Construction of a genetic toggle switch in Escherichia coli," Nature, 403:339-342 (Jan. 2000).
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Gibbs, W. "Synthetic Life," Scientific American, [Online] URL: htto://www.sciam.com/orintversion.cfm?articleiD=0009FCA4, (Apr. 26, 2004).
Glasgow A.C. et al. DNA-binding properties of the Hin recombinase (1989) J. Biol. Chem. 264: 10072-10082.
Goler, J. "BioJADE: A Design and Simulation Tool for Synthetic Biological Systems," MIT Compute rScience and Artificial Intelligence Laboratory, AI Technical Report, [Online] URL: http://dspace.mit.edu/bitstream/1721.1/30475/2/MIT-CSAIL-TR-2004-036.pdf, (May 2004).
Grabar, K., et al., Preparation and Characterization Monolayers, Anal. Chem., 67:735-743, (1995).
Greenberg et al., Cleavage of oligonucleotides from solid-phase support using o-nitrobenzyl photochemistry, J. of Org. Chem., 59(4):746-753, (Feb. 1994).
Grifith et al., Coordinating Multiple Droplets in Planar Array Digital Microfluidic Systems, The International Journal of Robotics Research, 24(11):933-949, (Nov. 2005).
Gronostajski et al., The FLP protein of the 2 micron plasmid of yeast (1985) J. Biol. Chem. 260: 12328-12335.
Guilinger et al., Fusion of catalytically inactive Cas9 to FokI nuclease improves the specificity of genome modification. Nat Biotechnol. Jun. 2014;32(6):577-582. doi: 10.1038/nbt.2909. Epub Apr. 25, 2014.
Gulati Shelly et al. "Opportunities for microfluidic technologies in synthetic biology" Journal of Royal Society, vol. 6, pp. S493-S506, 2009.
Guntas, G., et al. "Directed Evolution of Protein Switches and Their Application to the Creation of Ligand-Binding Proteins," Proc. Natl. Acad. Sci. USA, 102(32):11224-11229 (Aug. 9, 2005).
Guntas, G., et al. A molecular switch created by in vitro recombination of nonhomologous genes, Chem. & Biol., 11:1483-1487 (Nov. 2004).
Gupta, N., et al. Studies on Polynucleotides, LXXXVIII. Enzymatic Joining of Chemically Synthesized Segments Corresponding to the Gene for Alanine-tRNA, PNAS, 60:1338-1344, (1968).
Hacia J.G. "Resequencing and mutational analysis using oligonucleotide microarrays", Nature Genetics, 21(1 suppl):42-47, 1999.
Hacia J.G. et al. "Applications of DNA chips for genomic analysis". Mol Psychiatry. Nov. 1998;3(6):483-92.
Haeberle et al., Microfluidic platforms for lab-on-chip applications, Lab on a Chip 7(9):1094-1110, (2007).
Haffter et al. Enhancer independent mutants of the Cin recombinase have a relaxed topological specificity. (1988) EMBO J. 7:3991-3996.
Hansen, W. & Kelley M. "Review of Mammalian DNA Repair and Transcriptional Implications," J. Pharmacol. & Exper. Therapeutics, 295(1): 1-9, (2000).
Hardy et al., Reagents for the preparation of two oligonucleotides per synthesis (TOPSTM), Nucleic Acids Research, 22(15):2998-3004, (1994).
Hawley et al., Compilation and analysis of Escherichia coli promoter DNA sequences Nucl. Acid. Res. 11:2237-2255. 1983.
Hecker, K.H., et al. "Error Analysis of chemically Synthesized Polynucleotides," BioTechniques, 24:256-260 (1998).
Heeb, S., et al. Small, Stable Shuttle Vectors Based on the Minimal pVS1 Replicon for Use in Gram-Negative Plant-Associated Bacteria, MPMI, 13(2):232-237 (2000).
Henegariu et al. Multiplex PCR: critical parameters and step-by-step protocol Biotechniques, 23(3): 504-511, (Sep. 1997).
Hermeling, S., et al. "Structure-Immunogenicity Relationships of Therapeutic Proteins," Pharmaceutical Research, 21(6): 897-903, (Jun. 2004).

(56) References Cited

OTHER PUBLICATIONS

Higuchi, R., et al. A general method of in vitro preparation and specific mutagenesis of DNA fragments: study of protein and DNA interactions, Nucleic Acids Research, 16(15):7351-7367 (1988).
Hoess et al., Mechanism of strand cleavage and exchange in the Cre-lox site-specific recombination system (1985) J. Mol. Biol. 181: 351-362.
Hoess R.H. et al. Interaction of the bacteriophage P 1 recombinase Cre with the recombining site loxP (1984) Proc. Natl. Acad. Sci. USA 81: 1026-1029.
Hoess R.H. et al. P 1 site-specific recombination: nucleotide sequence of the recombining sites (1982) Proc. Natl. Acad. Sci. USA 79: 3398-3402.
Hoess R.H. et al. The role of the loxP spacer region in PI site-specific recombination (1986), Nucleic Acids Res. 14: 2287-2300.
Holmes, Model studies for new o-nitrobenzyl photolabile linkers: substituent effects on the rates of photochemical cleavage, J. of Org. Chem., 62(8):2370-2380, (Apr. 18, 1997).
Hoover et al., DNAWorks: an automated method for designing oligonucleotides for PCR-based gene synthesis, Nucleic Acids Research, 30(10):e43 (7 pages), (2002).
Horton, R., et al. Engineering hybrid genes without the use of restriction enzymes: Gene splicing by overlap extension, Gene, 77:61-68, (1989).
Hyman, A new method of sequencing DNA, Analytical Biochemistry, 174(2):423-436, (Nov. 1, 1988).
Ibrahim, E., et al. Serine/arginine-rich protein-dependent suppression of exon skipping by exonic splicing enhancers, Proc. Natl. Acad. Sci. U S A, 102(14):5002-5007, (Apr. 5, 2005).
International Search Report and Written Opinion in International Application No. PCT/US2011/060217 dated Feb. 4, 2012.
Ito Ret al. "Novel muteins of human necrosis factor alpha" Biochimica Biophysica Acta (1991), vol. 1096, pp. 245-252.
Jayaraman K. et al. "Polymerase chain reaction-mediated gene synthesis: synthesis of a gene coding for isozyme c of horseradish peroxidase." Proc Natl Acad Sci US A. May 15, 1991; 88(10): 4084-4088.
Jayaraman, et al. A PCR-mediated Gene synthesis strategy involving the assembly of oligonucleotides representing only one of the strands, Biotechniques, 12(3):392-398, (1992).
Jensen P.R. et al. The sequence of spacers between the consensus sequences modulates the strength of prokaryotic promoters Appl. Env. Microbiol. 64:82-87, 1998.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Johnston M. "Gene chips: Array of hope for understanding gene regulation". Current Biology, 8: (5) R171, 1998.
Jones, T., et al. "The Development of a Modified Human IFN-alpha2b Linked to the Fe Portion of Human IgG1 as a Novel Potential Therapeutic for the Treatment of Hepatitis C Virus Infection," Journal of Interferon & Cytokine Research, 24:560-572, (2004).
Kahl et al. Solution-Phase Bioconjugate Synthesis Using Protected Oligonucleotides Containing 3'-Alkyl Carboxylic Acids, J. of Org. Chem., 64(2):507-510, (1999).
Kahl et al., High-Yielding Method for On-col. Derivatization of Protected Oligodeoxy-nucleotides and Its Application to the Convergent Synthesis of 5',3'-Bis-conjugates, J. of Org. Chem., 63(15):4870-4871.
Kampke T. "Efficient primer design algorithms" Bioinformatics, 2001, vol. 17, No. 3, pp. 214-225.
Kelly et al., Miniaturizing chemistry and biology in microdroplets, Chem. Commun., 1773-1788, (2007).
Khaitovich, P., et al. Characterization of functionally active subribosomal particles from Thermus aquaticus, Proc. Natl. Acad. Sci., 96:85-90 (Jan. 1999).
Khnouf, R. et al, Cell-free protein expression in a microchannel array with passive pumping, Lab Chip, 9: 56-61 (2009).
Kim et al., Precision genome engineering with programmable DNA-nicking enzymes. Genome Res. Jul. 2012;22(7):1327-33. doi:10.1101/gr.138792.112. Epub Apr. 20, 2012.
Kim J.H. et al. "Solid-phase genetic engineering with DNA immobilized on a gold surface." J. Biotechnology, 2002, 96:213-22.
Kim, C., et al. "Biological lithography: Improvements in DNA synthesis methods," J. Vac. Sci. Technol. B 22(6):3163-3167 (2004).
Kim, Y., et al. "Insertion and Deletion Mutants of FokI Restriction Endonuclease," J. Biol. Chem., 269(50):31978-31982 (1994).
Kinde et al., Detection and quantification of rare mutations with massively parallel sequencing. Proc Natl Acad Sci USA. Jun. 7, 2011;108(23):9530-5. doi: 10.1073/pnas.1105422108. Epub May 17, 2011. Supplemental Information.
Kisselev, L., et al. "Termination of translation: interplay of mRNA, rRNAS and release factors?," The EMBO J., 22(2): 175-182, (2003).
Kitamura, K., et al. "Construction of Block-Shuffled Libraries of DNA for Evolutionary Protein Engineering: Y-Ligation-Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kodumal., S., et al. Total synthesis of long DNA sequences: Synthesis of a contiguous 32-kb polyketide synthase gene cluster, PNAS, 101(44):15573-15578, (Nov. 2, 2004).
Kolisnychenko, V., et al. "Engineering a Reduced *Escherichia coli* Genome," Genome Research, 12:640-647, (2002).
Kong et al., Parallel gene synthesis in microfluidic device, Nucleic Acids Research, vol. 35, No. 8, pp. e61-1 (9 pages), (2007).
Kosuri et al. (Scalable gene synthesis by selective amplification of DNA pools from high-fidelity microchips, Nature Biotechnology 28, 1295-1299 (2010), Published online Nov. 28, 2010).
Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "In vitro reconstitution of homologous recombination reactions," Experientia, 50:204-215,(1994).
Kowalczykowski, S. "Initiation of genetic recombination and recombination-dependent replication," TIBS, 25:156-165, (Apr. 2000).
Krieg a "Real-time detection of nucleotide incorporation during complementary DNA strand analysis" Chem. Bio. Chem. 4:589-592 (2003).
Kurian et al. "DNA chip technology". J Pathol. Feb. 1999; 187(3):267-71.
Lamers, M., et al. ATP Increases the Affinity between MutS ATPase Domains, J. Biol. Chem., 279(42):43879-43885, (Oct. 15, 2004).
Lashkari et al. "An automated multiplex oligonucleotide synthesizer: Development of high throughpout, low cost DNA synthesis". 1995, PNAS 92(17): 7912-7915.
Leamon et al., A massively parallel PicoTiterPlate.TM. based platform for discrete picoliter-scale polymerase chain reactions, Electrophoresis, 24(21):3769-3777, (Nov. 2003).
Lebedenko E.N. et al. Method of artificial DNA splicing by directed ligation Nucleic Acids Research, 19: 6757-6761, 1991.
Lederman et al., DNA-directed peptide synthesis. 1. A comparison of T2 and *Escherichia coli* DNA-directed peptide synthesis in two cell-free systems. Biochim Biophys Acta. Nov. 21, 1967;149(1):253-8.
Lee, K., et al. "Genetic approaches to Studying Protein Synthesis: Effects of Mutations at .PSI.I516 and A535 in *Escherichia coli* 16S rRNA," J. Nutr., 131:2994S-3004S, (2001).
Leslie et al., Site-specific recombination in the replication terminus region of *Escherichia coli*: functional replacement of dif. (1995) EMBO J. 14: 1561-1570.
Lewis et al. Gene modification via plug and socket gene targeting. J Clin Invest. Jan. 1, 1996;97(1):3-5.
Lewis et al., Control of directionality in integrase-mediated recombination: examination of recombination directionality factors (RDFs) including Xis and Cox proteins, Nucl. Acids Res., 29(11):2205-2216 (2001).

(56) References Cited

OTHER PUBLICATIONS

Li L et al. "Alteration of the cleavage distance of Fok I restriction endonuclease by insertion mutagenesis." Proc Natl Acad Sci USA. 90(7): 2764-2768 (Apr. 1993).
Li, C., and Evans, R. "Ligation independent cloning irrespective of restriction site compatibility," Nucl. Acids Res., 25(20):4165-4166 (1997).
Link, A., et al. "Methods for generating precise deletions and insertions in the genome of wild-type *Escherichia coli*: Application to open reading frame characterization," J. Bacteriol., 179(20):6228-6237, (Oct. 1997).
Liu et al., DNA ligation of ultramicrovolume using EWOD microfluidic system with coplanar electrodes: DNA ligation of ultramicrovolume using a EWOD microfluidic system, J. of Micromechanics and Microengineering, 18(4):45017 (7 pages), (2008).
Liu G. et al. "DNA computing on surfaces." Nature, 403:175179 (2000).
Liu, W. et al. "Genetic Incorporation of Unnatural Amino Acids Into Proteins in Mammalian Cells," Nature Methods, 4(3):239-244, (Mar. 2007).
Lu et al., Conjugative transposition: Tn916 integrase contains two independent DNA binding domains that recognize different DNA sequences '(1994) EMBO J. 13: 1541-1548.
Luo, P., et al. "Development of a Cytokine Analog with Enhanced Stability Using Computational Ultrahigh Throughput Screening," Protein Science, 11:1218-1226, (2002).
Lutz, S. & Benkovic, J. "Homology-Independent Protein Engineering," Current Opinion in Biotechnology, 11:319-324, (2000).
Mandecki et al. FokI method of gene synthesis Gene, 68:101-107 (1988).
Mandecki W. "Oligonucleotide-directed double-strand break repair in plasmids of *Escherichia coli*: A method for site-specific mutagnenesis." 1986, PNAS, 83:7177-7181.
Mannervik, B. "Optimizing the Heterologous Expression of Glutathione Transferase," Methods in Enzymology, 401:254-265, (2005).
Margulies et al., Genome Sequencing in Microfabricated High-Density Picolitre Reactors, Nature. 437: 376-380 (2005). Supplemental materials.
Matzas et al. (High-fidelity gene synthesis by retrieval of sequence-verified DNA identified using high-throughput pyrosequencing, Nature Biotechnology 28, 1291-1294 (2010), Published online Nov. 28, 2010).
McCaughan et al., Single-Molecule Genomics, The Journal of Pathology, 220: 297-306, (Jan. 1, 2009).
McClain et al., Genome Sequence Analysis of Helicobacter Pylori Strains Associated with Gastric Ulceration and Gastric Cancer, BMC Genomics, Biomed Central Ltd, London, IK. 10(1):3 (2009).
McGall et al., Light-Directed Synthesis of High-Density Oligonucleotide Arrays Using Semiconductor Photoresists, Pro. Natl. Acad. Sci. 93(24):13555-13560 (1996).
Mei et al., "Cell-Free Protein Synthesis in Microfluidic Array Devices," Biotechnol. Prog. 2007, 23:1305-1311.
Mercier, J. et al. Structural and functional characterization of tnpI, a recombinase locus in Tn21 and related beta-lactamase transposons. (1990) J. Bacteriol. 172: 3745.
Metzker et al., Termination of DNA synthesis by novel 3'-modified-deoxyribonucleoside 5'-triphosphates, Nar, 22(20):4259-4267, (1994).
Metzker, Emerging technologies in DNA sequencing. Genome Res. Dec. 2005;15(12):1767-76.
Meyer-Leon et al. Purification of the FLP site-specific recombinase by affinity chromatography and reexamination of basic properties of the system (1987) Nucleic Acids Res. 15: 6469.
Mezard, C., et al. "Recombination Between Similar But Not Identical DNA Sequences During Yeast Transformation Occurs Within Short Stretches of Identity," Cell, 70:659-670, (Aug. 21, 1992).
Miick, S., et al. "Crossover isomer bias is the primary sequence-dependent property of immobilized Holliday junctions," Proc. Natl. Acad. Sci. USA, 94:9080-9084, (Aug. 1997).

Milton, R., et al. "Total Chemical Synthesis of a D-Enzyme: The Enantiomers ofHIV-1 Protease Show Demonstration of Reciprocal Chiral Substrate Specificity," Science, 256:1445-1448, (Jun. 5, 1992).
Mir K. U. et al. Sequencing by cyclic ligation and cleavage (CycLic) directly on a microarray captured template. Nucl. Acids Rse. vol. 37, No. 1 e5, 2008.
Mitra R.D. et al. "Fluorescent in situ sequencing on polymerase colonies." Analytical Biochemistry, 320: 55-65 (2003).
Modrich, P. "Strand-specific Mismatch Repair in Mammalian Cells," J. Biol. Chem., 272(40): 24727-24730, (Oct. 3, 1997).
Moffitt et al., Recent Advances in Optical Tweezers. Annual Review of Biochemistry 77 :205 (Feb. 2008).
Moore, G. & Maranas C. "Computational Challenges in Combinatorial Library Design for Protein Engineering," AIChE Journal, 50(2):262-272, (Feb. 2004).
Morton, Oliver "Life, Reinvented," Wired, http:www.wired.com/wired/archive!13.01/mit_pr.html (2005).
Muller, Ten years of gene targeting: targeted mouse mutants, from vector design to phenotype analysis. Mech Dev. Apr. 1999;82(1-2):3-21.
Nakamaye, K., et al. "Direct sequencing of polymerase chain reaction amplified DNA fragments through the incorporation of deoxynucleoside alpha-thiotriphosphates," Nucleic Acids Research, 16(21):9947-9959, (1988).
Nakamura, Y. & Ito, K. "How protein reads the stop codon and terminates translation," Genes to Cells, 3:265-278, (1998).
Nakayama et al., A system using convertible vectors for screening soluble recombinant proteins produced in *Escherichia coli* from randomly fragmented cDNAs, Bioch. and Biophys. Res. Comm., 312:825-830, (2003).
Ness, J., et al. "DNA shuffling of subgenomic sequences of subtilisin," Nature Biotechnology 17: 893-896 (1999).
Ness, J., et al. "Synthetic Shuffling Expands Functional Protein Diversity by Allowing Amino Acids to Recombine Independently" Nature Biotechnology, 20:1251-1255, (Dec. 2002).
Neuman et al., Optical trapping. Rev Sci Instrum. Sep. 2004;75(9):2787-809.
Nilsson P. et al. "Real-Time monitoring of DNA manipulations using biosensor technology" Analytical Biochemistry, 1995, 224:400-408.
Nilsson, L., et al. "Improved Heterologous Expression of Human Glutathione Transferase A4-4 by Random Silent Mutagenesis of Codons in the 5' Region," Biochemica et Biophysica Acta, 1528: 101-106, (2001).
Noirot et al., DNA Strand Invasion Promoted by *Escherichia coli* RecT Protein, J. Biol. Chem., 273(20):12274-12280, (May 15, 1998).
Novy, R., et al. "Ligation Independent Cloning: Efficient Directional Cloning of PCR Products," Novagen, Inc., InNovations, 5: 1-3, http://www.emdbiosciences.com/html/NVG/inNovations. html), (1996).
Orban P.C. et al. Tissue- and site-specific DNA recombination in transgenic mice (1992) Proc. Natl. Acad. Sci. 89: 6861-6865.
Osawa, S., et al. "Recent Evidence for Evolution of the Genetic Code," Microbiological Reviews, 56(1):229-264, (Mar. 1992).
Osborn et al., When phage, plasmids, and transposons collide: genomic islands, and conjugative and mobilizable-transposons as a mosaic continuum, Plasmid, 48:202-212, (2002).
Pachuk C.J. et al. Chain reaction cloning: one step method for directional ligation of multiple DNA fragments Gene, 243(1-2): 19-25 (2000).
Padgett et al .. Creating seamless junctions independent of restriction sites in PCR cloning, Gene, Feb. 2, 1996, vol. 168, No. 1, pp. 31-35.
Pan et al., An approach for global scanning of single nucleotide variations, PNAS, 99(14):9346-9351, (Jul. 9, 2002).
Panet A. and Khorana G.H. "Studies of polynucleotides: the linkage of deoxyribopolynucleotides templates to cellulose and its use in their replication." J. Biol. Chem. 249(16):5213-5221 (1974).
Parr, R. & Ball, J. "New donor vector for generation of histidine-tagged fusion proteins using the Gateway Cloning System," Plasmid, 49:179-183, (2003).

(56) References Cited

OTHER PUBLICATIONS

Pemov et al., DNA analysis with multiplex microarray-enhanced PCR. Nucleic Acids Res. Jan. 20, 2005;33(2):e11.
Peters, J. & Craig, N. "Tn7: Smarter Than We Thought," Nature, 2:806-814, (Nov. 2001).
Petrik et al., Advances in Transfusion Medicine in the First Decade of the 21st Century: Advances in Miniaturized Technologies, Transfusion and Apheresis Science. 45(1): 45-51 (2011).
Pon, Solid-phase supports for oligonucleotide synthesis, Methods Mol. Biol., 20:465-496, (1993).
Posfai, G., et al. "In vivo excision and amplification of large segments of the *Escherichia coli* genome," Nucl. Acids Res., 22(12):2392-2398, (1994).
Posfai, G., et al. "Markerless gene replacement in *Escherichia coli* stimulated by a double-strand break in the chromosome," Nucl. Acids Res., 27(22):4409-4415, (1999).
Prodromou et al., Recursive PCR: A Novel Technique for Total Gene Synthesis Protein Engineering, 5(8):827-829 (1992).
Ramachandran et al., End-Point Limiting-Dilution Real-Time PCR Assay for Evaluation of Hepatitis C Virus Quasispecies in Serum: Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Randegger et al., Real-time PCR and melting curve analysis for reliable and rapid detection of SHV extended-spectrum beta-lactamases. Antimicrob Agents Chemother. Jun. 2001;45(6):1730-6.
Regalado, A. "Next Dream for Venter: Create Entire Set of Genes From Scratch," Wall Street Journal, A1, (Jun. 29, 2005).
Reyrat, J., et al. Counterselectable Markers: Untapped Tools for Bacterial Genetics and Pathogenesis, Infection and Immunity, 66(9):4011-4017, (Sep. 1998).
Richmond, K., et al., Amplification and assembly of chip-eluted DNA (AACED): a method for high-throughput gene synthesis, Nucleic Acids Research, 32(17): 5011-5018 (2004).
Roberts et al., RNA-peptide fusions for the in vitro selection of peptides and proteins, Proc Natl Acad Sci USA. 94(23): 12297-302, 1997.
Rouillard, J. et al. Gen2Oligo: Oligonucleotide design for in vitro gene synthesis, Nucleic Acids Research, 32: W176-W180, (2004).
Rouwendal, G., et al. "Enhanced Expression in Tobacco of the Gene Encoding Green Fluorescent Protein by Modification of its Codon Usage," Plant Molecular Biology, 33:989-999, (1997).
Ryu, D.D.Y., et al. "Recent Progress in Biomolecular Engineering," Biotechnol. Prog. 16: 2-16 (2000).
Sa-Ardyen, P., et al. The flexibility of DNA double crossover molecules, Biophys. J., 84:3829-3837, (Jun. 2003).
Saha et al., The promoter of the Chinese hamster ovary dihydrofolate reductase gene regulates the activity of the local origin and helps define its boundaries. Genes Dev. Feb. 15, 2004;18(4):397-410. Epub Feb. 20, 2004.
Saiki, R., et al. "Analysis of enzymatically amplified beta-globin and HLA-DQ alpha DNA with allele-specific oligonucleotide probes," Nature, 324(6093):163-166, (Nov. 13, 1986).
Sakabe, N., et al. "A Bioinformatics Analysis of Alternative Exon Usage in Human Genes Coding for Extracellular Matrix Proteins," Genetics and Molecular Research, 3(4):532-544, (2004).
Sakamoto, K., et al. "Site-Specific Incorporation of an Unnatural Amino Acid Into Proteins in Mammalian Cells," Nucleic Acids Research, 30(21):4692-4699, (2002).
Saks, M. "Making sense out of nonsense," PNAS, 98(5): 2125-2127, (Feb. 27, 2001).
Saks, M., et al. An Engineered Tetrahymena tRNAGln, for in Vivo Incorporation of Unnatural Amino Acids into Proteins by Nonsense Suppression, J. of Biol. Chem., 271(38):23169-23175, (Sep. 20, 1996).

Salyers, A., et al. "Conjugative Transposons: an Unusual and Diverse Set of Integrated Gene Transfer Elements," Microbiological Reviews, 59(4):579-590, (Dec. 1995).
Sanjana, N. et al., A Transcription activator-like effector toolbox for genome engineering, Nature Protocols, Nature Publishing Group. Jan. 1, 2012;7(1):171-192.
Sato et al. The cisA cistron of Bacillus subtilis sporulation gene spoIVC encodes a protein homologous to a site-specific recombinase (1990) J. Bacteriol. 172: 1092-1098.
Sato, T., et al. "Production of menaquinone (vitamin K2)-7 by Bacillus subtilis," J. of Bioscience and Engineering, 91(1):16-20, (2001).
Sauer, Functional expression of the ere-lox site-specific recombination system in the yeast *Saccharomyces cerevisiae* (1987) Mol. Cell. Biol. 7: 2087-2096.
Schaerli, Y., et al., ContinuoFlow polymerase Chain reaction of single-copy DNA Micorfluidic Microdroplets, Anal. Chem., 81: 302-306, (2009).
Scior, Annike et al., Directed PCR-free engineering of highly repetitive DNA sequences, BMC Biotechnology, Biomed Central Ltd., London, GB, vol. 11(1):87, Sep. 23, 2011.
Semizarov, D., et al. "Stereoisomers of Deoxynucleoside 5'-Triphosphates as Substrates for Template-dependent and -independent DNA Polymerases," J. Biol. Chem., 272(14) 9556-9560 (1997).
Seo, T., et al., Four-color DNA sequencing by synthesis on a chip using photocleavable fluorescent nucleotides, PNAS, 102(17):5926-5933, (Apr. 26, 2005).
Sgaramella, V., et al. "Studies of polynucleotides, C.: A novel joining reaction catalyzed by T4-polynucleotide ligase", PNAS, 67(3): 1468-1475, (Nov. 1970).
Shabarova, Z., et al., Chemical ligation of DNA: the first non-enzymatic assembly of a biologically active gene, Nucl. Acids Res., 19(15):4247-4251, (1991).
Shao, Z., et al. "Random-Priming In Vitro Recombination: An Effective Tool for Directed Evolution," Nucleic Acids Research, 26(2):681-683, (1998).
Shendure et al., Accurate Multiplex Polony Sequencing of an Evolved Bacterial Genome, Science. 309:1728-1732 (2005).
Shpaer, GeneAssist. Smith-Waterman and other database similarity searches and identification of motifs: Methods Mol. Biol. 70: 173-187, 1997.
Sieber, V., et al. "Libraries of Hybrid Proteins From Distantly Related Sequences," Nature Biotechnology, 19: 456-460, (May 2001).
Simon, D., et al. N-methyl-D-aspartate receptor antagonists disrupt the formation of a mammalian neural map Proc Natl Acad Sci USA, 89:10593-10597, (Nov. 1992).
Smith et al., A detailed study of the substrate specificity of a chimeric restriction enzyme. Nucleic Acids Research 27(2):674-681 (1999).
Smith et al., Single-step purification of polypeptides expressed in *Escherichia coli* as fusions with glutathione Sransferase, Gene, vol. 67, Issue 1, pp. 31-40, (1988).
Smith, H.O., et al. "Generating a synthetic genome by whole genome assembly:<DX174 bacteriophage from synthetic oligonucleotides," PNAS, 100(26):15440-15445 (2003).
Smith, J. & Modrich, P. "Mutation Detection with MutH, MutL, and MutS Mismatch Repair Proteins," Proc. Natl. Acad. Sci. USA, 93:4374-4379, (Apr. 1996).
Soderlind et al. "Domain libraries: Synthetic diversity for de novo design of antibody V-regions." Gene, 160 (1995) 269-272.
Sprinzl et al., Compilation of tRNA sequences and sequences of tRNA genes, Nucleic Acids Research, 33:D139-D140 (2005).
Stamm et al., "Sanchored PCR: PCR with CDNA Coupled to a solid phase," Nucleic Acids Research, 19(6):1350, (Mar. 25, 1991).
Stekel, D., "Microarrays: Making Them and Using Them in Microarray Bioinformatics," Cambridge University Press, 10 pages, (2003).
Stemmer et al., Single-step assembly of a gene and entire plasmid from large numbers of oligodeoxyribonucleotides Gene, 164 (1): 49-53, (1995).

(56) References Cited

OTHER PUBLICATIONS

Stemmer, DNA shuffling by random fragmentation and reassembly: in vitro recombination for molecular evolution, Proc. Natl. Acad. Sci. USA, 91:10747-10751, (1994).

Sternberg et al. Site-specific Recombination and Its Role in the Life Cycle of Bacteriophage P1 Cold Spring Harbor Symp. Quant. Biol. 45: 297-309, 1981.

Steuer, Shawn et al. "Chimeras of the Homing Endonuclease Pi-SceI and the Homologous Candida Tropicalis Intein a Study to Explore the Possibility of Exchanging DNA-Binding Modules to Obtain Highly Specific Endonucleases With Altered Specificity" ChemBioChem, vol. 5 Issue 2, pp. 206-213, (2004).

Strizhov et al. "A synthetic cryiC gene, encoding a Bacillus Thuringiensis delta-endotoxin, confers Spodotera resistance in Alfafa and Tobacco" P.N.AS., 1996, vol. 93, No. 26, pp. 15012-15017.

Tan, S., et al. "Zinc-finger protein-targeted gene regulation: Genomewide single-gene specificity," PNAS, 100(21):11997-12002, (Oct. 14, 2003).

Tang K. et al. "Chip-based genotyping by mass spectrometry." PNAS, 96:10016-10020 (1999).

Teh et al., Droplet microfluidics, Lab on Chip. 2008;8(2):198-220.

Third Party Observation under Article 115 EPC for EP publication No. 2864531, filed May 18, 2018.

Tian, J., et al. Accurate multiplex gene synthesis from programmable DNA microchips, Nature, 432:1050-1054, (Dec. 2004).

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014. Online Methods.

Tsutakawa, S. & Morikawa, K. "The Structural Basis of Damaged DNA Recognition and Endonucleolytic Cleavage for Very Short Patch Repair Endonuclease," Nucleic Acids Research, 29(18):3775-3783, (2001).

Tucker et al., Massively parallel sequencing: the next big thing in genetic medicine. Am J Hum Genet. Aug. 2009;85(2):142-54. doi:10.1016/j.ajhg.2009.06.022.

Urata, H., et al. "Synthesis and properties of mirror-image DNA," 20(13):3325-3332 (1992).

Venkatesan et al., Improved Utility of Photolabile Solid Phase Synthesis Supports for the Synthesis of Oligonucleotides Containing 3'-Hydroxyl Termini, J. of Org. Chem., 61:525-529, (Jan. 26, 1996).

Verma et al., Modified Oligonucleotides: Synthesis and Strategy for Users, Annu. Rev. Biochem., 67:99-134, (1998).

Vogelstein et al., Digital PCR, Pro. Natl. Acad. Sci. 96(16):9236-9241 (1999).

Von Neumann T. "The general and logical theory of automata," Pergamon Press, Taub A.H (Editor) vol. 5, 288-326 (1948).

Wang et al., De novo assembly and characterization of root transcriptome using Illumina paired-end sequencing and development of cSSR markers in sweetpotato (Ipomoea batatas), BMC Genomics, 2010, vol. 11, pp. 1-14.

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.

Waters, V. Conjugation between bacterial and mammalian cells, Nature Genetics, 29:375-376, (Dec. 2001).

Weber et al.. A Modular Cloning System for Standardized Assembly of Multigene Constructs, PLoS One, Feb. 18, 2011, vol. 6, No. 2, pp. e16765.

Weiler and Hoheisel "Combining the Preparation of Oligonucleotide Arrays and Synthesis of High-Quality Primers." Analytical Biochemistry, vol. 243, Issue 2, Dec. 15, 1996, pp. 218-227.

Weiner et al., Kits and their unique role in molecular biology: a brief retrospective. Biotechniques. Apr. 2008;44(5):701-4. doi: 10.2144/000112796.

Weisberg, et al., Site-specific recombination in Phage Lambda, In: Lambda II, Hendrix, et al. Eds., Cold Spring Harbor Press, Cold Spring Harbor, NY (1983) pp. 211-250.

Werner et al., Fast track assembly of multigene constructs using Golden Gate cloning and the MoClo system, Bioengineered Bugs, Jan. 1, 2012;3(1):38-43.

Wheeler DL "Database resources of the National Center for Biotechnology Information" Nucleic Acids Res. 29(1): 11-6 (Jan. 2001).

White et al. (Digital PCR provides sensitive and absolute calibration for high throughput sequencing, BMC Genomics, 2009, 10:116, Published: Mar. 19, 2009).

Wiedmann, M., "Ligase chain reaction (LCR)—overview and application", 3:S51-S64, http://genome.cshlp.org/content/3/4/S51refs.html, Copyright 1994 by Cold Spring Harbor.

Wilgenbus & Lichter "DNA chip technology ante portas" J. Mol. Med 1999, 77:761-768.

Williams et al., Modifying the stereochemistry of an enzyme-catalyzed reaction by directed evolution. Proc Natl Acad Sci U S A. Mar. 18, 2003;100(6):3143-8. Epub Mar. 7, 2003.

Xie, J. & Schultz, P. "An Expanding Genetic Code," Methods a Companion to Methods in Enzymology, 36:227-238, (2005).

Xiong et al. PCR based accurate synthesis of long DNA sequences Nature protocols 1 (2): 791 (2006).

Xiong et al., Non-Polymerase-Cycling-Assembly-Based Chemical Gene Synthesis: Strategies, Methods, and Progress; Biotechnology Advances; Elsevier Publishing; Barking, GB; vol. 26; No. 2; pp. 121-134; Nov. 7, 2007.

Xiong, A., et al. "A simple, rapid, high-fidelity and cost-effective PCR-based two-step DNA synthesis method for long gene sequences," Nucleic Acids Research, 32(12):e98 (10 pages), (2004).

Xu et al., High sequence fidelity in a non-enzymatic DNA autoligation reaction, Nucleic Acids Research, 27(3):875-881, (1999).

Xu, Y. & Kool, E. "A novel 5'-iodonucleoside allows efficient nonenzymatic ligation of single-stranded and duplex DNAs," Tetrahedron Letters, 38(32):5595-5598, (1997).

Xu, Y., et al. Nonenzymatic autoligation in direct three-color detection of RNA and DNA point mutations, Nature Biotechnology, 19:148-152, (Feb. 2001).

Xuei et al. "Use of SAM(2)(R) biotin capture membrane in microarrayed compound screening (mu ARCS) format for nucleic acid polymerization assays" Journal of Biomolecular Screening 8:273-282 (2003).

Yan et al., Polymer membranes with two-dimensionally arranged pores derived from monolayers of silica particles, Chem. Mater. 16(9): 1622-1626 (2004).

Yehezkel et al. (De novo DNA synthesis using single molecule PCR, Nucleic Acids Research, 2008, vol. 36, No. 17, e107, Published online Jul. 30, 2008).

Yolov et al."RNA-synthesis by use of T7-RNA-Polymerase and immobilized DNA in a flowing-type reactor". Bioorganicheskaya Khimiya, 17:789-794 (1991).

Yoon et al., Efficient cloning and engineering of entire mitochondrial genomes in *Escherichia coli* and transfer into transcriptionally active mitochondria, Nucleic Acids Research, 31(5):1407-1415, (2003).

Yoon, Y., et al. Cre/loxP-mediated in vivo excision of large segments from yeast genome and their amplification based on the 2 um plasmid-derived system, Gene, 223:67-76, (1998).

Yosef et al., Restoration of gene function by homologous recombination: from PCR to gene expression in one step. Appl Environ Microbiol. Dec. 2004;70(12):7156-60.

Young et al., Two-step Total Gene Synthesis Method Nucleic Acids Research, 32(7):e59 (6 pages), (2004).

Zha, D., et al. "Assembly of Designed Oligonucleotides as an Efficient Method for Gene Recombination: A New Tool in Directed Evolution," ChemBioChem, 4: 34-39, (2003).

Zhang, C., et al., PCR microfluidic devices for DNA amplification, Biotechnology Advances, 24(3):243-284, 2006.

Zhang, P. et al. "Rational Design of a Chimeric Endonuclease Targeted to NotI Recognition Site" Protein Engineering Design & Selection, 20(10):497-504, (Oct. 2007).

Zhang, Z., et al. "Selective Incorporation of 5-Hydroxytryptophan Into Proteins in Mammalian Cells," Proceedings of the National Academy of Sciences of the United States of America, 101(24):8882-8887, (Jun. 15, 2004).

(56) References Cited

OTHER PUBLICATIONS

Zhao, H., et al. "Molecular Evolution by Staggered Extension Process (STEP) In Vitro Recombination," Nature Biotechnology, 16:258-261, (Mar. 1998).
Zhou. X., et al. "Microfluidic PicoArray synthesis of oligodeoxynucleotides and simultaneous assembling of multiple DNA sequences," Nucleic Acids Research, 32(18):5409-5417 (2004).
Zhu et al., (1995). Cleavage-dependent Ligation by the FLP Recombinase. J Biol Chem 270: 23044-23054.
Hayden et al., Gene synthesis by serial cloning of oligonucleotides. DNA. Oct. 1988;7(8):571-7.
Miller et al., Basic concepts of microarrays and potential applications in clinical microbiology. Clin Microbiol Rev. Oct. 2009;22(4):611-33. doi: 10.1128/CMR.00019-09.

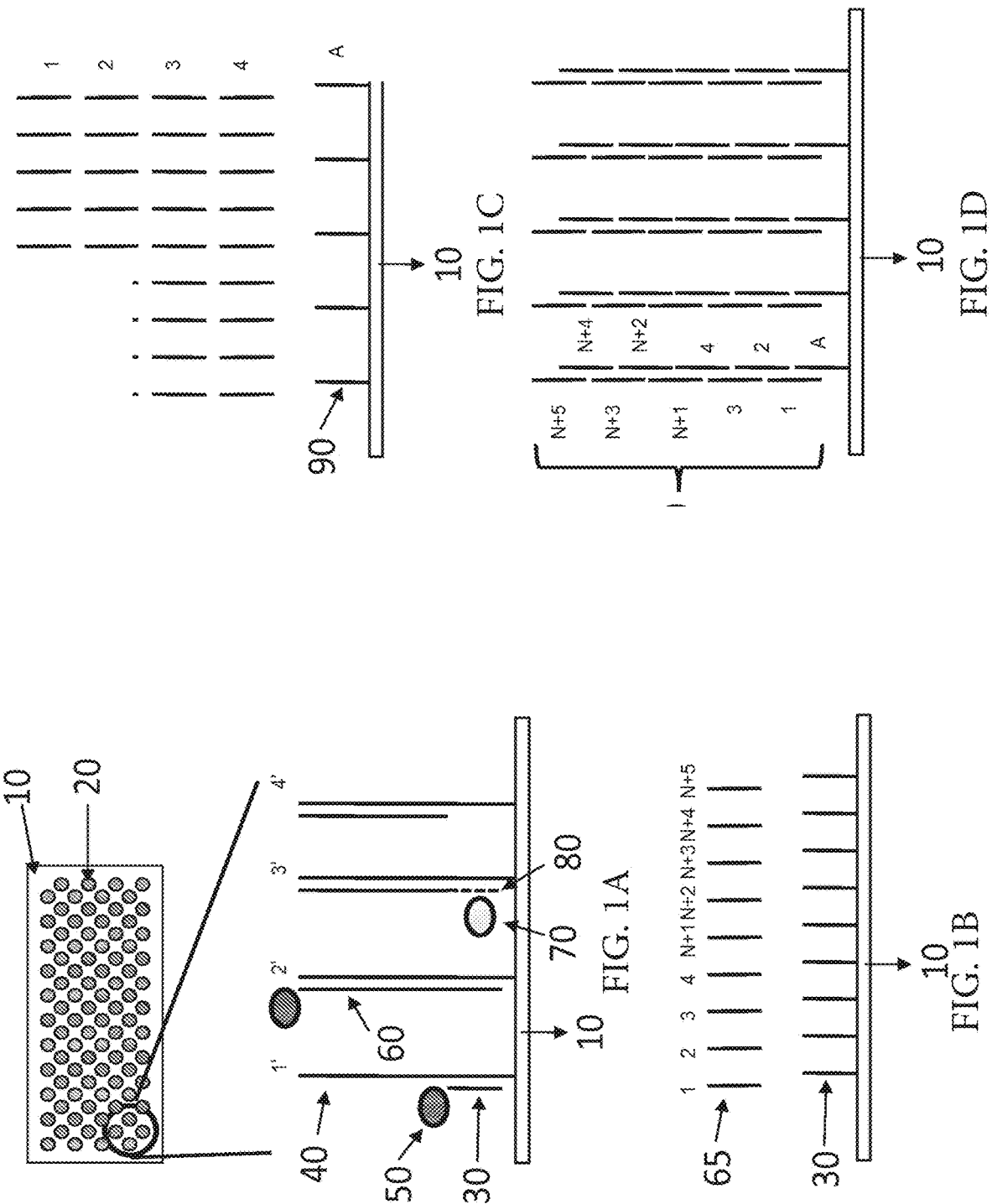

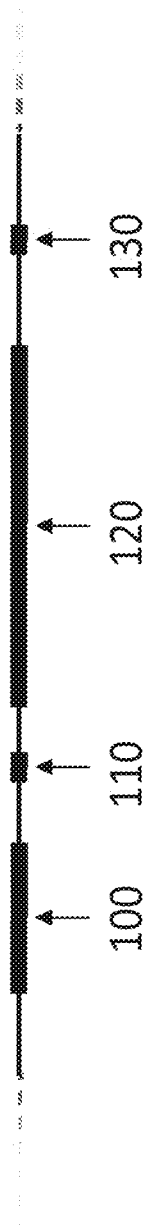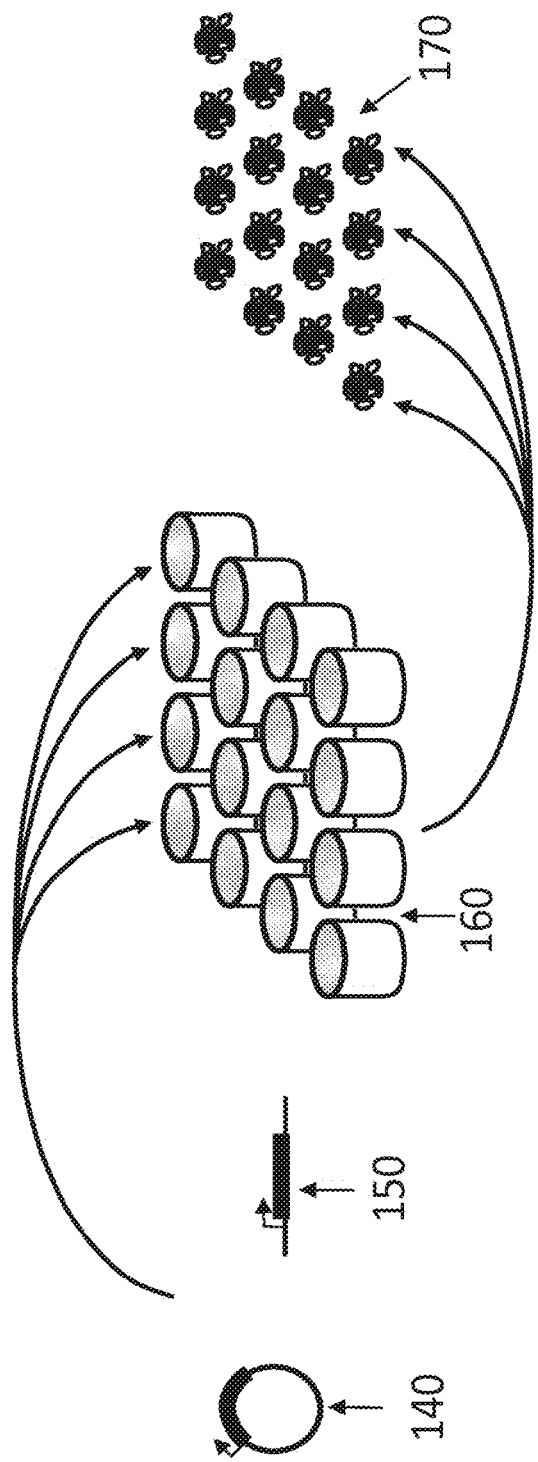

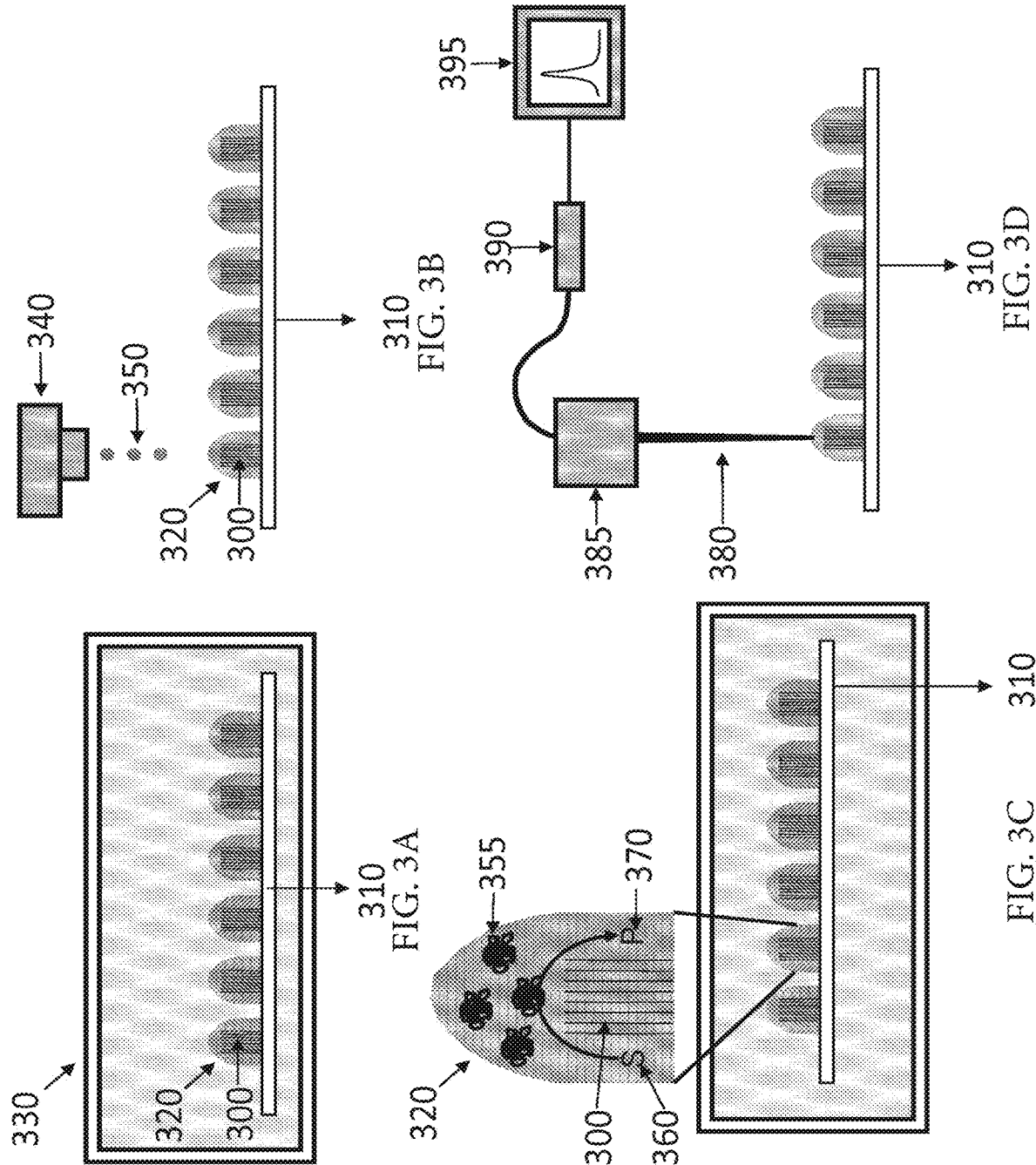

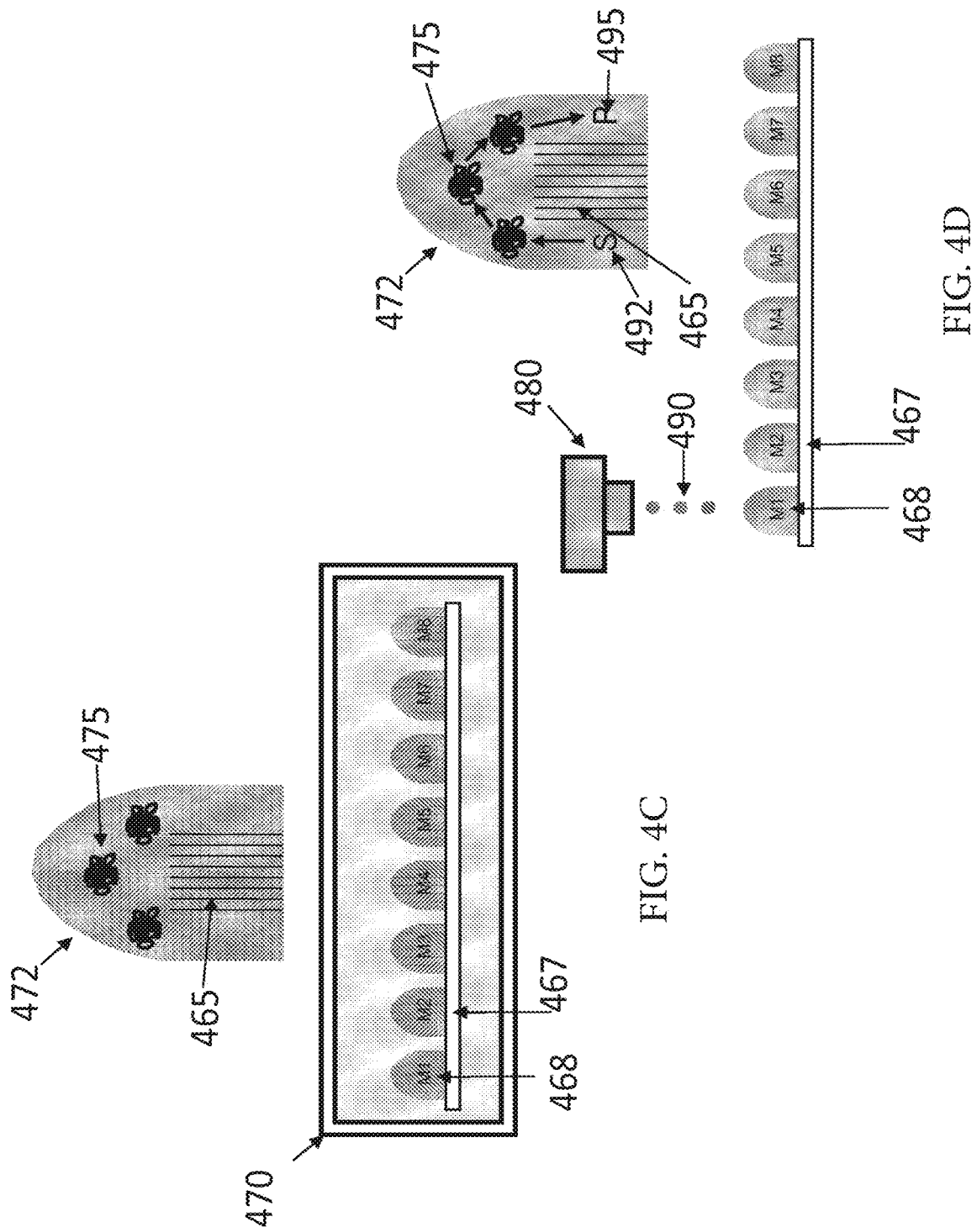

PROTEIN ARRAYS AND METHODS OF USING AND MAKING THE SAME

RELATED APPLICATIONS

This application is a divisional application of U.S. application Ser. No. 13/884,446, filed Jul. 29, 2013, now issued U.S. Pat. No. 10,457,935, which is a national phase application of International Application No. PCT/US2011/060217, filed Nov. 10, 2011, which claims priority to and the benefit of U.S. provisional application No. 61/412,941, filed Nov. 12, 2010, the entire contents of each of which are incorporated by reference herein.

FIELD OF THE INVENTION

Methods and devices provided herein generally relate to the preparation of high content gene libraries and libraries of polypeptides expressed therefrom. More particularly, the methods and devices involve microvolume reactions, gene assembly, on-surface expression, high throughput analysis, and/or pathway development on a solid support.

BACKGROUND

In vitro manipulation of nucleic acids and proteins is an important aspect of modern molecular biology and functional genomics. Recent advances in DNA synthesis have started to make the production of large scale DNA libraries an economical reality. However, the next step, the use of those DNA libraries to produce large ordered protein libraries has not scaled to the same extent. Synthetic DNA constructs encoding genes are routinely cloned into plasmids that are then introduced into bacteria which are then in turn, used as hosts for protein production. While these techniques themselves are routine, they are time consuming and relatively limited in the potential scale of the library to be generated. As for commercially available libraries, each component of the library must be grown up in the host bacteria separately. This limits the scalability of in vivo protein library expression as each sample must be grown up in a minimal volume in order to produce enough protein to work with in downstream applications. In addition, growth of the host bacteria can be costly in time, taking a day or more of time for incubation. Together, these issues limit the number of samples that can be effectively grown in parallel.

Accordingly, there is a need for high-throughput techniques for the rapid synthesis and selection of genes and proteins of interest. Such techniques would permit the discovery and development of proteins with improved properties that can be used for analytical, research, diagnostic, and therapeutic purposes.

SUMMARY

Methods and devices of the present invention relate to microvolume reactions, gene assembly, on-surface expression, high throughput analysis, and/or pathway development on a solid support.

In one aspect, the present invention features a method for preparing a protein array having a plurality of proteins. The method includes providing a plurality of nucleic acids each having a predefined sequence. The method further includes expressing in vitro a plurality of proteins from the plurality of nucleic acids.

In certain embodiments, the method further includes measuring an activity of each of the plurality of proteins. In some embodiments, the plurality of nucleic acids are produced on a solid surface. The plurality of nucleic acids can each comprise a regulatory genetic sequence. In certain embodiments, expressing in vitro can be performed in a micro-well plate or at discrete features on support or a solid surface.

The present invention, in a second aspect, features a method for preparing a protein array having a plurality of proteins. The method includes providing a microvolume comprising a population of nucleic acids. In some embodiments, the population of nucleic acids can be immobilized at discrete features of the support buy hybridizing the population of nucleic acids onto support-bound anchor oligonucleotides. The population of nucleic acids can have a plurality of distinct, predefined sequences. The method further includes expressing in vitro in said microvolume a plurality of proteins from the population of nucleic acids.

In one aspect, the present invention features a method for producing at least one protein, the method comprising (a) providing a support having a plurality of distinct features, each feature comprising a plurality of immobilized anchor oligonucleotides; (b) generating at least one plurality of nucleic acid having a predefined sequence onto the plurality of anchor oligonucleotides; (c) providing a microvolume onto at least one feature of the support; and (d) expressing in vitro in the microvolume the at least one protein from the at least one nucleic acid. The microvolume can comprise reagents appropriate for expressing in vitro the at least one protein from the at least one nucleic acid. In some embodiments, each feature of the support comprises a distinct plurality of support-bound anchor oligonucleotides wherein the 5' end of each of the plurality of anchor oligonucleotide is complementary to the 5' end of a distinct nucleic acid having a predefined sequence. In some embodiments, the plurality of nucleic acids are generated by assembling a plurality of construction oligonucleotides comprising partially overlapping sequences that define the sequence of the at least one nucleic acid. In some embodiments, the at least one nucleic acid is generated under (i) ligation conditions, (ii) chain extension conditions, or (iii) chain extension and ligation conditions. In some embodiments, the method further comprises verifying the at least one nucleic acid sequence prior to the step of expressing the protein(s). In some embodiments, the method further comprises synthesizing a plurality of partially overlapping construction oligonucleotides, wherein each construction oligonucleotide is synthesized at a distinct feature of the support comprising immobilized complementary construction oligonucleotides, releasing the construction oligonucleotides in at least one microvolume, and transferring the at least one microvolume to a feature comprising a plurality of anchor oligonucleotides.

In some aspects of the invention, the methods and devices may be used to produce at least 100, 1,000, 10,000 or more proteins. In some embodiments, the proteins are proteins variants. In some embodiments, the method further comprises screening the at least one protein to identify proteins having a desired characteristic.

In another aspect, protein arrays having a solid surface and a microvolume are also provided. The solid surface can have a plurality of anchor oligonucleotides capable of hybridizing with a plurality of nucleic acids. The microvolume can cover each of the plurality of anchor oligonucleotides and can be configured to produce a polypeptide from each of the plurality of nucleic acids.

In another aspect, proteins arrays comprises (a) a first plurality of features on a support, each of the first plurality of features comprising a plurality of immobilized single stranded oligonucleotides, wherein the plurality of single stranded oligonucleotides comprises partially overlapping sequences that define the sequence of each of a plurality of nucleic acid molecules encoding a plurality of proteins; and (b) a second plurality of features, the second plurality of features comprising a plurality of anchor oligonucleotides having a sequence complementary to a terminus sequence of each of the plurality nucleic acids.

BRIEF DESCRIPTION OF THE DRAWINGS

FIGS. 1A-1D illustrate an embodiment of the method and device for gene synthesis. FIG. 1A illustrates a microarray (10) having groups (20) of single-stranded DNA (40). FIG. 1A illustrates introduction of universal primer (30) and polymerase (50) to create a complementary second strand of DNA (60), and of enzyme (70) to fragment primer. FIG. 1B illustrates release of a plurality of populations of oligonucleotides (65) in solution. FIG. 1C illustrates the transfer of eluted oligonucleotides (65) to an area having anchor oligonucleotides A (90) immobilized on its surface. FIG. 1D illustrates anchor oligonucleotides A (90) acting as points of nucleation for the construction of the DNA product (100) on the surface of the microarray (10).

FIGS. 2A-2C illustrate an embodiment of the method and device for on-surface expression of proteins. FIG. 2A illustrates a nucleic acid having a T7 promoter (100), an *E. coli* ribosome binding site (110) upstream of a gene of interest (120), and a transcriptional terminator (130) downstream of the gene of interest (120). FIG. 2B illustrates a library of synthetic nucleic acid constructs integrated into a plasmid (140) or in linear form (150) being transferred to individual wells of a micro-well plate containing the appropriate transcription/translation reaction reagents (160), and expression of the proteins (170) encoded by the gene library. FIG. 2C illustrates a droplet based dispensing apparatus (200) to dispense droplets (210) of transcription/translation reagents directly onto specific locations of the solid surface (180) and covering the deposited nucleic acid constructs (190) forming a self-contained reaction volume (220). FIG. 2C illustrates the solid surface with the reaction mixtures inserted into a humidity controlled chamber (230) and expression of the proteins (170) from the nucleic acid library.

FIGS. 3A-3D illustrate an embodiment of the method and device for high throughput analysis of on-surface expressed proteins. FIG. 3A illustrates incubation of solid support (310) having synthetic nucleic acid constructs (300) covered with a droplet of transcription/translation reagent mix (320) in a humidity controlled chamber (330). FIG. 3B illustrates protein expression phase using a droplet based dispensing apparatus (340) to dispense reagents in drop wise manner at specific location (or features) on the support or solid surface (310). FIG. 3C illustrates conversion of substrate (360) to product (370) in presence of enzyme (355). FIG. 3D illustrates sampling and assaying the presence of product (370).

FIGS. 4A-4D illustrate an embodiment of the method and device for multi-protein pathway development. FIG. 4A illustrates a microarray (400) containing the oligonucleotides (410) to build a set of genes (420). FIG. 4B illustrates mixing linear nucleic acid constructs (440) to give all the potential combinations (460). FIG. 4C illustrates production of protein combinations (475). FIG. 4D illustrates conversion of substrates (492) to product (495).

DETAILED DESCRIPTION OF THE INVENTION

Figure 2C:
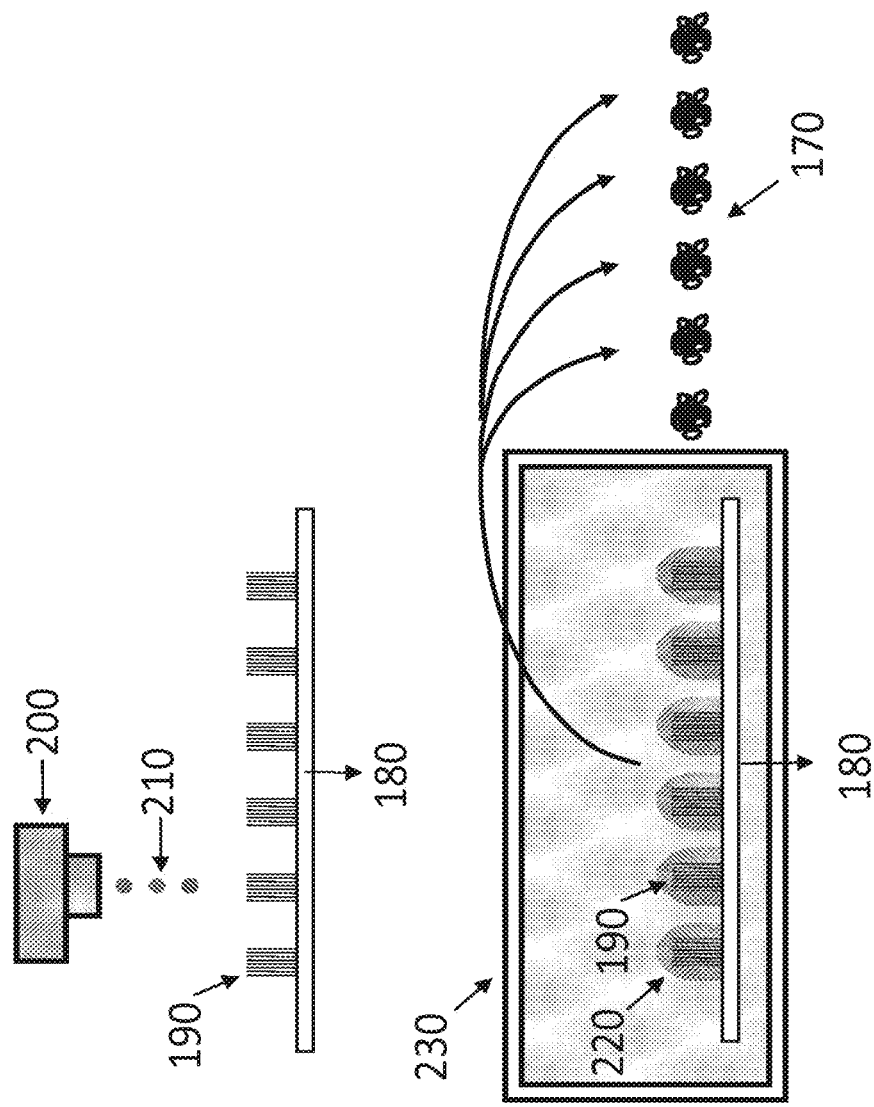
Figure 4A:
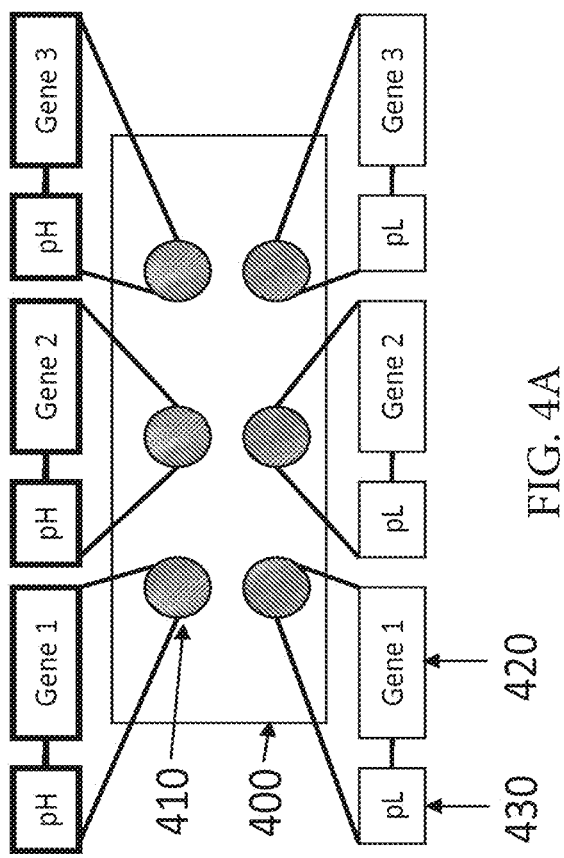
Figure 4B:
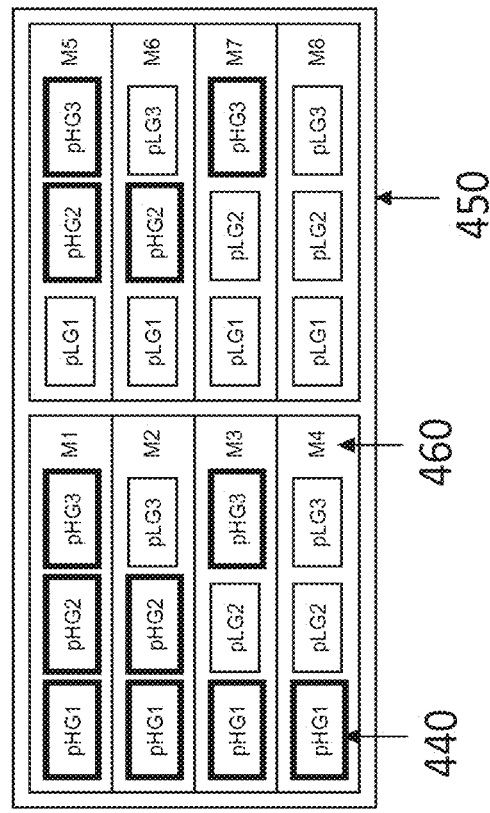

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in the expression of the protein. When the gene encodes an untranslated RNA, it includes the promoter and the nucleic acid that encodes the untranslated RNA.

The term "gene of interest" (GOI) refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the phrase "nucleic acids" or "nucleic acid molecule" refers to a sequence of contiguous nucleotides (riboNTPs, dNTPs, ddNTPs, or combinations thereof) of any length. A nucleic acid molecule may encode a full-length polypeptide or a fragment of any length thereof, or may be non-coding. As used herein, the terms "nucleic acids," "nucleic acid molecule", "polynucleotide" and "oligonucleotide" may be used interchangeably and include both single-stranded (ss) and double-stranded (ds) RNA, DNA and RNA:DNA hybrids.

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the polynucleotides that encode the protein sequences under stringent conditions, such as those described herein.

As used herein, a "polymerase" is an enzyme that catalyses synthesis of nucleic acids using a preexisting nucleic acid template. Examples include DNA polymerase (which catalyzes DNA 7DNA reactions), RNA polymerase (DNA7RNA) and reverse transcriptase (RNA7DNA).

As used herein, the term "polypeptide" refers to a sequence of contiguous amino acids of any length. The terms "peptide," "oligopeptide," or "protein" may be used interchangeably herein with the term "polypeptide."

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be constitutive or regulateable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream the start site are numbered +1, +2, etc., and nucleotides upstream the start site are numbered −1, −2, etc. Additional promoter elements are located 5' (i.e. typically 30-250 bp upstream the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors (see, for example, Hawley; D. K. et al (1983) Nucl. Acids Res. 11, 2237-2255). The −10 sequence (10 bp upstream from the first transcribed nucleotide) is typically about 6 nucleotides in length and is typically made up of the nucleotides adenosine and thymidine (also known as the Pribnow box). In some embodiments, the nucleotide sequence of the −10 sequence is 5'-TATAAT or may comprise 3 to 6 bases pairs of the consensus sequence. The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the nucleotide sequence of the −35 sequence is 5'-TTGACA or may comprise 3 to 6 bases pairs of the consensus sequence. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box (e.g. containing the consensus sequence TATAAA or part thereof), which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

As used herein, the terms protein of interest (POT) and "desired protein" refer to a polypeptide under study, or whose expression is desired by one practicing the methods disclosed herein. A protein of interest is encoded by its cognate gene of interest (GOI). The identity of a POI can be known or not known. A POI can be a polypeptide encoded by an open reading frame.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5' UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG (SEQ ID NO. 1), which lies within a short 5' untranslated region, directs translation of mRNA. An mRNA lacking the Kozak consensus sequence may also be translated efficiently in an in vitro systems if it possesses a moderately long 5' UTR that lacks stable secondary structure. While E. coli ribosome preferentially recognizes the Shine-Dalgarno sequence, eukaryotic ribosomes (such as those found in retic lysate) can efficiently use either the Shine-Dalgarno or the Kozak ribosomal binding sites.

As used herein, the term "vector" refers to any genetic element, such as a plasmid, phage, transposon, cosmid, chromosome, virus, virion, etc., which is capable of replication when associated with the proper control elements and which can transfer gene sequences between cells. The vector may contain a marker suitable for use in the identification of transformed cells. For example, markers may provide tetracycline resistance or ampicillin resistance. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The tetra "expression vector" refers to a vector which is capable of expressing a gene that has been cloned into it. Such expression can occur after transformation into a host cell, or in IVPS systems. The cloned DNA is usually operably linked to one or more regulatory sequences, such as promoters, repressor binding sites, terminators, enhancers and the like. The promoter sequences can be constitutive, inducible and/or repressible.

As used herein, the term "host" refers to any prokaryotic or eukaryotic (e.g., mammalian, insect, yeast, plant, avian, animal, etc.) organism that is a recipient of a replicable expression vector, cloning vector or any nucleic acid molecule. The nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Sambrook, et al., Molecular Cloning: A Laboratory Manual, Cold Spring Harbor Laboratory, Cold Spring Harbor, N.Y.

As used herein, "in vitro" refers to systems outside a cell or organism and may sometimes be referred to cell free system. In vivo systems relate to essentially intact cells whether in suspension or attached to or in contact with other cells or a solid. In vitro systems have an advantage of being more readily manipulated. For example, delivering components to a cell interior is not a concern; manipulations incompatible with continued cell function are also possible. However, in vitro systems involve disrupted cells or the use of various components to provide the desired function and thus spatial relationships of the cell are lost. When an in vitro system is prepared, components, possibly critical to the desired activity can be lost with discarded cell debris. Thus in vitro systems are more manipulatable and can function differently from in vivo systems. In some embodiments, hybrid in vitro/in vivo systems can also be used.

The terms "in vitro transcription" (IVT) and "cell-free transcription" are used interchangeably herein and are intended to refer to any method for cell-free synthesis of RNA from DNA without synthesis of protein from the RNA. A preferred RNA is messenger RNA (mRNA), which encodes proteins. The terms "in vitro transcription-translation" (IVTT), "cell-free transcription-translation", "DNA template-driven in vitro protein synthesis" and "DNA template-driven cell-free protein synthesis" are used interchangeably herein and are intended to refer to any method for cell-free synthesis of mRNA from DNA (transcription) and of protein from mRNA (translation). The terms "in vitro protein synthesis" (IVPS), "in vitro translation", "cell-free translation", "RNA template-driven in vitro protein synthesis", "RNA template-driven cell-free protein synthesis" and "cell-free protein synthesis" are used interchangeably herein and are intended to refer to any method for cell-free synthesis of a protein. IVTT, including coupled transcription and transcription, is one non-limiting example of IVPS.

As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases.

As used herein, the term monomer refers to a member of a set of small molecules which are and can be joined together to form an oligomer, a polymer or a compound composed of two or more members. The particular ordering of monomers within a polymer is referred to herein as the "sequence" of the polymer. The set of monomers includes but is not limited to, for example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other other polymers.

As used herein, the term "predefined sequence" means that the sequence of the polymer is designed or known and chosen before synthesis or assembly of the polymer. In particular, aspects of the invention is described herein primarily with regard to the preparation of nucleic acids molecules, the sequence of the oligonucleotides or polynucleotides being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotides constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different lengths. In some embodiments, the sequence of the polynucleotide construct may be divided up into a plurality of shorter sequences that can be synthesized in parallel and assembled into a single or a plurality of desired polynucleotide constructs using the methods described herein.

As used herein, the term "genome" refers to the whole hereditary information of an organism that is encoded in the DNA (or RNA for certain viral species) including both coding and non-coding sequences. In various embodiments, the term may include the chromosomal DNA of an organism and/or DNA that is contained in an organelle such as, for example, the mitochondria or chloroplasts and/or extrachromosomal plasmid and/or artificial chromosome. A "native gene" refers to a gene that is native to the host cell with its own regulatory sequences whereas an "exogenous gene" or "heterologous gene" refers to any gene that is not a native gene, comprising regulatory and/or coding sequences that are not native to the host cell. In some embodiments, an heterologous gene may comprise mutated sequences or part of regulatory and/or coding sequences. In some embodiments, the regulatory sequences may be heterologous or homologous to a gene of interest. An heterologous regulatory sequence does not function in nature to regulate the same gene(s) it is regulating in the transformed host cell. "Coding sequence" refers to a DNA sequence coding for a specific amino acid sequence. As used herein, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As described herein, a genetic element may be any coding or non-coding nucleic acid sequence. In some embodiments, a genetic element is a nucleic acid that codes for an amino acid, a peptide or a protein, Genetic elements may be operons, genes, gene fragments, promoters, exons, introns, etc. or any combination thereof. Genetic elements can be as short as one or a few codons or may be longer including functional components (e.g. encoding proteins) and/or regulatory components. In some embodiments, a genetic element consists of an entire open reading frame of a protein, or consists of the entire open reading frame and one or more (o all) regulatory sequences associated with that open reading frame. One skilled in the art will appreciate that the genetic elements can be viewed as modular genetic elements or genetic modules. For example, a genetic module can comprise a regulator sequence or a promoter or a coding sequence or any combination thereof. In some embodiments, the genetic element comprises at least two different genetic modules and at least two recombination sites. In eukaryotes, the genetic element can comprise at least three modules. For example, a genetic module can be a regulator sequence or a promoter, a coding sequence, and a polyadenlylation tail or any combination thereof. In addition to the promoter and the coding sequences, the nucleic acid sequence may comprise control modules including, but not limited to a leader sequence, a signal sequence and a transcription terminator sequence. The leader sequence is a non-translated region operably linked to the 5' terminus of the coding nucleic acid sequence. The signal peptide sequence codes for an amino acid sequence linked to the amino terminus of the polypeptide which directs the polypeptide into the cell's secretion pathway.

Genetic elements or genetic modules may derive from the genome of natural organisms or from synthetic polynucleotides or from a combination thereof In some embodiments, the genetic elements or modules derive from different organisms. Genetic elements or modules useful for the methods described herein may be obtained from a variety of sources such as, for example, DNA libraries, BAC libraries, de novo chemical synthesis, or excision and modification of a genomic segment. The sequences obtained from such sources may then be modified using standard molecular biology and/or recombinant DNA technology to produce polynucleotide constructs having desired modifications for reintroduction into, or construction of, a large product nucleic acid, including a modified, partially synthetic or fully synthetic genome. Exemplary methods for modification of polynucleotide sequences obtained from a genome or library include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic polynucleotides. Synthetic polynucleotides may be produced using a variety of methods such as high throughput oligonucleotide assembly techniques known in the art. For example, oligonucleotides having complementary, overlapping sequences may be synthesized on an array and then eluted or released from the array. The oligonucleotides can then be induced to self assemble based on hybridization of the complementary regions. In some embodiments, the methods involve one or more nucleic assembly reactions in order to synthesize the genetic elements of interest. The method may use in vitro and/or in vivo nucleic acid assembly procedures. Non-limiting examples of nucleic acid assembly procedures and library of nucleic acid assembly procedure are known in the art and can be found in, for example, U.S. patent applications 20060194214, 20070231805, 20070122817, 20070269870, 20080064610, 20080287320, the disclosures of which are incorporated by reference.

In some embodiments, genetic elements sequence share less than 99%, less than 95%, less than 90%, less than 80%, less than 70% identity with a native or natural nucleic acid sequence. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed, Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

It should be appreciated that the nucleic acid sequence of interest or the gene of interest may be derived from the genome of natural organisms. In some embodiments, genes of interest may be excised form the genome of a natural organism or form the host genome, for example *E. coli*. It has been shown that it is possible to excise large genomic fragments by in vitro enzymatic excision and in vivo excision and amplification. For example the FLP/ERT site specific recombination system and the Cre/loxP site specific recombination systems have been efficiently used for excision large genomic fragments for the purpose of sequencing (see, Yoon et al., Genetic Analysis: Biomolecular Engineering, 1998, 14: 89-95). In some embodiments, excision and amplification techniques can be used to facilitate artificial genome or chromosome assembly. Genomic fragments may be excised form *E. coli* chromosome and altered before being inserted into the host cell artificial genome or chromosome. In some embodiments, the excised genomic fragments can be assembled with engineered promoters and inserted into the genome of the host cell.

Other terms used in the fields of recombinant nucleic acid technology and molecular and cell biology as used herein will be generally understood by one of ordinary skill in the applicable arts.

Solid Supports

Some embodiments of the devices and methods provided herein use oligonucleotides that are immobilized on a support or substrate. As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters and the like. In such porous materials, the reaction may take place within the pores. The support can have any one of a number of shapes, such as pin, strip, plate, disk, rod, bends, cylindrical structure, particle, including bead, nanoparticle and the like. The support can have variable widths.

The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly (vinyl butyrate), polyvinylidene difluoride (PVDF) membrane, glass, controlled pore glass, magnetic controlled pore glass, ceramics, metals, and the like etc.; either used by themselves or in conjunction with other materials.

In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature can be chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

Arrays may be constructed, custom ordered or purchased from a commercial vendor (e.g., Agilent, Affymetrix, Nimblegen). Oligonucleotides are attached, spotted, immobilized, surface-bound, supported or synthesized on the discrete features of the surface or array Oligonucleotides may be covalently attached to the surface or deposited on the surface. Various methods of construction are well known in the art e.g. maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854; 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described. In U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-wells microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541, 061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles, Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824, 866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g. ink jet). In some embodiments, oligonucleotides are spotted on a support using, for example, a mechanical wave actuated dispenser.

Microfluidic Devices and Microvolume Reactions

Provided herein are microfluidic devices for the manipulation of droplets on a substrate (e.g. solid support). Methods and devices for synthesizing or amplifying oligonucleotides as well for preparing or assembling long polynucleotides having a predefined sequence are provided herein. Aspects of the technology provided herein are useful for increasing the accuracy, yield, throughput, and/or cost efficiency of nucleic acid synthesis and assembly reactions.

The manipulation of fluids to form fluid streams of desired configuration, such as discontinuous fluid streams, particles, dispersions, etc., for purposes of fluid delivery, product manufacture, analysis, and the like, is a relatively well-studied art. See for example, WO/2004/002627 which is incorporated herein in its entirety. In some aspects of the invention, microfluidic devices are used to form and manipulate droplets in a co-planar fashion to allow oligonucleotide synthesis. For example, oligonucleotides may be synthesized using a phophoramidite method. The phosphoramidite method, employing nucleotides modified with various protecting groups, is one of the most commonly used methods for the de novo synthesis of oligonucleotides. Detailed procedures for the phosphoramidite and hydrogen phosphonate methods of oligonucleotide synthesis are described in the following references that are incorporated by reference: U.S. Pat. Nos. 4,500,707; 4,725,677; and 5,047,524. See also for example, methods outlined in Oligonucleotide and Analogs: A practical approach, F. Eckstein, Ed. IRL Press Oxford University and Oligonucleotide synthesis: A practical approach, Gait, Ed. IRL Oxford Press. Synthesis can be performed either through the coupling of the 5' position of the first monomer to the 3' position of the second monomer (3'-5' synthesis) or vice versa (5'-3' synthesis). Briefly, synthesis of oligonucleotides requires the specific formation of a 3'-5' or 5'3' phosphodiester linkage. In order to form these specific linkages, the nucleophilic centers not involved in the linkage must be chemically protected through the use of protecting group. By "protecting group" as used herein is meant a species which prevents a segment of a molecule (e.g. nucleotide) from undergoing a specific chemical reaction, but which is removable from the molecule following completion of that reaction. For example, the 5' hydroxyl group may be protected by dimethoxitrityl (DMT). During the deblocking reaction, the DMT is removed with an acid, such as thrichloroacetic acid (TeA) or dichloroacetic acid, resulting in a free hydroxyl group. After washing, a phosphoramidite nucleotide is activated by tetrazole, ethylthiotetrazole, dicyanoimidazole, or benzimidazolium triflate, for example, which remove the iPr2N group on the phosphate group. The deprotected 5' hydroxyl of the first base reacts with the phosphate of the second base and a 5'-3' linkage is formed (coupling step). Unbound bases are washed out and 5' hydroxyl group that did not react during the coupling reaction are blocked by adding a capping group, which permanently binds to the free 5' hydroxyl groups to prevent any further chemical transformation of that group (capping step). The oxidation step may be performed before or after the capping step. During oxidation, the phosphite linkage is stabilized to form a much more stable phosphate linkage. The deblocking/coupling/capping/oxidation cycle may be repeated the requisite number of time to achieve the desired length polynucleotide. In some embodiments, coupling can be synchronized on the array or solid support.

In some embodiments, the oligonucleotides synthesis is performed using a device that generates emulsion droplets comprising aqueous droplets within immiscible oil. The droplets may comprise an aqueous phase, an immiscible oil phase, and a surfactant and/or other stabilizing molecules to maintain the integrity of the droplet. In some embodiment, mechanical energy is applied, allowing dispersion of a compound into an oil phase to form droplets, each of which contains a single sort of compound. Preferably, the compound is a nucleotide monomer (i.e. A, T or U, G, C). The compounds can be deposited into the oil phase in the form of droplets generated using inkjet printing technology or piezoelectric drop-on-demand (DOD) inkjet printing technology. Each droplet may comprise a different nucleotide monomer (i.e. A, T or U, G, C) in the same aqueous solution. In preferred embodiments, the droplets are uniform in size and contain one nucleotide at a fixed concentration. The droplets range in size from 0.5 microns to 500 micron in diameter, which correspond to a volume of about 1 picoliter to about 1 nano liter. Yet in other embodiments, the droplet may comprise a 2-mer, a 3-mer, a 4-mer, a 6-mer, or a 7-mer oligonucleotide. In some embodiments, the droplets are deposited onto a substrate such as a microsubstrate, a microarray or a microchip. The terms microsubstrate, microarray and microchip are used interchangeably herein. The droplets may be deposited using a microfluidic nozzle. In some embodiments, the substrate may be subjected to wash, deblocking solution, coupling, capping and oxidation reactions to elongate the oligonucleotide.

In some embodiments, the droplets carrying the nucleotides can me moved using electrowetting technologies. Electrowetting involves modifying the surface tension of liquids on a solid surface using a voltage. Application of an electric field (e.g. alternating or direct can modify the contact angle between the fluid and surfaces. For example, by applying a voltage, the wetting properties of a hydrophobic surface can become increasingly hydrophilic and therefore wettable. Electrowetting principle is based on manipulating droplets on a surface comprising an array of electrodes and using voltage to change the interfacial tension. In some embodiments, the array of electrodes is not in direct contact with the fluid. In some embodiments, the array of electrodes is configured such as the support has a hydrophilic side and a hydrophobic side. The droplets subjected to the voltage will move towards the hydrophilic side. In some embodiments, the array or pattern of electrodes is a high density pattern. One should appreciate that to be used in conjunction with the phophoramidite chemistry, the array of electrodes should be able to move droplets volumes ranging from 1 pL (and less) to 10 pL. Accordingly, aspects of the invention relate to high voltage complementary semi-conductor microfluidic controller. In some embodiments, the high voltage complementary semi-conductor device (HV-CMOS) has an integrated circuit with high density electrode pattern and high voltage electronics. In some embodiments, the voltage applied is between 15V and 30V.

Methods and devices provided herein involve amplification and/or small assembly reaction volumes such as microvolumes, nanovolumes, picovolumes or sub-picovolumes. Accordingly, aspects of the invention relate to methods and devices for amplification and/or assembly of polynucleotide sequences in small volume droplets on separate and addressable features of a support. For example, a plurality of oligonucleotides complementary to surface-bound single stranded oligonucleotides is synthesized. In a predefined reaction microvolume of solution by template-dependant synthesis. In some embodiments, predefined reaction microvolumes of between about 0.5 pL and about 100 nL may be used. However, smaller or larger volumes may be used. In some embodiments, a mechanical wave actuated dispenser may be used for transferring volumes of less than 100 nL, less than 10 nL, less than 5 nL, less than 100 pL, less than 10 pL, or about 0.5 pL or less. In some embodiments, the mechanical wave actuated dispenser can be a piezoelectric inkjet device or an acoustic liquid handler. In a preferred embodiment, a piezoelectric inkjet device is used and can deliver picoliter solutions in a very precise manner on a support.

In various embodiments, methods and devices are provided for processing independently one or more plurality of oligonucleotides and/or polypeptides in a temperature dependent manner at addressable features in isolated liquid volumes. In some embodiments, the method is conducted in a manner to provide a set of predefined single-stranded oligonucleotide sequences or complementary oligonucleotide sequences for further specified reactions or processing. One should appreciate that each features being independently addressable, each reaction can be processed independently within a predefined isolated liquid volume or droplet on a discrete feature (e.g. virtual chamber). In some embodiments, the arrays are stored dry for subsequent reactions. In a preferred embodiment, support immobilized oligonucleotides can be hydrated independently with an aqueous solution. Aqueous solution includes, but is not limited to, water, buffer, primers, master mix, release chemicals, enzymes, or any combination thereof. Aqueous solution can be spotted or jetted onto specific surface location(s) corresponding to the discrete feature(s). Subsequently, miscible as well as non-miscible solution or aqueous gel can be deposited in the same fashion. Alternatively, a mechanical wave actuated dispenser can be used for transferring small volumes of fluids (e.g., picoliter or sub-picoliter). A mechanical wave actuated dispenser can be a piezoelectric inkjet device or an acoustic liquid handler. A piezoelectric inkjet device can eject fluids by actuating a piezoelectric actuation mechanism, which forces fluid droplets to be ejected. Piezoelectrics in general have good operating bandwidth and can generate large forces in a compact size. Some of the commercially available piezoelectric inkjet microarraying instruments include those from Perkin Elmer (Wellesley, MA), GeSim (Germany) and MicroFab (Plano, Tex.). Typical piezoelectric dispensers can create droplets in the picoliter range and with coefficient of variations of 3-7%. Inkjetting technologies and devices for ejecting a plurality of fluid droplets toward discrete features on a substrate surface for deposition thereon have been described in a number of patents such as U.S. Pat. Nos. 6,511,849; 6,514,704; 6,042,211; 5,658,802, the disclosure of each of which is incorporated herein by reference.

In one embodiment, the fluid or solution deposition is performed using an acoustic liquid handler or ejector. Acoustic devices are non-contact dispensing devices able to dispense small volume of fluid (e.g. picoliter to microliter), see for example Echo 550 from Labcyte (CA), HTS-01 from EDC Biosystems, Acoustic technologies and devices for acoustically ejecting a plurality of fluid droplets toward discrete sites on a substrate surface for deposition thereon have been described in a number of patents such as U.S. Pat. Nos. 6,416,164; 6,596,239; 6,802,593; 6,932,097; 7,090,333 and US Patent Application 2002-0037579, the disclosure of each of which is incorporated herein by reference. The acoustic device includes an acoustic radiation generator or transducer that may be used to eject fluid droplets from a reservoir (e.g. microplate wells) through a coupling medium. The pressure of the focused acoustic waves at the fluid surface creates an upwelling, thereby causing the liquid to urge upwards so as to eject a droplet, for example from a well of a source plate, to a receiving plate positioned above the fluid reservoir. The volume of the droplet ejected can be determined by selecting the appropriate sound wave frequency.

In some embodiments, the source plate comprising water, buffer, primers, master mix, release chemicals, enzymes, or any combination thereof and the destination plates comprising the oligonucleotides or polynucleotides are matched up to allow proper delivery or spotting of the reagent to the proper site. The mechanical wave actuated dispenser may be coupled with a microscope and/or a camera to provide positional selection of deposited spots. A camera may be placed on both sides of the destination plate or substrate. A camera may be used to register to the positioning on the array especially if the DNA is coupled with a fluorescent label.

One should appreciate that when manipulating small liquid volumes such as picoliters and nanoliters, the smaller the droplet, the faster it will evaporate. Therefore, aspects of the invention relate to methods and devices to limit, retard or prevent water evaporation. In some embodiments, the discrete features or a subset of discrete features can be coated with a substance capable of trapping or capturing water. In other embodiments, the water-trapping material can be spin-coated onto the support. Different materials or substances can be used to trap water at specific locations. For example, the water trapping substance may be an aqueous matrix, a gel, a colloid or any suitable polymer. In some embodiments, the material is chosen to have a melting point that allows the material to remain solid or semi-solid (e.g. gel) at the reaction temperatures such as denaturing temperatures or thermocycling temperatures. Water trapping materials include but are not limited to colloidal silica, peptide gel, agarose, solgel and polydimethylsiloxane. In an exemplary embodiment, Snowtex® colloidal silica (Nissan Chemical) may be used. Snowtex® colloidal silica is composed of mono-dispersed, negatively charged, amorphous silica particles in water. Snowtex® colloidal silica can be applied as dry gel or as an hydrated gel onto the surface. In a preferred embodiment, the water trapping substance is spotted at discrete features comprising surface-bound oligonucleotides. Alternatively, oligonucleotides can be synthesized on the particles or nanoparticles (e.g. colloidal particles, Snowtex® colloidal silica) and the particles or nanoparticles can be dispensed to the discrete features of the surface. In some embodiments, the water trapping substance is spotted on the discrete features of the support using a mechanical device, an inkjet device or an acoustic liquid handler.

One should appreciate, that evaporation can also be limited by forming a physical barrier between the surface of the droplet and the atmosphere. For example, a non-miscible solution can be overlaid to protect the droplet from evaporation. In some embodiments, a small volume of the non-miscible solution is dispensed directly and selectively at discrete location of the substrate such as Features comprising a droplet. In some other embodiments, the non-miscible solution is dispensed onto a subset of features comprising a droplet. In other embodiments, the non-miscible solution is applied uniformly over the surface of the array forming a non-miscible bilayer in which the droplets are trapped. The non-miscible bilayer can then be evaporated to form a thin film over the surface or over a substantial part of the surface of the droplet. The non-miscible solution includes, but is not limited to, mineral oil, vegetable oil, silicone oil, paraffin oil, natural or synthetic wax, organic solvent that is immiscible in water or any combination thereof. One skilled in the art will appreciate that depending on the composition of the oils, some oils may partially or totally solidify at or below room temperature. In some embodiments, the non-miscible solution may be a natural or synthetic wax such as paraffin hydrocarbon. Paraffin is an alkane hydrocarbon with the general formula $C_nH_{2n+2}$. Depending on the length of the molecule, paraffin may appear as a gas, a liquid or a solid at room temperature. Paraffin wax refers to the solids with $20 \leq n \leq 40$ and has a typical melting point between about 47° C. to 64° C. Accordingly, in some embodiments, the support may be stored capped with a wax. Prior to use, heat may be applied to the support to allow the wax to turn into a liquid wax phase coating the support.

In some aspects of the invention, in subsequent steps, a solvent or an aqueous solution may be added to the droplet having a non-miscible solution at its surface. Aqueous solution may be added, for example, to initiate a reaction, to adjust a volume, to adjust a pH, to increase or decrease a solute concentration, etc. One would appreciate that the aqueous solution can penetrate the non-miscible layer using different mechanisms. For example, if using an inkjet head device, the aqueous solution is ejected and the physical momentum of the ejected droplet will enable the aqueous solution to cross the non-miscible layer. Other mechanisms may employ additional forces, such as for example magnetic and/or electrostatic forces and/or optical forces. The optical and magnetic forces can be created simultaneously or independently of one another. Furthermore, the mechanism can utilize coupled magneto-optical tweezers. In some embodiments, the aqueous solution to be dispensed contains magnetic nanoparticles and a magnetic force can be used to help penetration of the non-miscible layer. Alternatively, the aqueous solution carries an electrostatic charge and an external applied electric field can be used to achieve penetration of the non-miscible layer.

Yet, in another aspect of the invention, the size of the droplet is continuously or frequently monitored, One should appreciate that the size of the droplet is determined by the volume and by the surface tension of the solution. Accordingly, loss of volume can be detected by a decrease of the droplet footprint or radius of the droplet footprint. For example, using an optical monitoring system, through a microscope lens and camera system, the size or footprint of the droplet can be determined and the volume of the droplet can be calculated. In some embodiments, the volume of the droplet or the radius of the droplet is monitored every second or every millisecond. One would appreciate that the magnitude of the evaporation rate of the solvent (e.g. water) from the droplet of interest depends in part on the temperature and thus increases with increasing temperatures. For example, during amplification by thermocycling or during denaturation of the double-stranded complexes, increase of temperature will result in the rapid evaporation of the droplet. Therefore, the volume of the droplet can be monitored more frequently and the droplet volume can be adjusted by re-hydration more frequently. In the event of volume fluctuation such as loss of volume, sub-pica to nano volumes of solvent (e.g. water) can be dispensed onto the droplet or to the discrete feature comprising the droplet. Solvent or water volumes of about 0.5 pL, of about 1 pL, of about 10 pL, of about 100 pL, of about 1 nL, of about 10 nL, of about 100 nL can be dispensed this way. Solvent or water volumes may be delivered by any conventional delivery means as long that the volumes are controlled and accurate. In a preferred embodiment, water is dispensed using an inkjet device. For example, a typical inkjet printer is capable of producing droplets volumes ranging from about 1.5 pL to about 10 pL, while other commercial ultrasonic dispensing techniques can produce droplets volumes of about 0.6 pL. In some embodiments, water is added in a rapid series of droplets. In some embodiments, water is dispensed when registering a loss of volume of more than 10%, of more than 25%, of more than 35%, of more than 50%.

In another embodiment, the evaporation rate can be limited by adding a compound having a high boiling point component to the droplet(s) of interest, provided that the presence of the compound does not inhibit the enzymatic reactions performed on the substrate. The boiling point of a liquid is the temperature at which the liquid and vapor phases are in equilibrium with each other at a specified pressure. When heat is applied to a solution, the temperature of the solution rises until the vapor pressure of the liquid equals the pressure of the surrounding gases. At this point, vaporization or evaporation occurs at the surface of the solution. By adding a high boiling point liquid to the droplet of interest, evaporation of the water content of a droplet may be substantially reduced (see U.S. Pat. No. 6,177,558). In some embodiments, the high boiling point solution is a solvent. In some embodiments, the high boiling point liquid has a boiling point of at least 100° C., at least 150° C., at least 200° C. In some embodiments, glycerol is added to the solution, increasing the boiling point. Accordingly, the solution containing the high boiling point liquid will evaporate at a much slower rate at room temperature or at reaction conditions such as thermocycling, extension, ligation and denaturation.

In other embodiments, evaporation rate is limited by raising the vapor rate or humidity surrounding the droplet. This can be performed, for example, by placing "sacrificial" droplets around or in close proximity to the droplet of interest (e.g. around or in close proximity of a droplet comprising the oligonucleotides) (see for example, Berthier E. et al., Lab Chip, 2008, 8(6):852-859).

Some aspects of the invention relate to devices to control the humidity and/or the evaporation rate. In some embodiments, the surface or solid support is enclosed in a closed container to limit the evaporation. For example, humidity control can be achieved on a microvolume sealed plate. A substrate or support can be provided, the substrate having defined features such that volumes of reactions can be deposited in such features via, for example, an inkjet and inkjet-like liquid dispensing technology. A lid can be used to seal such reaction volumes by either applied pressure or using a lid with a pressure-sensitive adhesive on the contacting side to the substrate. In some embodiments, the density of these features can be at least 10 features per $cm^2$, at least 100 features per $cm^2$, at least 1,000 features per $cm^2$, at least 10,000 features per $cm^2$, at least 100,000 features per $cm^2$, at least 1,000,000 features per $cm^2$. The features can have diameter (width and length) dimensions from less than about 1 cm, less than about 1 mm, less than about 1 µm. The depth of the features can have dimensions from less than about 1 cm, less than about 1 mm, less than about 1 µm. The width, length, and depths of the features can differ from feature to feature. The features geometry can be complex, including lines, spirals, bends (at all possible angles from 0.01 degrees to 179.99 degrees) or any combination of such complex geometries.

In another embodiment, the substrate is flat with reaction volumes (e.g. droplets) set up on a surface of the substrate. The lid is designed to have features that from containers or vessels for reaction volumes. The reaction volumes can be created on the substrate using inkjet and inkjet-like liquid manipulation technologies. The lid can be sealed against the substrate by either applied pressure or using a lid or substrate with a pressure-sensitive adhesive on the contacting side to the substrate.

Aspects of the invention relate to feedback controlled humidity devices, systems and methods. In some embodiments, the device comprises a confinement chamber structure. A volume of a mixture of different gases, such as oxygen, nitrogen, argon, helium, water vapor, solvent vapor, and any other desirable gases, can be maintained inside a confinement chamber structure consisting of walls. In some embodiments, openings on the wall allow introduction and removal of different components of the gases to achieve the desired composition of the gas mixture in the volume. Additional openings can be used to serve as measurement or sampling ports to examine the condition or composition of the gas in the volume. A substrate carrying small reaction volumes (e.g. droplets) deposited by, for example, an inkjet or inkjet-like liquid dispensing technology can be placed inside the chamber's volume.

The chamber's volume can be further confined by a lid. In some embodiments, the lid is temperature controlled. The lid can be made of a material that is optically transparent, such as glass. The heating of the lid can be accomplished via an electrically conductive layer of Indium in Oxide (ITO), and heated via Ohmic heating. Other heating or cooling methods are also possible, for example, via forced fluid flow. The chamber's volume can be further confined by a bottom. In some embodiment, the bottom is temperature controlled. In some embodiments, the volume is modulated to contain an environment that has the exact molar ratio of different gas mixtures. In a preferred embodiment, the molar ratio of water vapor and carrier gas (air, helium, argon, nitrogen, or any other desirable gas, including solvent vapors) can be controlled, together with the temperature of the volume, to allow an equilibrium between water or solvent evaporation and condensation on the surface of the substrate. This equilibrium allows the reaction volumes on the substrate to be maintained at the desirable steady volume over an appropriate period of time. The appropriate period of time can be in the range of seconds, minutes, hours or days. One skilled in the art would appreciate that the droplets volumes can be maintained, decreased or increased by controlling evaporation and/or condensation. For example evaporation of the reaction volumes on the substrate is induced to, for example, achieve and/or control sample concentration and/or decrease the reaction volumes. Yet in other embodiments, condensation of the reaction volumes on the substrate is induced to, for example, achieve and/or control sample dilution and/or increase reaction volumes. One would appreciate that it is Important to control condensation when increasing reaction volumes. In some embodiments, condensation can be controlled by periodic humidity compensation. For example, by increasing the temperature on the substrate and/or lowering the humidity in the chamber, evaporation can be induced over a short period of time (in the range of ms, s or min). The evaporation of small satellite droplets (e.g. off target droplets) will take place before evaporation of larger droplets (e.g., reaction volumes). Since the evaporation rate (by volume) is proportional to droplets surface areas, and smaller droplets having higher surface-to-volume ratio evaporate first. In other embodiments, condensation may be controlled by controlling substrate's surface properties such as hydrophilicity/hydrophobicity. One skilled in the art will appreciate that condensation or droplet growth is characterized by nucleation of the droplet at nucleation sites. The rate of nucleation is a function of the surface tension and the wetting angle. Accordingly, surfaces promoting nucleation have a wetting-contact angles greater than zero. In some embodiments, condensation can be controlled by designing off-target areas on the surface (such as interfeatures) having surface properties impairing nucleation. For example, the substrate's surface can be treated so that off-target areas are more hydrophobic than areas where droplet growth is desired. In other embodiments, the off-target areas surfaces are designed to be smooth so that no nucleation is reduced.

In some aspects of the invention, the reaction volumes are controlled via a feedback control. In some embodiments, one or more monitoring isolated volumes (e.g. monitoring droplets) are used to monitor a plurality of isolated reaction volumes (e.g. droplets comprising predefined oligonucleotide sequences) on a support. In some embodiments, a first support is provided which comprises a plurality of reaction droplets and a second support is provided comprising at least one monitoring droplet. Preferably, the at least one monitoring droplet has an identical surface-to-volume ratio than at least one of the reaction droplet of interest and an identical solvent composition. Accordingly, modification of the reaction volume of the monitoring droplet is indicative of the modification of volume of the at least one droplet of interest. In some embodiments, the reaction droplets and monitoring droplets are placed on the same support.

In some embodiments, the molar ratio of the mixture of gases is measured using a cold mirror setup. An optically reflective surface can be placed on the bottom surface, next to the substrate. The mirror can be of a similar material and similar thickness to the substrate to best mimic the thermal behavior of the substrate. The reflective surface on the mirror can be on the top surface or on the bottom surface. In some embodiments, the mirror is placed on the same substrate as the reaction volumes. In some embodiments areas on the substrate can be made to act as mirrors to provide multiple measurement locations on the substrate. An optical assembly, consisting of a source, optical train, and a detector can be placed outside of the chamber's volume. In some embodiments, measure of the fogging or condensation of water fine water droplets onto a mirror is used to measure the condensation or the evaporation rate. Condensation condition on the mirror can be detected by measuring the intensity of the optical beam reflected off the surface. The beam can be modulated in time and wavelength, via the modulation of the source to achieve higher signal to noise ratios. In preferred embodiments, the system comprises a control loop. In an exemplary embodiment, the control loop includes a detector which feeds measured optical intensities to a signal conditioning circuit. The output of the signal conditioning circuit is used by the cold mirror logic to determine the condensation state on the mirror, and calculate molar ratio of the mix of gases in the volume using other inputs such as temperature, pressure etc. The system comprises a temperature sensor, pressure sensor, and/or any other suitable sensors. The humidity and temperature logic determines the actuation of humidifier, dehumidifier, and/or temperature controllers to effectuate the desirable conditions determined by the cold mirror logic.

In some embodiments, the reaction volumes contain the necessary reagents to allow enzyme mediated biochemical reactions to take place between the molecular population inside the reaction volume (e.g. droplet) and the molecular population present on the wetted surface in contact with the reaction volume. One would appreciate that the reaction volume can be used to carry out a variety of reactions including, but no limited to, amplification, hybridization, extension, ligation, sequencing, in-vitro transcription, in-vitro translation, or any other reaction of interest. The molecular population may contain nucleic acids, DNA, RNA, oligonucleotides, proteins, dNTPs, salts, buffer components, detergents, and/or any other appropriate component. The reaction volume may comprises an enzyme, such as a polymerase, a ligase, a CEL1-like endonuclease, a nuclease, mixtures of such enzymes, and/or any other appropriate enzymes. In some embodiments, the products of the enzyme mediated biochemical reaction can include contain nucleic acids, DNA, RNA, oligonucleotides, proteins, labeled nucleic acids, amplified nucleic acid (e.g. clonal amplification of a selected population of nucleic acid), assembled nucleic acids etc.

In some aspects of the invention, the reagents in the reaction volumes promote oligonucleotide or polynucleotide assembly. In some embodiments, the reaction volumes may contain two or more populations of single-stranded oligonucleotides having predefined sequences in solution. The populations of oligonucleotides can hybridize to a single-stranded oligonucleotide attached to the wetted surface thereby forming double-stranded hybrids or duplexes attached to the surface. In some embodiments, the double-stranded hybrids contain breaks and gaps in the phosphodiester backbone, formed at the junctions of different oligonucleotide populations. In some embodiments, a polymerase and dNTPs and other necessary components are added to fill the gaps in the backbone. In other embodiments, a ligase and other necessary components are added to mend breaks in the backbone.

In other embodiments, the reaction volumes may contain two or more populations of oligonucleotides in solution, each population of oligonucleotide having predefined sequence. In some embodiments, each population of oligonucleotide has a sequence complementary to the an another population of oligonucleotides. In this manner, the populations of oligonucleotides can hybridize to form double stranded hybrids or duplexes in solution. The hybrids may contain breaks and gaps in the phosphodiester backbone, formed at the junctions of different oligonucleotide populations. In some embodiments, a polymerase and dNTPs and other necessary components are added to fill the gaps in the backbone. In other embodiments, a ligase and other necessary components are added to mend breaks in the backbone.

Amplification Reactions

Aspects of the invention provide methods for the amplification of one or more single-stranded oligonucleotide on the support. Oligonucleotides may be amplified before or after being detached from the support and/or eluted in a droplet. Preferably, the oligonucleotides are amplified on the solid support. One skilled in the art will appreciate that oligonucleotides that are synthesized on solid support will comprise a phosphorylated 3' end or an additional 3'-terminal nucleoside (e.g., T). The 3'-phosphorylated oligonucleotides are not suitable for polynucleotide assembly as the oligonucleotides cannot be extended by polymerase. In preferred aspects of the invention, the oligonucleotides are first amplified and the amplified products are assembled into a polynucleotide. Accordingly, aspect of the invention provides methods wherein a set or subset of oligonucleotides, that are attached to at a set of subset of features of the support, are amplified by locally delivering sub-microvolumes at addressable discrete features. The term "amplification" means that the number of copies of a nucleic acid fragment is increased. As noted above, the oligonucleotides may be first synthesized onto discrete features of the surface, may be deposited on the substrate or may be deposited on the substrate attached to nanoparticles. In a preferred embodiment, the oligonucleotides are covalently attached to the surface or to nanoparticles deposited on the surface. In an exemplary embodiment, locations or features comprising the oligonucleotides to be amplified are first selected. In a preferred embodiment, the selected features are in close proximity to each others on the support. Aqueous solution is then deposited on the selected feature thereby forming a droplet comprising hydrated oligonucleotides. One would appreciate that each droplet is separated from the other by surface tension. In some embodiments, the solution can be water, buffer or a solution promoting enzymatic reactions. In an exemplary embodiment, the solution includes, but is not limited to, a solution promoting primer extension. For example, the solution may be composed of oligonucleotides primer(s), nucleotides (dNTPs), buffer, polymerase and cofactors. In other embodiments, the solution is an alkaline denaturing solution. Yet, in other embodiments, the solution may comprise oligonucleotides such as complementary oligonucleotides.

In some embodiments, oligonucleotides or polynucleotides are amplified within the droplet by solid phase PCR thereby eluting the amplified sequences into the droplet. In other embodiments, oligonucleotides or polynucleotides are first detached form the solid support and then amplified. For example, covalently-attached oligonucleotides are translated into surface supported DNA molecules through a process of gaseous cleavage using amine gas. Oligonucleotides can be cleaved with ammonia, or other amines, in the gas phase whereby the reagent gas comes into contact with the oligonucleotide while attached to, or in proximity to, the solid support (see Boal et al., Nucl. Acids Res, 1996, 24(15): 3115-7), U.S. Pat. Nos. 5,514,789; 5,738,829 and 6,664, 388). In this process, the covalent bond attaching the oligonucleotides to the solid support is cleaved by exposing the solid support to the amine gas under elevated pressure and/or temperature. In some embodiments, this process may be used to "thin" the density of oligonucleotides at specific features.

One would appreciate that amplification occurs only on features comprising hydrated template oligonucleotides (i.e. local amplification at features comprising a droplet volume). Different set of features may be amplified in a parallel or sequential fashion with parallel or sequential rounds of hydrating (i.e. dispensing a droplet volume on a specific feature), amplifying oligonucleotides and drying the set of features. In some embodiments, the support is dried by evaporating liquid in a vacuum while heating. Thus, after each round of amplification, the support will comprise a set of droplets containing oligonucleotides duplexes. The complementary oligonucleotides can be released in solution within the droplet and be collected. Alternatively, complementary oligonucleotides may be dried onto the discrete features for storage or further processing. Yet, complementary oligonucleotides can be subjected to further reactions such as error filtration and/or assembly. In some embodiments, a different set or subset of features can then be hydrated and a different set or subset of template oligonucleotides can be amplified as described herein. In the case of the enzymatic amplification, the solution includes but is not limited to primers, nucleotides, buffers, cofactors, and enzyme. For example, an amplification reaction includes DNA polymerase, nucleotides (e.g. dATP, dCTP, dTTP, dGTP), primers and buffer.

According to some aspects of the invention, hydrated oligonucleotides can be amplified within the droplet, the droplet acting as a virtual reaction chamber. In some embodiments, the entire support or array containing the discrete features is subjected to amplification. In other embodiments, one or more discrete features are subjected to amplification. Amplification of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from wide spectrum (100 nm to 100,000 nm, i.e. from ultraviolet to infrared). In some embodiments, the feature on which the droplet is spotted comprises an optical absorber or indicator. In some other embodiments, optical absorbent material can be added on the surface of the droplet. In some embodiments, the solid support is cooled by circulation of air or fluid. The energy to be deposited can be calculated based on the absorbance behavior. In some embodiments, the temperature of the droplet can be modeled using thermodynamics. The temperature can be measured by art LCD like material or any other in-situ technology. In some embodiments, the solid support is cooled by circulation of air or fluid. For example, the whole support can be heated and cooled down to allow enzymatic reactions to take place.

In some embodiments, a selected set of features may be protected from hydration by using an immiscible fluid system as described above. An immiscible fluid system, such as oil and aqueous reagents, can be used to achieve passivation of sites on which reactions take place.

In some embodiments, the oligonucleotides may comprise universal (common to all oligonucleotides), semi-universal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially.

In some embodiments, primers/primer binding site may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide. In some embodiments, after amplification, the pool of nucleic acids may be contacted with one or more endonucleases to produce double-stranded breaks thereby removing the primers/ primer binding sites. In certain embodiments, the forward and reverse primers may be removed by the same or different restriction endonucleases.

Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJf, Exonuclease I, Exonuclease T, S1 nuclease, P1 nuclease, mung bean nuclease, T4 DNA polymerase, CEL I nuclease, etc.) may be used to produce blunt ends. Alternatively, the sticky ends fat med by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Beg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 Aar I; and enzymes that produce a blunt end, such as, for example, Mly I and Btr I. Type-IIs endonucleases are commercially available and are well known in the art (New England Biolabs, Beverly, Mass.).

After amplification, the polymerase may be deactivated to prevent interference with the subsequent steps. A heating step (e.g. high temperature) can denature and deactivate most enzymes which are not thermally stable. Enzymes may be deactivated in presence (e.g. within the droplet) or in the absence of liquid (e.g. dry array). Heat deactivation on a dry support has the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

The complementary oligonucleotides produced by amplification can be released in solution within the droplet by way of stringent melt. The conditions for stringent melt (e.g., a precise melting temperature) can be determined by observing a real-time melt curve. In an exemplary melt curve analysis, PCR products are slowly heated in the presence of double-stranded DNA (dsDNA) specific fluorescent dyes SYBR Green, LCGreen, SYTO9 or EvaGreen). With increasing temperature the dsDNA denatures (melts), releasing the fluorescent dye with a resultant decrease in the fluorescent signal. The temperature at which dsDNA melts is determined by factors such as nucleotide sequence, DNA length and GC/AT ratio. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available and may be in which G-C stacking interactions, solvent effects, the desired assay temperature and the like are taken into account. Melt curve analysis can detect a single base difference. Various methods for accurate temperature control at individual features can be used as disclosed herein.

One method to control the temperature of the surface droplets is by using a scanning optical energy deposition setup. For example, a Digital Micromirror Device (DMD) can be used for temperature control. DMD is an optical semiconductor. See, for example, U.S. Pat. No. 7,498,176. In some embodiments, a DMD can be used to precisely heat selected features or droplets on the solid support. The DMD can be a chip having on its surface several hundred thousand microscopic mirrors arranged in a rectangular array which correspond to the features or droplets to be heated. The mirrors can be individually rotated (e.g., ±10-12°), to an on or off state. In the on state, light from a light source (e.g., a bulb) is reflected onto the solid support to heat the selected spots or droplets. In the off state, the light is directed elsewhere (e.g., onto a heatsink). In one example, the DMD can consist of a 1024×768 array of 16 μm wide micromirrors. These mirrors can be individually addressable and can be used to create any given pattern or arrangement in heating different features on the solid support. The features can also be heated to different temperatures, e.g., by providing different wavelengths for individual spots, and/or controlling time of irradiation.

In some embodiments, the entire support or array containing the discrete features is heated to a denaturing temperature. Preferably, denaturation of double stranded nucleic acid is performed in solution (e.g. within the droplet). During the heat denaturation step, the temperature of the support is raised to a stringent melt temperature or to a denaturing temperature (95° C. to 100° C.). Elevating the temperature of the support to a denaturing or stringent melt temperature allows the homoduplexes to dissociate into single strands before complete evaporation of the droplet volume. Heating the substrate results in the denaturation and evaporation of the solution, resulting in dried single-stranded oligonucleotides onto the discrete features. At this point, the entire support may be cooled down to a predefined hybridization or annealing temperature. A set of selected features or the totality of the features may be re-hydrated by addition of the appropriate annealing buffer (at the appropriate annealing temperature) at the selected features or on the entire support. Single stranded oligonucleotides may then be resuspended and allowed to diffuse and to hybridize or anneal to form the double-stranded oligonucleotides (homoduplexes or heteroduplexes).

Accordingly, some aspects of the invention relate to the recognition and local removal of double-stranded oligonucleotides containing sequence mismatch errors at specific features. In one preferred embodiment of the invention, mismatch recognition can be used to control the errors generated during oligonucleotide synthesis, gene assembly, and the construction of longer polynucleotides. After amplification, the totality of the features or a set of the features comprising oligonucleotide duplexes are first subjected to round(s) of melting and annealing as described above. Subsequently, a first set of discrete features comprising oligonucleotides having same theoretical Tm are hydrated and oligonucleotides are allowed to anneal under annealing conditions. Hydrated features are then subjected to a first stringent melt condition (condition 1). It would be appreciate that for sequential local error removal, it is preferable to first start with the stringent melt conditions corresponding to the lowest Tm (Tm(1)) and conclude with stringent melt conditions corresponding to the higher Tm(Tm(n)). In other embodiments, the totality of the features of the support may be hydrated and subjected to the lowest Tm temperature. Under the first specific stringent melt conditions Tm(1), only the oligonucleotides that are hybridized in an unstable duplex will de-hybridize. De-hybridized oligonucleotides may be removed for example, using a vacuum or may be washed away. In a subsequent step, the support may be dried out and a second discrete features comprising oligonucleotides having a Tm higher than Tm(1) (for example (Tm(2)) are selectively rehydrated and allowed to anneal under annealing conditions. In other embodiments, the totality of the features of the support may be re-hydrated and subjected to the second Tm temperature Tm(2) wherein Tm(2) is higher than Tm(1). These steps of selective hydration, annealing, stringent melt and removal of error-containing oligonucleotides can be repeated multiple times until all discrete features have been subjected to the appropriate stringent melt condition (theoretically 80-100° C.). Alternatively, a mismatch detecting endonuclease may be added to the droplet solution. In an exemplary embodiment, a Surveyor™ Nuclease (Transgenomic Inc.) may be added to the hydrated feature containing the oligonucleotide duplexes. Surveyor™ Nuclease is a mismatch specific endonuclease that cleaves all types of mismatches such as single nucleotide polymorphisms, small insertions or deletions. Addition of the endonuclease results in the cleavage of the double-stranded oligonucleotides at the site of the mismatch. The remaining portion of the oligonucleotide duplexes can then be melted at a lower and less stringent temperature (e.g. stringent melt) needed to distinguish a single base mismatch. One wore appreciate that the error removal steps as well as the amplification steps may be repeated in a sequential fashion or in a highly parallel fashion by controlling the temperature of the entire support or of the independent features as described above.

One skilled in the art will appreciate that releasing oligonucleotides from the solid support can be achieved by a number of different techniques which will depend on the technique used to attach or synthesize the oligonucleotides on the solid support. Preferably, the oligonucleotides are attached or synthesized via a linker molecule and subsequently detached and released. In some embodiments, a plurality of oligonucleotides may be attached or synthesized to the support, cleaved at a cleavable linker site and released in solution. For example, U.S. Pat. No. 7,563,600 discloses a cleavable linker having a succinate moiety bound to a nucleotide moiety such that the cleavage produces a 3'-hydroxy-nucleotide. The succinate moiety is bound to solid support through an ester linkage by reacting the succinate moieties with the hydroxyl on the solid support. US Patent application discloses sulfonyl cleavable linkers comprising a linker hydroxyl moiety and a base-labile cleaving moiety. A phosphorous-oxygen bond is formed between phosphorous of the sulfonyl amidite moieties and oxygen of the hydroxyl groups at known location of the support. In some embodiments, the oligonucleotides are attached or synthesized using a photo-labile linker (see for example Tosquellas et al., Nucl. Acids Res., 1998, Vol, 26, pp 2069-2074). In some instances, the photolabile linker can be rendered labile by activation under an appropriate chemical treatment. For example, U.S. Pat. No. 7,183,406 discloses a safety-catch linker which is stable under the oligonucleotide synthesis conditions and that is photolabile after treatment with trifluoroacetic acid. Oligonucleotides linked with a photo-labile linker can then be released by photolysis. Using photolabile linkers, it is therefore possible to selectively release in solution (e.g. in a droplet) specific oligonucleotides at predetermined features. The oligonucleotides released in solution may then be brought into contact for further processing (hybridization, extension, assembly, etc.) by merging droplets of moving the oligonucleotides from one feature to a next feature on a solid support.

One skilled in the art will appreciate that DNA microarrays can have very high density of oligonucleotides on the surface (approximately 108 molecules per feature), which can generate steric hindrance to polymerases needed for PCR. Theoretically, the oligonucleotides are generally spaced apart by about 2 nm to about 6 nm. For polymerases, a typical 6-subunit enzyme can have a diameter of about 12 nm. Therefore the support may need to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligonucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

Nucleic Acid Assembly

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences.

In some embodiments, the assembly procedure may include several parallel and/or sequential reaction steps in which a plurality of different nucleic acids or oligonucleotides are synthesized or immobilized, amplified, and are combined in order to be assembled (e.g., by extension or ligation as described herein) to generate a longer nucleic acid product to be used for further assembly, cloning, or other applications (see US provisional application 61/235,677 and PCT application PCT/US09/55267 which are incorporate herein by reference in their entirety). Amplification and assembly strategies provided herein can be used to generate very large libraries representative of many different nucleic acid sequences of interest.

Accordingly, one aspect of the technology provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, more than about 99%, or more of the sequences are predetermined sequences of interest).

In some embodiments, the methods and devices provided herein use oligonucleotides that are immobilized on a surface or substrate (e.g., support-bound oligonucleotides). Support-bound oligonucleotides comprise for example, oligonucleotides complementary to construction oligonucleotides, anchor oligonucleotides and/or spacer oligonucleotides.

Some aspects of the invention relate to a polynucleotide assembly process wherein synthetic oligonucleotides are designed and used as templates for primer extension reactions, synthesis of complementary oligonucleotides and to assemble polynucleotides into longer polynucleotides constructs. In some embodiments, the method includes synthesizing a plurality of oligonucleotides or polynucleotides in a chain extension reaction using a first plurality of single-stranded oligonucleotides as templates. As noted above, the oligonucleotides may be first synthesized onto a plurality of discrete features of the surface, or may be deposited on the plurality of features of the support. The support may comprise at least 100, at least 1,000, at least $10^4$, at least $10^5$, at least $10^6$, at least $10^7$, at least $10^8$ features. In a preferred embodiment, the oligonucleotides are covalently attached to the support. In preferred embodiments, the pluralities of oligonucleotides are immobilized to a solid surface. In a preferred embodiment, each feature of the solid surface comprises a high density of oligonucleotides having a different predetermined sequence (e.g., approximately $10^6$-$10^8$ molecules per feature).

In some embodiments, pluralities of different single-stranded oligonucleotides are immobilized at different features of a solid support. In some embodiments, the support-bound oligonucleotides may be attached through their 5' end. In a preferred embodiment, the support-bound oligonucleotides are attached through their 3' end. In some embodiments, the support-bound oligonucleotides may be immobilized on the support via a nucleotide sequence (e.g. degenerate binding sequence), linker or spacer (e.g. photo-cleavable linker or chemical linker). It should be appreciated that by 3' end, it is meant the sequence downstream to the 5' end and by 5' end it is meant the sequence upstream to the 3' end. For example, an oligonucleotide may be immobilized on the support via a nucleotide sequence, linker or spacer that is not involved in hybridization. The 3' end sequence of the support-bound oligonucleotide referred then to a sequence upstream to the linker or spacer.

In certain embodiments, oligonucleotides may be designed to have a sequence that is identical or complementary to a different portion of the sequence of a predetermined target polynucleotide that is to be assembled. Accordingly, in some embodiments, each oligonucleotide may have a sequence that is identical or complementary to a portion of one of the two strands of a double-stranded target nucleic acid. As used herein, the term "complementary" refers to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules.

In some embodiments, the plurality of construction oligonucleotides are designed such as each plurality of construction oligonucleotides comprising a sequence region at its 5' end that is complementary to sequence region of the 5' end of another construction oligonucleotide and a sequence region at its 3' end that is complementary to a sequence region at a 3' end of a different construction oligonucleotide. As used herein, a "construction" oligonucleotide refers to one of the plurality or population of single-stranded oligonucleotides used for polynucleotide assembly. The plurality of construction oligonucleotides comprises oligonucleotides for both the sense and antisense strand of the target polynucleotide. Construction oligonucleotides can have any length, the length being designed to accommodate an overlap or complementary sequence. Construction oligonucleotides can be of identical size or of different sizes. In preferred embodiments, the construction oligonucleotides span the entire sequence of the target polynucleotide without any gaps. Yet in other embodiments, the construction oligonucleotides are partially overlapping resulting in gaps between construction oligonucleotides when hybridized to each other. Preferably, the pool or population of construction oligonucleotides comprises construction oligonucleotides having overlapping sequences so that construction oligonucleotides can hybridize to one another under the appropriate hybridization conditions. One would appreciate that each internal construction oligonucleotides will hybridize to two different construction oligonucleotide whereas the construction oligonucleotides at the 5' and/or 3' end will hybridize each to a different (or the same) internal oligonucleotide(s). Hybridization and ligation of the overlapping construction oligonucleotides will therefore result in a target polynucleotide having a 3' and/or a 5' overhang. Yet in some embodiments, the resulting target polynucleotide may comprise blunt end at its 5' or/and 3' terminus. In some embodiments, if the target polynucleotide is assembled from N construction oligonucleotides, 1 to N pluralities of different support-bound single-stranded oligonucleotides are designed such as the first plurality of construction oligonucleotides comprises at its 5' end a sequence region that is complementary to a sequence region at the 5' end of an anchor oligonucleotide and wherein a N plurality of construction oligonucleotides comprises at its 3' end a sequence region that is complementary to a 3' end sequence region of the (N–1) construction oligonucleotide. In some embodiments, the first plurality of oligonucleotides has a 5' end that is complementary to the 5' end of a support bound anchor single-stranded oligonucleotide. As used herein, the anchor oligonucleotide refers to an oligonucleotide designed to be complementary to at least a portion of the target polynucleotide and may be immobilized on the support. In an exemplary embodiment, the anchor oligonucleotide has a sequence complementary to the 5' end of the target polynucleotide and may be immobilized on the support.

In some aspects of the invention, the reagents in the reaction volumes promote oligonucleotide or polynucleotide assembly by polymerase chain extension or ligase-based assembly. In some embodiments, the reaction volumes may contain two or more populations of single-stranded oligonucleotides having predefined sequences in solution. The populations of oligonucleotides can hybridize to a single-stranded oligonucleotide attached to the wetted surface thereby forming double-stranded hybrids or duplexes attached to the surface. In some embodiments, the double-stranded hybrids contain breaks and gaps in the phosphodiester backbone, formed at the junctions of different oligonucleotide populations. In some embodiments, a polymerase and dNTPs and other necessary components are added to fill the gaps in the backbone. In other embodiments, a ligase and other necessary components are added to mend breaks in the backbone.

In some embodiments, two different or more oligonucleotides or polynucleotides may be immobilized or synthesized at the same location (or feature) on the solid support thereby facilitating their interaction after amplification within the same droplet. See e.g. US 2004/0101894. In some embodiments, droplets are merged to form bigger droplets by adding, or spotting additional "merger" droplets or volumes in between or around the appropriate original droplets. Two droplets, or isolated volumes can therefore merge if a "merger" droplet or volume is created and expanded until the merge takes place. The resultant merged volume will encompass the first stage droplets or first isolated volumes. The volume and location of the resulting merged volume can vary. The merged volumes (e.g. second stage droplet) can occupy a footprint that is the combination of all volumes (e.g. first stage droplets and merger droplet). Alternatively, the merged volumes can occupy at least part of the footprint of one of the isolated volume (e.g. first or second isolated volume.

Some aspects of the invention, relate to the destination selection and routing of the isolated volumes and therefore to the control of the location or footprint of merged volumes. One would appreciate that as individual regions of the support are addressable, individual isolated volumes such as droplets may be controlled individually. In some embodiments, it is preferable to place isolated volumes onto adjacent regions or features to allow merging of the volumes. Yet, in other embodiments, isolated volumes are directed or routed to a pre-selected destination.). In some case, the merged volumes occupy the footprint of one of the isolated volume and extend to one or more smaller contact angle regions (SCA). In some embodiments, the substrate of the support is substantially planar and droplets are routed using a two-dimensional path (e.g. x, y axis). Droplets may be moved to bring them to selected locations for further processing, to be merged with a second isolated volume into a second stage droplet at preselected locations and/or during the transport, to remove some reactants from the droplet (referred herein "wash-in-transport' process).

In some embodiments, step-wise hierarchical and/or sequential assembly can be used to assemble oligonucleotides and longer polynucleotides. In a preferred embodiment, the methods use hierarchical assembly of two or more oligonucleotides or two or more nucleic acids subassemblies at a time. Neighboring droplets can be manipulated (move and/or merged, as described above) to merge following a hierarchical strategy thereby improving assembly efficiency. In some embodiments, each droplet contains oligonucleotides with predefined and different nucleic acid sequences. In some embodiments, two droplets are moved following a predefined path to an oligonucleotide-free position. In a preferred embodiment, the assembly molecules (e.g. oligonucleotides) are pre-arranged on the support surface at pre-determined discrete features.

One should appreciate that isolated volumes may be routed independently in a sequential or highly parallel fashion. Droplets may be routed using electrowetting-based techniques (see fix example, U.S. Pat. No. 6,911,132 and U.S. Patent Application 2006/0054503). Electrowetting principle is based on manipulating droplets on a surface comprising an array of electrodes and using voltage to change the interfacial tension. By applying an electric field (e.g. alternating or direct), the contact angle between the fluid and surfaces can be modified. For example, by applying a voltage, the wetting properties of a hydrophobic surface can become increasingly hydrophilic and therefore wettable. In some embodiments, the array of electrode is not in direct contact with the fluid. In some embodiments, droplets are moved using a wettability gradient. It has been shown that droplets placed on wettability gradient surfaces typically move in the direction of increasing wettability (see Zielke and Szymczyk, Eur. Phys. J. Special Topics, 166, 155-158 (2009)). In other embodiments, droplets may be moved using a thermal gradient. When placed on a thermal gradient, droplets move from higher temperature locations towards lower temperature locations. Moving droplets using electrowetting, temperature gradients and wettability gradients depend on the liquid (e.g. aqueous, non-aqueous, solute concentration), the size of the droplets and/or the steepness of the gradient.

One skilled in the art will appreciate that most of the electrowetting merging and mixing strategies rely on the fact that droplets have identical volumes before merging. In some aspects of the invention, routing of the droplet and merging is controlled by the using different size droplets. In a preferred embodiment, the footprint of the merged volume is controlled by the size of the droplets before merging. In some embodiments, the method comprises moving the content of smaller volume droplets to the position of larger volume droplets.

One skilled in the art will appreciate that the principle described herein can be applied to move liquid volumes such as droplets on the support along a predetermined path and to determine the exact location of the merged volume. In some embodiments, the content of the smaller volumes may repeatedly be moved to the position of larger volumes in order to move liquid volumes over a distance that is larger than a merger region.

Reactions, include, but are not limited to incubation, enzymatic reactions, dilution, mixing, error reduction and/or assembly. Although the figures show a linear, one dimensional, path, it should be appreciated that the droplet can be moved anywhere on the support surface. In some embodiments, the droplets are moved in a two dimensional direction. Any other operations derived form this protocol can be envisioned. For example, droplets can be deposited sequentially, simultaneously, or in a parallel fashion. Droplets may contain only water and may be used as dilution droplets, Other droplets may contain a solute. Droplet content may be mixed by passive diffusion or active mixing. In some embodiments, at least two droplets are moved independently following a similar path and are then moved towards a feature that is referred as a reaction feature wherein the droplets are merged. The first and second droplet paths across the substrate may follow the same direction or may follow opposite directions. For example, a first droplet may be moved toward a stationary second droplet or the first and the second droplet may be moved toward each others. Moreover, if two droplets have the same size, reduction of the size of one droplet will enable it, to move in the direction and to the location of the larger volume. Reduction of the size of the droplet can be achieved by evaporation. Evaporation of liquid may be achieved using any technique known in the art. For example, the isolated liquid volume to be decreased may be heated to induce or accelerate evaporation. Alternatively, to merge a first droplet at the location of a second droplet, liquid may be added to the second droplet to increase its size comparatively to the first droplet.

Another benefit of the droplet movement process described herein is the implementation of a "wash" operation (referred herein as wash-in-transportation). The movement of the liquid away from a surface feature allows the separation of the surface-bound molecules (e.g. oligonucleotides) from the molecules in solution. Hence, a wash operation is therefore implemented. For example, wash-in-transportation can be used to remove the template oligonucleotides form the complementary oligonucleotides after amplification. In some embodiments, "wash-in transportation" features or wash spots may be placed adjacent to features where oligonucleotide processing takes place.

In some embodiments, the "merger" droplets or the "anchor" droplet may contain or not contain enzyme (e.g. polymerase, ligase, etc.), additional oligonucleotides and all reagents to allow assembly by PCR or by ligation (enzymatic or chemical) or by any combination of enzymatic reaction. For example, oligonucleotides in a given droplet may hybridize to each other and may assemble by PCR or ligation. The bigger droplets or second stage droplets contain polynucleotides subassemblies and can be subsequently merged to form larger droplets or third stage droplet containing larger fragments. As used herein the term subassembly refers to a nucleic acid molecule that has been assembled from a set of oligonucleotides. Preferably, a subassembly is at least 2-fold or more long than the oligonucleotides. For example, a subassembly may be about 100, 200, 300, 400, 500, 600, or ore bases long. One should appreciate that the use of droplets as isolated reaction volumes enables a highly parallel system. In some embodiments, at least 100, at least 1,000 reactions can take place in parallel. In some embodiments, the primers are immobilized on the support in close proximity to the spots containing the oligonucleotides to be assembled. In some embodiments, the primers are cleaved in situ. In some embodiments, the primers are supported on the solid support. The primers may then be cleaved in situ and eluted within a droplet that will subsequently merged with a droplet containing solid supported or eluted oligonucleotides.

Some aspects of the invention relate to the transport of charged molecules such as nucleic acid (e.g. oligonucleotides or polynucleotides) to a selected destination or selected feature on a support within a fluid medium using a planar two dimensional path (x, y axis). Preferably the molecules are electrophoretically transported by polarization of the molecules of interest on application of a voltage, the charged molecule moving towards an electrode (anode or cathode). In some embodiments, the array comprises one or more preferably, a plurality of electrophoretic planar microfluidic units, each microfluidic unit comprising two electrodes. The electrodes system comprises at least one cathode and one anode. In some configurations, the cathode and anode are shared by a plurality of microfluidic units. In other configuration, the cathodes and anode are for a single microfluidic unit. The microfluidic units enable the displacement of charged molecules of interest according to an electrophoretic path. In some embodiments, each microfluidic unit comprises at least on channel. Preferably, each microfluidic unit is fluidly connected. For example, each microfluidic unit may be connected to another microfluidic unit, by a channel. In preferred embodiments, an aqueous buffer is utilized as the fluid in die device. In some embodiments, each microfluidic unit may comprise a capture site. In some embodiment, the capture site corresponds to an array feature. Yet in other embodiment, the capture site corresponds to an array interfeature. In some embodiments, the capture site comprises a material that capture charged molecules. In nucleic acids, the phosphate ion carries a negative charge. Accordingly, preferably the capture site comprises a material that capture negatively charged molecules. In some instances, the capture material may capture the charged molecules of interest by chemically interaction through covalent bonding, hydrogen bonding, ionic bonding, Vander Waals interactions, or other molecular interactions. Alternatively, the capture material does not interact with the molecules of interest but retards the molecule's electrophoretic transport. In some embodiments, at least a first feature and a second feature of the arrays are in fluid communication and the charged oligonucleotide or polynucleotide is moved between the first feature and a second feature by applying a voltage between the first and the second feature.

In certain embodiments, the oligonucleotides are designed to provide the full sense (plus strand) and antisense (minus strand) strands of the polynucleotide construct. After hybridization of the plus and minus strand oligonucleotides, double-stranded oligonucleotides are subjected to ligation in order to form a first subassembly product. Subassembly products are then subjected to ligation to form a larger nucleic acid or the full nucleic acid sequence.

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from Therms thermophiles, available from, for example, Eurogentec and GeneCraft); Pfu DNA ligase (a hyperthermophilic ligase from Pyrococcus furiosus); Taq ligase (from Thermus aquaticus), 9° N Ligase, Ampligase®, any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands at a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photochemical ligation reactions. It should be appreciated that in some embodiments chemical ligation can be used to produce naturally occurring phosphodiester internucleotide linkages, non-naturally-occurring phosphamide pyrophosphate internucleotide linkages, and/or other non-naturally-occurring internucleotide linkages.

In some embodiments, the process of chemical ligation may involve one or more coupling agents to catalyze the ligation reaction. A coupling agent may promote a ligation reaction between reactive groups in adjacent nucleic acids (e.g., between a 5'-reactive moiety and a 3'-reactive moiety at adjacent sites along a complementary template). In some embodiments, a coupling agent may be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation may be an autoligation reaction that does not involve a separate coupling agent. In autoligation, the presence of a reactive group on one or more nucleic acids may be sufficient to catalyze a chemical ligation between nucleic acid termini without the addition of a coupling agent (see, for example, Xu et al., (1997) Tetrahedron Lett. 38:5595-8). Non-limiting examples of these reagent-free ligation reactions may involve nucleophilic displacements of sulfur on bromoacetyl, tosyl, or iodo-nucleoside groups (see, for example, Xu et al., (2001) Nat. Biotech. 19:148-52). Nucleic acids containing reactive groups suitable for autoligation can be prepared directly on automated synthesizers (see, for example, Xu et al., (1999) Nuc. Acids Res. 27:875-81). In some embodiments, a phosphorothioate at a 3' terminus may react with a leaving group (such as tosylate or iodide) on a thymidine at an adjacent 5' terminus. In some embodiments, two nucleic acid strands bound at adjacent sites on a complementary target strand may undergo auto-ligation by displacement of a 5'-end iodide moiety tosylate) with a 3'-end sulfur moiety. Accordingly, in some embodiments the product of an auto ligation may include a non-naturally-occurring internucleotide linkage (e.g., a single oxygen atom may be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid may be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid may be ligated in a separate reaction containing phosphorylated oligonucleotides corresponding to the strand that is to be ligated and non-phosphorylated oligonucleotides corresponding to the complementary strand. The non-phosphorylated oligonucleotides may serve as a template for the phosphorylated oligonucleotides during a chemical ligation (e.g., using cyanogen bromide). The resulting single-stranded ligated nucleic acid may be purified and annealed to a complementary ligated single-stranded nucleic acid to form the target duplex nucleic acid (see, for example, Shabarova et al., (1991) Nucl. Acids Res. 19:4247-51).

In one aspect, a nucleic acid fragment may be assembled in a polymerase mediated assembly reaction from a plurality of oligonucleotides that are combined and extended in one or more rounds of polymerase-mediated extensions. In some embodiments, the oligonucleotides are overlapping oligonucleotides covering the full sequence but leaving single-stranded gaps that may be filed in by chain extension. The plurality of different oligonucleotides may provide either positive sequences (Plus strand), negative sequences (minus strand), or a combination of both positive and negative sequences corresponding to the entire sequence of the nucleic acid fragment to be assembled. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 5 and about 500 oligonucleotides long (e.g., between about 10 and 100, between about 10 and 75, between about 10 and 50, about 20, about 25, about 30, about 35, about 45, about 50, etc.). However, shorter, longer, or intermediate overlapping lengths may be used. It should be appreciated that overlaps between different input nucleic acids used in an assembly reaction may have different lengths.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'-5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium Thermus aquaticus); Pfu thermophilic DNA polymerase with a 3'→5' exonuclease/proofreading activity from Pyrococcus furiosus, available from for example Promega); VentR® DNA Polymerase and VentRO (exo-) DNA Polymerase (thermophilic DNA polymerases with or without a 3'→5' exonuclease/proofreading activity from Thermococcus litoralis; also known as Th polymerase); Deep VentR® DNA Polymerase and Deep VentR® (exo-) DNA Polymerase (thermophilic DNA polymerases with or without a 3'→5' exonuclease/proofreading activity from Pyrococcus species GB-D; available from New England Biolabs); KOD Hifi (a recombinant Thermnococcus kodakaraensis KODI DNA polymerase with a 3'→5' exonuclease/proofreading activity, available from Novagen,); BIO-X-ACT (a mix of polymerases that possesses 5'-3' DNA polymerase activity and 3'→5' proofreading activity); Menow Fragment (an N-terminal truncation of *E. coli* DNA Polymerase I which retains polymerase activity, but has lost the 5'→3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of Methanopyrus topoisomerase, with no exonuclease activity, available from Fidelity Systems); TopoTaq HiFi which incorporates a proofreading domain with exonuclease activity; Phusion™ (a Pyrococcus-like enzyme with a processivity-enhancing domain, available from New England Biolabs); any other suitable DNA polymerase, or any combination of two or more thereof.

In some embodiments, the polymerase can be a SDP (strand-displacing polymerase; e.g. an SDPe—which is an SDP with no exonuclease activity). This allows isothermal PCR (isothermal extension, isothermal amplification) at a uniform temperature. As the polymerase for example, Phi29, Bst) travels along a template it displaces the complementary strand (e.g., created in previous extension reactions). As the displaced DNAs are single-stranded, primers can bind at a consistent temperature, removing the need for any thermocycling during amplification, thereby avoiding or decreasing evaporation of the reaction mixture.

It should be appreciated that the description of the assembly reactions in the context of the oligonucleotides is not intended to be limiting. For example, other polynucleotides (e.g. single-stranded, double-stranded polynucleotides, restriction fragments, amplification products, naturally occurring polynucleotides, etc.) may be included in an assembly reaction, along with one or more oligonucleotides, in order to generate a polynucleotide of interest.

Cloning and In Vitro Expression

Some aspects of the invention provides for methods, devices and compositions for designing a protein having one or more desired characteristics, such as a desired function or property. In some embodiments, proteins can be designed and/or screened in silico. A wide varieties of computational methods can be used to generate and/or screen libraries of proteins to identify potential proteins or protein variants that can exhibit the desired characteristic. Once a number of proteins or protein variants have been identified, nucleic acids encoding the plurality of proteins or protein variants can be synthesized and the plurality of proteins or protein variants can be expressed and/or screened according to the methods disclosed herein to determine if the proteins have the desired characteristic.

In some embodiments, the invention provides arrays comprising libraries of proteins or variant proteins, with the library comprising at least about 100 different protein variants, with at least about 500 different protein variants being preferred, about 1000 different protein variants, about 10,000 different protein variants or more.

In some embodiments, a plurality of nucleic acids synthesized and/or assembled using the above methods and devices are expressed using in vitro transcription and/or translation system. In preferred embodiments, the plurality of nucleic acids are generated on a support (e.g. an array and the plurality of proteins are expressed on the same or a different support (e.g. array). The methods described above make possible the direct fabrication of nucleic acids of any desired sequence. In some embodiments, the plurality of nucleic acids encodes nucleic acid library members. In various embodiments of the invention, the nucleic acids synthesized and/or assembled using the above methods and devices can be introduced onto an appropriate vector by way of cloning. For example, the resulting polynucleotides can be individually cloned into an expression vector. The nucleic acid sequence may be inserted into the vector by a variety of procedures. In general, nucleic acids is inserted into an appropriate restriction endonuclease sites) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature.

Various vectors are publicly available. The vector may, for example, be in the form of a plasmid, cosmid, viral particle, or phage. Both expression and cloning vectors contain a nucleic acid sequence that enables the vector to replicate in one or more selected host cells. Such vector sequences are well known for a variety of bacteria, yeast, and viruses. Useful expression vectors that can be used include, for example, segments of chromosomal, non-chromosomal and synthetic DNA sequences. Suitable vectors include, but are not limited to, derivatives of SV40 and pcDNA and known bacterial plasmids such as col E1, pCR1, pBR322, pMal-C2, pET, pGEX as described by Smith, et al., Gene 57:31-40 (1988), pMB9 and derivatives thereof, plasmids such as RP4, phage DNAs such as the numerous derivatives of phage I such as NM98 9, as well as other phage DNA such as M13 and filamentous single stranded phage DNA; yeast plasmids such as the 2 micron plasmid or derivatives of the 2 m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like. The requirements are that the vectors are replicable and viable in the host cell of choice. Low- or high-copy number vectors may be used as desired.

In some embodiments, the synthetic sequences are cloned into cloning vectors. For example, the polynucleotide constructs may be introduced into an expression vector and transformed or transfected into a host cell. Any suitable vector may be used. Appropriate cloning vectors include, but are not limited to, plasmids, phages, cosmids, bacterial vector, bacterial artificial chromosomes (BACs), P1 derived artificial chromosomes (PACs), YAC, P1 vectors and the like. Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, J., Berman, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987). In some embodiments, a vector may be a vector that replicates in only one type of organism (e.g., bacterial, yeast, insect, mammalian, etc.) or in only one species of organism. Some vectors may have a broad host range. Some vectors may have different functional sequences (e.g., origins or replication, selectable markers, etc.) that are functional in different organisms. These may be used to shuttle the vector (and any nucleic acid fragment(s) that are cloned into the vector) between two different types of organism (e.g., between bacteria and mammals, yeast and mammals, etc.). In some embodiments, the type of vector that is used may be determined by the type of host cell that is chosen. Preferably, bacterium is used as a host cell and BAC vectors are utilized because of their capability to contain long nucleic acid sequences insert, typically, 50 to 350 kb (see Zhao et al., editors, Bacterial Artificial Chromosomes, Humana Press. Totowa, N.J. 2004, which is incorporated herein by reference).

In some embodiments, a library of promoter sequences is provided. In some embodiments, the library of promoters comprises a plurality of different promoters. Different promoters' sequences may be related or unrelated. In an exemplary embodiment, the promoter sequences may be obtained from a bacterial source. Each promoter sequence may be native or foreign to the polynucleotide sequence which it is operably linked to. Each promoter sequence may be any nucleic acid sequence which shows transcriptional activity in the host cell. A variety of promoters can be utilized. For example, the different promoter sequences may have different promoter strength. In some embodiments, the library of promoter sequences comprises promoter variant sequences. In a preferred embodiment, the promoter variants cover a wide range of promoter activities form the weak promoter to the strong promoter. A promoter used to obtain a library of promoters may be determined by sequencing a particular host cell genome. Putative promoter sequences may be then be identified using computerized algorithms such as the Neural Network of Promoter Prediction software (Demeter et al. (Nucl. Acids. Res. 1991, 19:1593-1599). Putative promoters may also be identified by examination of family of genomes and homology analysis. The library of promoter may be placed upstream of a single gene or operon or upstream of a library of genes.

A host cell may be transformed with the resulting nucleic acid constructs using any suitable technique (e.g., electroporation, chemical transformation, infection with a viral vector, etc.). Certain host organisms are more readily transformed than others. In some embodiments, all of the nucleic acid fragments and a linearized vector are mixed together and transformed into the host cell in a single step. However, in some embodiments, several transformations may be used to introduce all the fragments and vector into the cell (e.g., several successive transformations using subsets of the fragments). It should be appreciated that the linearized vector is preferably designed to have incompatible ends so that it can only be circularized (and thereby confer resistance to a selectable marker) if the appropriate fragments are cloned into the vector in the designed configuration. This avoids or reduces the occurrence of "empty" vectors after selection. The nucleic acids may be introduced into the host cell by any means known in the art, including, but not limited to, transformation, transfection, electroporation, microinjection, etc. In particular non-limiting embodiments of the invention, one or more nucleic acid may be introduced into a parental host cell, which is then propagated to produce a population of progeny host cells containing the nucleic acids. Mini-prep can be performed therefrom to purify the nucleic acids for further testing (e.g., sequencing). Clones having the correct or desired nucleic acids can be subcloned for in vitro protein synthesis or in vitro transcription/translation.

The nucleic acid constructs can be constructed to include appropriate promoter and translation sequences for in vitro protein synthesis or in vitro transcription/translation. Any suitable promoter can be used, such as the ara B, tac promoter, T7, T3 or SP6 promoters amongst others. The promoter is placed so that it is operably linked to the DNA sequences of the invention such that such sequences are expressed.

An In Vitro Protein Synthesis (IVPS) system, in general, includes cell extracts that support the synthesis of proteins in vitro from purified mRNA transcripts or from mRNA transcribed from DNA during the in vitro synthesis reaction. Such protein synthesis systems generally include a nucleic acid template that encodes a protein of interest. The nucleic acid template is an RNA molecule (e.g., mRNA) or a nucleic acid that encodes an mRNA (e.g., RNA, DNA) and be in any form (e.g., linear, circular, supercoiled, single stranded, double stranded, etc.). Nucleic acid templates guide production of the desired protein. IVPS systems can also be engineered to guide the incorporation of detectably labeled amino acids, or unconventional or unnatural amino acids, into a desired protein.

In a generic IVPS reaction, a gene encoding a protein of interest is expressed in a transcription buffer (e.g., having appropriate salts, detergents and pH), resulting in mRNA that is translated into the protein of interest in an IVPS extract and a translation buffer (e.g., having appropriate salts, detergents and pH). The transcription buffer, IVPS extract and translation buffer can be added separately, or two or more of these solutions can be combined before their addition, or added contemporaneously. To synthesize a protein of interest in vitro, an IVPS extract generally at some point comprises a mRNA molecule that encodes the protein of interest. In early IVPS experiments, mRNA was added exogenously after being purified from natural sources or prepared synthetically in vitro from cloned DNA using bacteriophage RNA polymerases. In other systems, the mRNA is produced in vitro from a template DNA; both transcription and translation occur in this type of IVPS reaction. Techniques using coupled or complementary transcription and translation systems, which carry out the synthesis of both RNA and protein in the same reaction, have been developed. In such in vitro transcription and translation (IVTT) systems, the IVPS extracts contain all the components necessary both for transcription (to produce mRNA) and for translation (to synthesize protein) in a single system. An early IVTT system was based on a bacterial extract (Lederman and Zubay, Biochim, Biophys. Acta, 1-49: 253, 1967). In IVTT systems, the input nucleic acid is DNA, which is normally much easier to obtain than mRNA, and more readily manipulated (e.g., by cloning, site-specific recombination, and the like).

An IVTT reaction mixture typically comprises the following components: a template nucleic acid, such as DNA, that comprises a gene of interest (GOI) operably linked to at least one promoter and, optionally, one or more other regulatory sequences (e.g., a cloning or expression vector containing the GOI); an RNA polymerase that recognizes the promoter(s) to which the GOI is operably linked and, optionally, one or more transcription factors directed to an optional regulatory sequence to which the template nucleic acid is operably linked; ribonucleotide triphosphates (rNTPs); ribosomes; transfer RNA (tRNA); optionally, other transcription factors and co-factors therefor; amino acids (optionally comprising one or more detectably labeled amino acids); one or more energy sources, (e.g., ATP, GTP); and other or optional translation factors (e.g., translation initiation, elongation and termination factors) and co-factors therefor.

In some aspects, the invention relates to high throughput expression of proteins using in vitro transcription/translation. In preferred embodiments, the methods and devices use minimized sample volumes, such as such as microvolumes, nanovolumes, picovolumes or sub-picovolumes. Accordingly, aspects of the invention relate to methods and devices for amplification and/or assembly of polynucleotide sequences and of expression of proteins in small volume droplets on separate and addressable features of a support. In some embodiments, predefined reaction microvolumes of between about 0.5 pL and about 100 nL, may be used. However, smaller or larger volumes may be used. One would appreciate that the minimized sample volume increases the number of samples that can be processed in an efficient and parallel manner. Methods and devices of the present invention provide for minimizing the volume of a reaction while controlling the loss of liquid due to evaporation as discussed herein. In some embodiment, the transcription/translation reactions can be generated or performed within a vessel of minimized proportions. Minimizing the vessel size in relation to reaction volume can reduce the effects of evaporation. For example, the transcription/translation reaction can take place on a solid surface or support, such as an array. In some embodiments, the transcription/translation reactions can be performed on the same support than the support for nucleic acid assembly. For example, the transcription/translation reactions can be performed at a different feature or area than the assembly reactions. Yet in another embodiment, the transcription translation reactions are performed on a different support.

In some embodiments, a library of synthetic nucleic acid constructs integrated into a plasmid or in linear form can be transferred to individual wells of a micro-well plate or at specific location on s support, containing the appropriate transcription/translation reaction reagents. In some embodiments, a droplet based dispensing apparatus can be used to dispense droplets of transcription/translation reagents directly onto specific locations or distinct features of the solid surface, covering the deposited nucleic acid constructs, forming a self contained reaction volume. For example, droplets can be dispensed on one, two or all features having nucleic acids. The support with the reaction volumes can be inserted into a humidity controlled chamber as described herein to counteract evaporation. The chamber can control a humidity therein and minimize evaporation of the reaction volumes. Other humidity control mechanisms can also be used, such as "sacrificial" droplets placed around or in close proximity to the droplet of interest, a sealing layer or lid, etc.

In some embodiments, the reaction reagents can be tailored to the specific type of protein being expressed. For example, prokaryotic proteins can be expressed using bacterial reagents, such as an *E. cell* lysate based expression systems, e.g., the PureExpress® system from New England Biolabs. Eukaryotic proteins can also be expressed with compatible systems, including wheat germ (e.g., T7 coupled reticulocyte lysate TNT™ system (Promega, Madison, Wis.)) and erythrocyte lysate based expression systems. Incubation of the reaction under appropriate reaction conditions, such as 37° C., can be followed by an analysis of protein expression. In some embodiments, synthesized protein products can be separated using gel electrophoresis and visualized or imaged by staining or Western blot.

In some embodiments, the presence of proteins of interest can be assessed by measuring protein activity. A variety of protein activities can be assayed. Non-limiting examples include binding activity (e.g., specificity, affinity, saturation, competition), enzyme activity (kinetics, substrate specificity, product, inhibition), etc. Exemplary methods include, but are not limited to, spectrophotometric, co metric, fluorometric, calorimetric, chemiluminescent, light scattering, radiometric, chromatographic methods, Automation Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer, One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that, perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Some aspects of the present invention relate to performing protein expression in vitro. In some embodiments, after synthesis and assembly on a surface or solid support, the nucleic acids can be amplified and/or cloned. The resulting nucleic acid constructs with the appropriate regulatory sequences can be mixed with the reagents required for transcription and translation, for the on-surface production of the corresponding proteins encoded by the nucleic acids. These in vivo protein expression reactions can be performed, for example, at a micro-volume scale and in a mass parallel manner, thereby saving time and costs. These advantages make in vitro on-surface production of proteins an attractive platform for the high throughput production of protein libraries. Methods and devices of the present invention also provide an advantageous platform for high throughput enzyme assays of in vitro produced protein libraries and in vitro development of bio-processing pathways using combinatorial protein libraries.

The following examples illustrate some embodiments in accordance with the present invention, where methods and devices for synthetic nucleic acid synthesis and highly parallel in vitro protein library production on solid surfaces are provided.

Example 1: Building Genetic Constructs from Microarray Based Material

FIGS. 1A-D are schematic drawings of surface attached synthesis of nucleic acid constructs using microarray sourced oligonucleotide building blocks and ligation assembly.

Genes to be expressed in the platform can be produced using oligonucleotides generated from enzymatic manipulation of nucleic acid microarrays (FIG. 1A, 10). On the microarray are groups of oligonucleotides (20) containing the genetic information required to build a target nucleic acid construct. Specifically, a universal primer (30) that hybridizes to the single stranded DNA (40) that makes up the microarray is introduced along with a polymerase such as the Kienow fragment of DNA polymerase I from *Escherichia coli* (50) and other reaction components including salts, buffers and deoxynucleotides. The universal primer (30) can include sequences that can be recognized and cleaved by appropriate enzymes (70). These components are used to create a complementary second strand of DNA (60), essentially copying the information contained within the nucleic acid on the microarray onto a recoverable molecule. Using enzymes (70) that cleave the universal primer (30), the universal primer can be fragmented (80) and removed by washing the microarray surface.

The copied single-stranded construction oligonucleotides can then be released solution, thereby forming a pool of construction oligonucleotides in solution. For example, the construction oligonucleotides can be eluted by heating the microarray in a buffer solution at high temperature, for instance 95° C., resulting in a plurality of populations of oligonucleotides (FIG. B, 65). Each population of oligonucleotides (1, 2, 3, 4, . . . , N+1, N+2, N+3, N+4, N+5) can have a predefined sequence, each complementary to the oligonucleotide sequence on the corresponding spot or feature on the solid surface. Together the plurality of populations of oligonucleotides (65) can constitute nucleic acids of interest. Preferably, each population of construction oligonucleotides has a sequence complementary to a next population of oligonucleotides. For example, oligonucleotide 2 has a first sequence complementary to a terminus sequence of oligonucleotide 1 and has a second distinct sequence complementary to a sequence of oligonucleotide 3. In certain embodiments, a plurality of nucleic acids of interest 5, 10, 20, 30, 50, 100, 200, 500, 1000, $10^4$, $10^5$, $10^6$, $10^7$, etc. can be produced from a single microarray. In some embodiments, a library of nucleic acid variants (e.g., 5, 10, 20, 30, 50, 100, 200, 500, 1000, $10^4$, $10^5$, $10^6$, $10^7$, etc.) can be produced from a single microarray.

Eluted oligonucleotides (65) can be transferred to a second area of the same array or an area of a second array having that anchor oligonucleotides immobilized on its surface (e.g. oligonucleotides A, FIG. 1C, 90). Anchor oligonucleotides can be complementary to and can hybridize with the terminus, such as the 5' or the 3' terminus of the DNA construct to be assembled (e.g., free oligonucleotide 1). The anchor oligonucleotides (oligonucleotides A, 90) can act as points of nucleation for the construction of the DNA product on the surface of the microarray (FIG. 1D, 100). In some embodiments, oligonucleotide 1 has a sequence complementary to the 5' end of the anchor oligonucleotide and a sequence complementary to the 3' end of oligonucleotide 2. In some embodiments, the construction oligonucleotides have a 3' terminus sequence complementary to a 5' terminus sequence of a first oligonucleotide and a distinct 5' terminus sequence complementary to the 3' terminus sequence of a second oligonucleotide. For example, oligonucleotides A, 1, 2, 3, 4, . . . , N+1, N+2, N+3, N+4, N+5 can sequentially hybridize with one another where complementary sequences are present. The hybridization conditions, temperature, salts concentration, buffer pH, etc.) can be adjusted to allow stringent or relaxed hybridization.

Construction oligonucleotide (e.g., 1, 2, 3, 4, . . . , N+1, N+2, N+3, N+4, N+5) of the target nucleic acid product can be incubated on the surface of the array, in microvolumes (e.g., individual droplet on each spot, or a plurality of droplets combined), in the presence of ligase and appropriate buffer components. Ligation can be achieved using a variety of different commercially available ligase enzymes. Low temperature (37° C. or lower) ligation can be performed using T4 DNA Ligase, available from New England Biolabs. High temperature (greater than 37° C.) ligation can be performed using thermophilic or thermostable ligases, such as Taq ligase and 9° N Ligase, available from New England Biolabs, and Ampligase®, available from Epicentre® Biotechnologies, according to manufacturer's instructions. After incubation at the appropriate temperature, unincorporated oligonucleotides and/or unwanted reagents can be removed by one or more rounds of washing. In this way, oligonucleotides (65) can be assembled into a full length nucleic acid of interest. It should be appreciated that a plurality of nucleic acids of interest can be produced in a highly parallel manner on one or more arrays.

In certain embodiments, the nucleic acid of interest can include, in addition to e.g., the gene of interest that encodes a protein of interest, ether genetic elements that regulate transcription and/or translation or facilitate selection. For example, genetic elements such as the promoter, ribosome binding site, transcriptional terminator, as well as selectable markers can be included in synthetic microarray and incorporated into the final synthetic DNA construct.

Example 2: High Throughput Expression of High Content Gene Libraries

Assembled nucleic acids can then amplified using gene specific pruners and the polymerase chain reaction. Full length constructs can then be cloned into appropriate vectors for sequence confirmation. Cloning can efficiently be accomplished using commercially available kits, such as the TOPO® line of cloning kits from Invitrogen or the StrataClone™ line from Agilent Technologies. Resultant plasmids can be transformed into *E. coli*, purified and sequenced to identify constructs with the desired sequence. Constructs with the appropriate genetic elements for transcription/translation can also be directly sequenced without cloning and transformation.

Nucleic acid constructs with the correct sequence can be cloned and/or subcloned into a plasmid containing the appropriate genetic elements (e.g., promoter, ribosome binding site, transcriptional terminator) for the in vitro expression of the corresponding proteins. Alternatively, in embodiments where the genetic elements have been included in the final synthetic nucleic acid construct, any plasmid can be used for cloning the construct. Constructs with the appropriate genetic elements can also be used in a linear form and subject to in vitro expression, without the need for cloning into a destination plasmid.

Various in vitro transcription/translation systems described herein can be used. For example, for expression of eukaryotic proteins, extract of wheat germ can be used, e.g., the PureExpress® system (New England Biolabs, Ipswich, Ma.) and the T7 coupled reticulocyte lysate TNT™ system (Promega, Madison, Wis.). The in vitro expression can be performed in various formats, e.g., in a multi-well plate or on a solid surface support (e.g. array).

FIGS. 2A-2C are schematic drawings of in vitro transcription and translation of synthetic nucleic acid (e.g. genes of interest) in micro-well plate or on solid surface support formats.

For the system described in FIG. 2A, a T7 promoter (100) and an *E. coli* ribosome binding site (110) can be included upstream of a gene of interest (120). Downstream of the gene of interest is a transcriptional terminator (130). Other suitable promoters can include SP6 or T3. Commercially available products can be used and optimized for expression of proteins. For instance, the pET line of bacterial expression plasmids from EMD Chemicals Group can be used as a destination plasmid for in vitro expression of proteins in a bacterial expression system using the T7 promoter.

The present invention, in one embodiment, features high throughput expression of proteins using in vitro transcription/translation that can be facilitated by a minimization of sample volumes. The minimized sample volume increases the number of samples that can be processed in an efficient and parallel manner. Methods and devices of the present invention provide for minimizing the volume of a reaction while controlling the loss of liquid due to evaporation as discussed herein. In one embodiment, the transcription/translation reaction can be generated or performed within a vessel of minimized proportions. In another embodiment, the transcription/translation reaction can take place on a solid surface or support.

Minimizing the vessel size in relation to reaction volume can reduce the effects of evaporation. For example, a library of synthetic nucleic acid constructs integrated into a plasmid (140) or in linear form (150) can be transferred to individual wells of a micro-well plate containing the appropriate transcription/translation reaction reagents (160). The reaction reagents can be tailored to the specific type of protein being expressed. For example, prokaryotic proteins can be expressed using bacterial reagents, such as an *E. coli* lysate based expression systems, e.g., the PureExpress® system from New England Biolabs. Eukaryotic proteins can also be expressed with compatible systems, including wheat germ (e.g., T7 coupled reticulocyte lysate TNTTM system (Promega, Madison, Wis.)) and erythrocyte lysate based expression systems. Incubation of the reaction at the appropriate temperature, such as 37° C. can be followed by an analysis of successful expression of the proteins encoded by the gene library (170). This analysis can take the form of direct inspection of the protein products using gel electrophoresis and visualization of separated proteins using staining and imaging. For example, proteins can be separated by gel electrophoresis and visualized by staining the gel (e.g. Coomassie Brilliant Blue R-250 or silver stain), allowing visualization of the separated proteins, or processed further (e.g. Western blot). Measurement of protein activity can also be used to confirm the presence of the expressed proteins.

Other methods and devices for performing high throughput protein expression can involve the transcription/translation reaction taking place on a solid surface (180). For instance, a library of linear nucleic acid constructs can be hybridized to anchor oligonucleotides present on the surface (180) allowing retention of the linear nucleic acid construct (190) on the solid surface. A droplet based dispensing apparatus (200) as described herein can be used to dispense droplets of transcription/translation reagents directly onto specific locations of the solid surface (180), covering the deposited nucleic acid constructs (190), forming a self contained reaction volume (220). The solid surface with the reaction mixtures can be inserted into a humidity controlled chamber (230) as described herein to counteract evaporation. The chamber can control a humidity therein and minimize evaporation of the reaction mixtures. Other humidity control mechanisms can also be used, such as "sacrificial" droplets placed around or in close proximity to the droplet of interest, a sealing layer or lid, etc. The expression of proteins (170) from the nucleic acid library can then be assayed through direct inspection by gel electrophoresis and staining, or measurement of protein activity.

A variety of protein activities can be assayed. Non-limiting examples include binding activity (e.g., specificity, affinity, saturation, competition), enzyme activity (kinetics, substrate specificity, product, inhibition), etc. Exemplary methods include, but are not limited to, spectrophotometric, colorimetric, fluorometric, calorimetric, chemiluminescent, light scattering, radiometric, chromatographic methods.

Example 3: High Throughput Analysis of On-Surface Expressed Enzyme Activity

FIGS. 3A-3D are schematic drawings of high throughput enzyme assays using in vitro expression of synthetic nucleic acid constructs on a solid support surface and analysis by liquid chromatography linked with mass spectrometry.

High throughput enzyme assays can be used to measure the activity of proteins expressed in vitro on a solid surface, as shown in FIGS. 3A-3D. Synthetic nucleic acid constructs (300) with the appropriate promoter and/or ribosome binding site are anchored to the solid support (310) and covered with a droplet of transcription/translation reagent mix (320) and incubated in a humidity controlled chamber to minimize evaporation (330), as described herein. After completion of the protein expression phase of the process (FIG. 3B), the solid surface is removed from the humidity chamber and protein activity can be assessed. In some embodiments, a droplet based dispensing apparatus (340) can dispense reagents appropriate for supporting enzyme activity at specific location (or features) on the support or solid surface. For example, reagents can be added in a drop wise manner (350). The solid surface is then placed back in the humidity control chamber (FIG. 3C) which can act as a reaction chamber. Under suitable conditions (e.g. suitable temperature conditions) the enzyme (355) converts the substrate (360) to product (370). When the enzymatic reaction is complete (FIG. 3D) the solid surface can be removed from the humidity control chamber and the presence of product can be assayed. Sampling can be performed by an automated sampling device including a sample uptake tube (380), a pump (385) and the appropriate separation method, for example a chromatography column (390) capable of separating the enzyme reaction product from the substrate, reactants or contaminating molecules. The presence of the enzyme reaction product can be detected in a variety of manners, including fluorescence emissions, absorbance of light or mass spectrometry (395). Other technologies, such as the RapidFire@ technology from Biocius Life Sciences can also be used to allow high throughput measurement of reaction products, analyzing thousands of reactions per day (see, e.g., U.S. Pat. Nos. 6,932,939, 6,812,030, 7,100,460, and 7,588,725).

Example 4: Combinatorial Multi-Enzyme Pathway Development Using On-Surface Expression FIGS. 4A-4D are schematic drawings of multi-gene pathway development using synthetic genes and combinatorial libraries of said genes.

On-surface gene synthesis as described herein can be used to generate a large number of different constructs at low cost. Coupled with on-surface protein expression as described herein, the present invention provides an enzymatic pathway development platform using highly complex combinatorial libraries. As shown in FIGS. 4A-4D, a microarray (400) contains the oligonucleotides (410) needed to build a set of genes (420) expressing a set of proteins that make up an enzymatic pathway of interest (e.g. biosynthetic pathway). Each of these genes (420) can be modified in a variety of ways, giving diversity to the combinatorial library. For instance, the genes can include mutations, be placed under control of different regulatory sequences, and/or be expressed as fusion proteins having selectable markers fluorescent marker, binding partners, affinity tags, chromatography tags, epitopes, HA-tag, etc).

In one example, each gene can placed under the control of two different promoters (430) giving high (pH) or low (pL) levels of relative expression. Resultant linear nucleic acid constructs (440) are mixed together in a well plate or on a feature of an array (FIG. 4B, 450) to give all the potential combinations (460) in a plurality of wells or features (e.g., M1 to M8). These mixtures of linear constructs can be immobilized (FIG. 4C, 465) on the surface of a solid support (467). As described above, a transcription/translation reaction mixture can be dispensed onto the individually arrayed combinations of genes M1-M8 (468). The solid support can be incubated within a humidity controlled chamber (470) to minimize evaporation at the appropriate temperature, as described herein. Within each of the reaction volume (472) transcription and translation reactions can result in the production of the protein combinations (475) encoded by the arrayed gene combinations, representing, e.g., a metabolic pathway of interest or a biosynthetic pathway of interest. It should be appreciated that a plurality of gene combinations representing a plurality of metabolic pathways of interest can be produced in a highly parallel manner in accordance with the present invention.

Once the transcription/translation reaction is complete, the solid support (467) can be removed from the humidity chamber (470) and a droplet based dispensing apparatus (480) can be used to dispense reagents (490) containing appropriate substrates (492) and other reaction components such as buffers, salts and cofactors required for activity assay of the protein combinations (475) within the reaction. The protein combinations (475), if present at appropriate combination and/or concentration, can convert the substrates (492) to product (495) under appropriate reaction conditions. The product (495) can then be analyzed for instance using column chromatography and mass spectrometry, as described above. Thus, activities of the mixtures M1 to M8 can be prepared side by side, to identify the gene/protein combination that most effective at converting substrate to product.

EQUIVALENTS

The present invention provides among other things novel methods and devices for protein arrays. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT application PCT/US09/55267; U.S. provisional application 61/257,591 filed Nov. 3, 2009; U.S. provisional application 61/264,643 filed Nov. 25, 2009; U.S. provisional application 61/264,632 filed Nov. 25, 2009; U.S. provisional application 61/264,641 filed Nov. 25, 2009; U.S. provisional application 61/293,192 filed Jan. 7, 2010; U.S. provisional application 61/310,100 filed Mar. 3, 2010; and U.S. provisional application 61/310,100 filed Mar. 3, 2010. All publications, patents and patent applications and sequence database entries mentioned herein are hereby incorporated by reference in their entirety as if each individual publication, patent or patent application is specifically and individually indicated to be incorporated by reference.

What is claimed is:

1. A method for preparing a plurality of proteins comprising:
   (a) providing a plate comprising a plurality of wells,
      wherein the plurality of wells comprises a plurality of nucleic acids, each nucleic acid having a predefined sequence and encoding a protein, and
      wherein the nucleic acids of each well are immobilized on one or more supports; and
   (b) expressing in vitro a plurality of proteins from the plurality of nucleic acids,
      wherein the proteins are expressed in the wells of the plate in volumes having a size of 0.5 picoliters to 100 nanoliters.

2. The method of claim 1, wherein the plurality of nucleic acids is immobilized on beads.

3. The method of claim 1, wherein the nucleic acids of each well are immobilized on one bead.

4. The method of claim 1, wherein the plurality of nucleic acids is immobilized on the surface of the plate.

5. The method of claim 1, wherein each well in the plurality of wells comprises a nucleic acid having a unique predetermined sequence.

6. The method of claim 5, wherein the plurality of proteins comprises a plurality of different proteins.

7. The method of claim 1, wherein the plurality of nucleic acids comprises nucleic acids having different predetermined sequences.

8. The method of claim 7, wherein the nucleic acids of each well comprise the same predetermined sequence.

9. The method of claim 7, wherein the plurality of proteins comprises a plurality of different proteins.

10. The method of claim 1, wherein the proteins are expressed in the wells of the plate in volumes having a size of 1 picoliter to 1 nanoliter.

* * * * *

SEQUENCE LISTING

```
<160> NUMBER OF SEQ ID NOS: 1

<210> SEQ ID NO 1
<211> LENGTH: 10
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n can be a or g

<400> SEQUENCE: 1 nccaccaugg                                                          10
```